United States Patent [19]

Chappell et al.

[11] Patent Number: 5,306,862
[45] Date of Patent: Apr. 26, 1994

[54] METHOD AND COMPOSITION FOR INCREASING STEROL ACCUMULATION IN HIGHER PLANTS

[75] Inventors: Joseph Chappell, Lexington, Ky.; Court A. Saunders, Clarendon Hills, Ill.; Fred R. Wolf, Naperville, Ill.; Richard E. Cuellar, Glen Ellyn, Ill.

[73] Assignee: AMOCO Corporation, Naperville, Ill.

[21] Appl. No.: 596,467

[22] Filed: Oct. 12, 1990

[51] Int. Cl.$^5$ .......................... A01H 1/04; A01H 1/02; C12N 15/00; C12P 7/22
[52] U.S. Cl. .................................... 800/205; 800/250; 800/255; 800/DIG. 43; 800/DIG. 44; 800/DIG. 15; 800/DIG. 26; 800/DIG. 27; 800/DIG. 40; 800/DIG. 47; 800/DIG. 55; 800/DIG. 56; 435/69.1; 435/70.1; 435/172.3; 435/156; 435/189
[58] Field of Search ................... 435/69.1, 70.1, 172.3, 435/183, 240.4, 320.1, 156, 189; 800/205, 250, DIG. 43, 255

[56] References Cited

U.S. PATENT DOCUMENTS 4,956,282 9/1990 Goodman et al. ............... 435/69.51

FOREIGN PATENT DOCUMENTS 89310973.6 10/1989 European Pat. Off. .
8901309 3/1989 PCT Int'l Appl. .

OTHER PUBLICATIONS

Chappel et al. 1989, Plant Cell Reports 8(1): 48–52.
Vogeli et al. 1988 Plant Physiol. 88(4):1291–1296.
Downey et al. 1980, Biochem. Biophys. Res. Commun. 94(3):974–979.
Caelles, C. et al. 1991 (Abstract #853) "Isolation and Structural Characterization of a cDNA Encoding *Arabidopsis thalia* 3-hydroxy-3-methylglutaryl Coenzyme A Reductase" *Plant Molecular Biology* 13:627–638.
Chappell, J. et al. 1991 (Abstract #853) "Is HMG-CoA Reductase a Rate Limiting Step for Isoprenoid Metabolism?" *Plant Physiology (Supplement) 96(1):127*.
Narita, J. et al. 1989 "Tomato Hydroxymethylglutaryl-CoA Reductase is Required Early in Fruit Development But Not During Ripening" *The Plant Cell* 1:181–190.
Gil, G. et al. 1985. "Membrane-Bound Domain of HMG CoA Reductase Is Required for Sterol-Enhanced Degradation of the Enzyme" *Cell* 41:249–258.
Chin, D. et al. 1985 (Biol. Abstract 80(2):AB-376 #12523) "Sterols Accelerate Degradation of Hamster 3-hydroxy-3-methylglutaryl Coenzyme A Reductase Encoded By a Constitutively Expressed Complementary DNA" *Mol. Cell Biol.* 5(4):634–641.
Learned, R. et al. 1989, "3-Hydroxy-3-Methylglutaryl-Coenzyme A Reductase From *Arabidopsis thaliana* Is Structurally Distinct from the Yeast and Animal Enzymes" *Proc. Natl. Acad. Sci.* 86:2779–2783.
Downing, J. et al. 1980 (Chem. Abstracts 93:484 #93:65791y) "The Isolation of Two Mutants of Saccharomyces cerevisiae Which Demonstrate Increased Activity of 3-Hydroxy-3-methylglutaryl Coenzyme a Reductance."
LaGrimini, L. et al. 1990, "Peroxidase-Induced Wilting in Transgenic Tobacco Plants" *The Plant Cell* 2:7–18.
Gil et al., *Cell*, 41:249–258, (1985).

(List continued on next page.)

Primary Examiner—David T. Fox
Attorney, Agent, or Firm—Joanne M. Giesser

[57] ABSTRACT

A method of increasing sterol accumulation in a plant by increasing the copy number of a gene encoding a polypeptide having HMG-CoA reductase activity is disclosed. The copy number is preferably increased by transforming plants with a recombinant DNA molecule comprising a vector operatively linked to an exogenous DNA segment that encodes a polypeptide having HMG-CoA reductase activity, and a promoter suitable for driving the expression of said polypeptide. Also disclosed are a method of increasing cycloartenol accumulation in a plant, a method of increasing the resistance of plants to pests and the transformed plants themselves.

22 Claims, 23 Drawing Sheets

OTHER PUBLICATIONS

Basson et al., *Molecular and Cellular Biology*, 8:3797–3808 (1988).
Chin et al., *Nature*, 308:613–617 (1984).
Klein et al., *Plant Physiol.*, 91:440–444 (1989).
Horsch et al., *Science*, 227:1229–1231 (1985).
Fromm et al., *Nature*, 319:791–793 (1986).
Odell et al., *Nature*, 313 (1985).
Marcotte et al., 335:454–457 (1988).
Fromm et al., *Proc. Natl. Acad. Sci.*, USA, 82:5824–5828 (1985).
Bytebier et al., *Proc. Natl. Acad. Sci.*, USA, 84:5345–5349 (1987).
Klein et al., *Proc. Natl. Acad. Sci.*, 85:8502–8505 (1988).
Berger et al., *Proc. Natl. Acad. Sci.*, 8402–8406 (1989).
Yang et al., *Proc. Natl. Acad. Sci.*, 87:4144–4148 (1990).
Fraley et al., *Proc. Natl. Acad. Sci.*, 80:4803–4807 (1983).
Rine et al., *Proc. Natl. Acad. Sci.*, 80:6750–6754 (1983).
Russell et al., *Current Topics In Plant Biochemistry*, 4:191–206 (1985).
Schardi et al., *Gene* 61:1–11 (1987).
Basson et al., *Molecular and Cellular Biology*, 8:3797–3808 (1988).
Liscum et al., *The Journal of Biological Chemistry*, 260:522–530 (1985).
Jorgensen et al., *Mol. Gen. Genet.*, 207:471–477 (1987).
Uchimiya et al., *Mol. Gen. Genet.*, 204:204–207 (1986).
Spielman et al., *Not. Gen. Genet.*, 205:34–41 (1986).
Poulsen et al., *Mol. Gen. Genet.*, 205:193–200 (1986).
Bard et al., *Journal of General Microbiology*, 125:415–420 (1981).
Vasil, I. K., *Bio/Technology*, 8:797 (1990).
Wenzler et al., *Plant Molecular Biology*, 12:41–50 (1989).
Keller et al., *The EMBO Journal*, 8:1309–1314 (1989).
Simpson et al., *Science*, 233:34–38 (1986).
Brown et al., *Journal of Lipid Research*, 21:505–517 (1980).
Caberera et al., *J. Biol. Chem.*, 261(8):3578–3583 (1986).
Hasumi et al., *Eur. J. Biochem.*, 164:547–552 (1987).
Jordan-Stark et al., *J. of Biol. Chem.*, 264:17919–17923 (1989).
Orci et al., *Cell*, 36–835–845 (1984).
Chin et al., *Proc. Natl. Acad. Sci.*, USA 79:1185–1189 (1982).
Goldstein et al., *Nature*, 343:425–430 (1990).
Luskey, K. L., *Molecular and Cellular Biology*, 7(5):1881 (1987).
Benfey et al., *Science*, 244:174 (1989).
Langridge et al., *Proc. Ntl. Acad. Sci.*, USA 86:3219 (1989).
Mayerhofer et al., *The EMBO Journal*, 10(3):697 (1991).
Toriyama et al., *Biotechnology*, 6:1072 (1988).

```
TGTATGTCTT GTCTTTCTCC TAAGGGGCGT AGGCTCATTG ATAACTCATG TCCTCACCTT      60

GCACTCCTTT TGGAATTATT TGGTTTGAGT GAAGAAGACC GGACCTTCGA GGTTCGCAAC     120

TTAAACAATA GACTTGTGAG GATCCAGGGA CCGAGTGGCT ACA ATG TTG TCA CGA      175
                                             Met Leu Ser Arg
                                              1

CTT TTC CGT ATG CAT GGC CTC TTT GTG GCC TCC CAT CCC TGG GAA GTT      223
Leu Phe Arg Met His Gly Leu Phe Val Ala Ser His Pro Trp Glu Val
 5                  10                  15                  20

ATT GTG GGG ACG GTG ACA CTT ACC ATC TGT ATG ATG TCC ATG AAC ATG      271
Ile Val Gly Thr Val Thr Leu Thr Ile Cys Met Met Ser Met Asn Met
                25                  30                  35

TTC ACT GGC AAC AAC AAG ATC TGT GGT TGG AAT TAC GAG TGC CCA AAA      319
Phe Thr Gly Asn Asn Lys Ile Cys Gly Trp Asn Tyr Glu Cys Pro Lys
            40                  45                  50

TTT GAG GAG GAT GTA TTG AGC AGT GAC ATC ATC ATC CTC ACC ATA ACA      367
Phe Glu Glu Asp Val Leu Ser Ser Asp Ile Ile Ile Leu Thr Ile Thr
        55                  60                  65

CGG TGC ATC GCC ATC CTG TAC ATT TAC TTC CAG TTC CAG AAC TTA CGT      415
Arg Cys Ile Ala Ile Leu Tyr Ile Tyr Phe Gln Phe Gln Asn Leu Arg
 70                  75                  80
```

Figure 2-1

```
CAG CTT GGG TCG AAG TAT ATT TTA GGT ATT GCT GGC CTG TTC ACA ATT         463
Gln Leu Gly Ser Lys Tyr Ile Leu Gly Ile Ala Gly Leu Phe Thr Ile
 85                  90                  95                 100

TTC TCA AGT TTT GTC TTT AGT ACA GTC GTC ATT CAC TTC TTA GAC AAA         511
Phe Ser Ser Phe Val Phe Ser Thr Val Val Ile His Phe Leu Asp Lys
            105                 110                 115

GAA CTG ACG GGC TTA AAT GAA GCT TTG CCC TTT TTC CTG CTT TTG ATT         559
Glu Leu Thr Gly Leu Asn Glu Ala Leu Pro Phe Phe Leu Leu Leu Ile
        120                 125                 130

GAC CTT TCT AGA GCG AGT GCA CTA GCA AAG TTT GCC CTA AGT TCA AAC         607
Asp Leu Ser Arg Ala Ser Ala Leu Ala Lys Phe Ala Leu Ser Ser Asn
            135                 140                 145

TCT CAG GAT GAA GTA AGG GAA AAT ATA GCT CGC GGA ATG GCA ATT CTG         655
Ser Gln Asp Glu Val Arg Glu Asn Ile Ala Arg Gly Met Ala Ile Leu
    150                 155                 160

GGC CCC ACA TTC ACC CTT GAT GCT CTT GTG GAA TGT CTT GTA ATT GGA         703
Gly Pro Thr Phe Thr Leu Asp Ala Leu Val Glu Cys Leu Val Ile Gly
165                 170                 175                 180

GTT GGC ACC ATG TCA GGG GTG CGT CAG CTT GAA ATC ATG TGC TTT             751
Val Gly Thr Met Ser Gly Val Arg Gln Leu Glu Ile Met Cys Phe
                185                 190                 195
```

Figure 2-2

| | | | | | | | | | | | | | | | | |
|---|---|---|---|---|---|---|---|---|---|---|---|---|---|---|---|---|
| GGC | TGC | ATG | TCT | GTG | CTT | GCC | AAC | TAC | TTC | GTG | TTC | ATG | ACA | TTT | TTC | 799 |
| Gly | Cys | Met | Ser | Val | Leu | Ala | Asn | Tyr | Phe | Val | Phe | Met | Thr | Phe | Phe | |
| 200 | | | | | | | 205 | | | | | | 210 | | | |
| CCA | GCG | TGT | GTG | TCC | CTG | GTC | CTT | GAG | CTT | TCT | CGG | GAA | AGT | CGA | GAG | 847 |
| Pro | Ala | Cys | Val | Ser | Leu | Val | Leu | Glu | Leu | Ser | Arg | Glu | Ser | Arg | Glu | |
| 215 | | | | | | 220 | | | | | | 225 | | | | |
| GGT | CGT | CCA | ATT | TGG | CAG | CTT | AGC | CAT | TTT | GCC | CGA | GTT | TTG | GAA | GAA | 895 |
| Gly | Arg | Pro | Ile | Trp | Gln | Leu | Ser | His | Phe | Ala | Arg | Val | Leu | Glu | Glu | |
| 230 | | | | | 235 | | | | | | 240 | | | | | |
| GAA | GAG | AAT | AAA | CCA | AAC | CCT | GTA | ACC | CAA | AGG | GTC | AAG | ATG | ATT | ATG | 943 |
| Glu | Glu | Asn | Lys | Pro | Asn | Pro | Val | Thr | Gln | Arg | Val | Lys | Met | Ile | Met | |
| 245 | | | | | 250 | | | | | 255 | | | | | 260 | |
| TCT | TTA | GGT | TTG | GTT | CTT | GTT | CAT | GCT | CAC | AGT | CGA | TGG | ATA | GCT | GAT | 991 |
| Ser | Leu | Gly | Leu | Val | Leu | Val | His | Ala | His | Ser | Arg | Trp | Ile | Ala | Asp | |
| | | | | 265 | | | | | 270 | | | | | 275 | | |
| CCT | TCC | CCT | CAG | AAT | AGC | ACA | GAA | CAT | TCT | AAA | GTC | TCC | TTG | GGA | | 1039 |
| Pro | Ser | Pro | Gln | Asn | Ser | Thr | Glu | His | Ser | Lys | Val | Ser | Leu | Gly | | |
| | | 280 | | | | | 285 | | | | | 290 | | | | |
| CTG | GAT | GAA | GAT | GTG | TCC | AAG | AGA | ATT | GAA | CCA | AGT | GTT | TCT | CTC | TGG | 1087 |
| Leu | Asp | Glu | Asp | Val | Ser | Lys | Arg | Ile | Glu | Pro | Ser | Val | Ser | Leu | Trp | |
| | 295 | | | | | 300 | | | | | 305 | | | | | |

Figure 2-3

```
CAG TTT TAT CTC TCC AAG ATG ATC AGC ATG GAC ATT GAA CAA GTG GTT    1135
Gln Phe Tyr Leu Ser Lys Met Ile Ser Met Asp Ile Glu Gln Val Val
    310                 315                 320

ACC CTG AGC TTA GCT TTT CTG TTG GCT GTC AAG TAC ATT TTC TTT GAA    1183
Thr Leu Ser Leu Ala Phe Leu Leu Ala Val Lys Tyr Ile Phe Phe Glu
    325                 330                 335                 340

CAA GCA GAG ACA GAG TCC ACA CTG TCT TTA AAA AAT CCT ATC ACG TCT    1231
Gln Ala Glu Thr Glu Ser Thr Leu Ser Leu Lys Asn Pro Ile Thr Ser
    345                 350                 355

CCT GTC ACC CCA AAG AAA GCT CCA GAC AAC TGT TGT AGA CGG GAG         1279
Pro Val Thr Pro Lys Lys Ala Pro Asp Asn Cys Cys Arg Arg Glu
    360                 365                 370

CCT CTG CTT GTG AGA AGG AGC GAG AAG CTT TCA TCG GTT GAG GAG GAG    1327
Pro Leu Leu Val Arg Arg Ser Glu Lys Leu Ser Ser Val Glu Glu Glu
    375                 380                 385

CCT GGG GTG AGC CAA GAT AGA AAA GTT GAG GTT ATA AAA CCA TTA GTG    1375
Pro Gly Val Ser Gln Asp Arg Lys Val Glu Val Ile Lys Pro Leu Val
    390                 395                 400

GTG GAA ACT GAG AGT GCA AGC AGA GCT ACA TTT GTG CTT GGC GCC TCT    1423
Val Glu Thr Glu Ser Ala Ser Arg Ala Thr Phe Val Leu Gly Ala Ser
    405                 410                 415                 420
```

Figure 2-4

```
GGG ACC AGC CCT CCA GTG GCA GCG AGG ACA CAG GAG CTT GAA ATT GAA        1471
Gly Thr Ser Pro Pro Val Ala Ala Arg Thr Gln Glu Leu Glu Ile Glu
                425                 430                 435

CTC CCC AGT GAG CCT CGG CCT AAT GAA GAA TGT CTG CAG ATA CTG GAG        1519
Leu Pro Ser Glu Pro Arg Pro Asn Glu Glu Cys Leu Gln Ile Leu Glu
                440                 445                 450

AGT GCC GAG AAA GGT GCA AAG TTC CTT AGC GAT GCA GAG ATC ATC CAG        1567
Ser Ala Glu Lys Gly Ala Lys Phe Leu Ser Asp Ala Glu Ile Ile Gln
                455                 460                 465

TTG GTC AAT GCC AAG CAC ATC CCA GCC TAC AAA TTG GAA ACC TTA ATG        1615
Leu Val Asn Ala Lys His Ile Pro Ala Tyr Lys Leu Glu Thr Leu Met
                470                 475                 480

GAA ACT CAT GAA CGT GGT GTA TCT ATT CGC CGG CAG CTC CTC TCC ACA        1663
Glu Thr His Glu Arg Gly Val Ser Ile Arg Arg Gln Leu Leu Ser Thr
                485                 490                 495                 500

AAG CTT CCA GAG CCT TCT TCT CTG CAG TAC CTG CCT TAC AGA GAT TAT        1711
Lys Leu Pro Glu Pro Ser Ser Leu Gln Tyr Leu Pro Tyr Arg Asp Tyr
                505                 510                 515

AAT TAT TCC CTG GTG ATG GGA GCT TGC TGT GAG AAT GTG ATC GGA TAT        1759
Asn Tyr Ser Leu Val Met Gly Ala Cys Cys Glu Asn Val Ile Gly Tyr
                520                 525                 530
```

Figure 2-5

```
ATG CCC ATC CCT GTC GGA GTA GCA GGG CCT CTG TGC CTG GAT GGT AAA      1807
Met Pro Ile Pro Val Gly Val Ala Gly Pro Leu Cys Leu Asp Gly Lys
            535                 540                 545

GAG TAC CAG GTT CCA ATG GCA ACA ACG GAA GGC TGT GTG GCC AGC          1855
Glu Tyr Gln Val Pro Met Ala Thr Thr Glu Gly Cys Val Ala Ser
            550                 555                 560

ACC AAC AGA GGC TGC AGG GCA ATA GGT CTT GGT GGA GGT GCC AGC AGC      1903
Thr Asn Arg Gly Cys Arg Ala Ile Gly Leu Gly Gly Gly Ala Ser Ser
            565                 570                 575         580

CGG GTC CTT GCA GAT GGG ATG ACC CGG GGC CCA GTG GTG CGT CTT CCT      1951
Arg Val Leu Ala Asp Gly Met Thr Arg Gly Pro Val Val Arg Leu Pro
                585                 590                 595

CGT GCT TGT GAT TCT GCA GAA GTG AAG GCC TGG CTT GAA ACA CCC GAA      1999
Arg Ala Cys Asp Ser Ala Glu Val Lys Ala Trp Leu Glu Thr Pro Glu
        600                 605                 610

GGG TTT GCG GTG ATA AAG GAC GCC TTC GAT AGC ACT AGC AGA TTT GCA      2047
Gly Phe Ala Val Ile Lys Asp Ala Phe Asp Ser Thr Ser Arg Phe Ala
            615                 620                 625

CGT CTA CAG AAG CTT CAT GTG ACC ATG GCA GGG CGC AAC CTG TAC ATC      2095
Arg Leu Gln Lys Leu His Val Thr Met Ala Gly Arg Asn Leu Tyr Ile
            630                 635                 640
```

Figure 2-6

| CGT Arg 645 | TTC Phe | CAG Gln | TCC Ser | AAG Lys | ACA Thr 650 | GGG Gly | GAT Asp | GCC Ala | ATG Met 655 | GGG Gly | ATG Met | AAC Asn | ATT Ile | TCC Ser 660 | 2143 |
| AAG Lys | GGC Gly | ACT Thr | GAG Glu 665 | AAA Lys | GCA Ala | CTT Leu | CTG Leu | AAG Lys 670 | CAG Gln | GAG Glu | TTC Phe | CCT Pro | GAA Glu 675 | | 2191 |
| ATG Met | CAG Gln | ATT Ile | CTG Leu 680 | GCA Ala | GTT Val | AGT Ser | GGT Gly | AAC Asn 685 | TAC Tyr | TGC Cys | ACT Thr | GAC Asp | AAG Lys 690 | AAA Lys | CCT Pro | 2239 |
| GCC Ala | GCA Ala | ATA Ile | AAC Asn 695 | TGG Trp | ATC Ile | GAG Glu | GGA Gly | AGA Arg 700 | GGA Gly | AAG Lys | ACA Thr | GTT Val | TTA Leu 705 | GTG Val | TGT Cys | GAA Glu | 2287 |
| GCT Ala | GTT Val | ATT Ile | CCA Pro 710 | GCC Ala | AAG Lys | GTG Val | AGA Arg | GTA Val 715 | GAA Glu | TTA Leu | AAG Lys | ACA Thr | ACT Thr 720 | ACG Thr | | 2335 |
| GAA Glu | GCT Ala | ATG Met | ATT Ile 725 | GAC Asp | GTA Val | AAC Asn | ATT Ile | AAC Asn 730 | AAG Lys | AAT Asn | CTT Leu | GTG Val | GGT Gly 735 | TCT Ser | GCC Ala 740 | 2383 |
| ATG Met | GCT Ala | GGG Gly | AGC Ser | ATA Ile 745 | GGA Gly | GGC Gly | TAC Tyr | AAT Asn | GCC Ala 750 | CAT His | GCA Ala | AAC Asn | ATC Ile | GTC Val 755 | | 2431 |

Figure 2-7

```
ACT GCT ATC TAC ATT GCA TGT GGC CAG GAT GCA GCA CAG AAT GTG GGG    2479
Thr Ala Ile Tyr Ile Ala Cys Gly Gln Asp Ala Ala Gln Asn Val Gly
            760                 765                 770

AGT TCA AAC TGT ATT ACT TTA ATG GAA GCA AGT GGT CCC ACG AAT GAA    2527
Ser Ser Asn Cys Ile Thr Leu Met Glu Ala Ser Gly Pro Thr Asn Glu
            775                 780                 785

GAC TTG TAT ATC AGC TGC ACC ATG CCA TCT ATA GAG ATA GGA ACT GTG    2575
Asp Leu Tyr Ile Ser Cys Thr Met Pro Ser Ile Glu Ile Gly Thr Val
        790                 795                 800

GGT GGG ACC AAC CTC CTA CCA CAG CAG GCC TGT CTG TGT CAG ATG CTA    2623
Gly Gly Thr Asn Leu Leu Pro Gln Gln Ala Cys Leu Cys Gln Met Leu
805                 810                 815                 820

GGT GTT CAA GGA GCG TGC AAA GAC AAT CCT GGA GAA AAT GCA CGG CAA    2671
Gly Val Gln Gly Ala Cys Lys Asp Asn Pro Gly Glu Asn Ala Arg Gln
        825                 830                 835

CTT GCC CGA ATT GTG TGT GGT ACT GTA ATG GCT GGG GAG TTG TCC TTG    2719
Leu Ala Arg Ile Val Cys Gly Thr Val Met Ala Gly Glu Leu Ser Leu
            840                 845                 850

ATG GCA GCA TTG GCA GCA GGA CAT CTT GTT AGA AGT CAC ATG GTT CAT    2767
Met Ala Ala Leu Ala Ala Gly His Leu Val Arg Ser His Met Val His
            855                 860                 865
```

Figure 2-8

```
AAC AGA TCG AAG ATA AAT TTA CAA GAT CTG CAA GGA ACG TGC ACC AAG      2815
Asn Arg Ser Lys Ile Asn Leu Gln Asp Leu Gln Gly Thr Cys Thr Lys
    870                     875                     880

AAG TCA GCT TGAGCAGCCT GACAGTATTG AACTGAAACA CGGGCATTGG              2864
Lys Ser Ala
885

GTTCTCAAGG ACTAACATGA AATCTGTGAA TTAAAAATCT CAATGCAGTG TCTTGTGGAA    2924

GATGAATGAA CGTGATCAGT GAGACGCCTG CTTGGTTTCT GGCTCTTTCA GAGACGTCTG    2984

AGGTCCTTTG CTCGGAGACT CCTCAGATCT GGAAACAGTG TGGTCCTTCC CATGCTGTAT    3044

TCTGAAAAGA TCTCATATGG ATGTTGTGCT CTGAGCACCA CAGATGTGAT CTGCAGCTCG    3104

TTTCTGAAAT GATGGAGTTC ATGGTGATCA GTGTGAGACT GGCCTCTCCC AGCAGGTTAA    3164

AAATGGAGTT TTAAATTATA CTGTAGCTGA CAGTACTTCT GATTTATAT TTATTTAGTC     3224

TGAGTTGTAG AACTTTGCAA TCTAAGTTTA TTTTTTGTAA CCTAATAATT CATTGGTGC     3284

TGGTCTATTG ATTTTTGGGG GTAAACAATA TTATTCTTCA GAAGGGGACC TACTTCTTCA    3344

TGGAAGAAT TACTTTTATT CTCAAACTAC AGAACAATGT GCTAAGCAGT GCTAAATTGT     3404

TCTCATGAAG AAAACAGTCA CTGCATTTAT CTCTGTAGGC CTTTTTTCAG AGAGGCCTTG    3464
```

Figure 2-9

```
TCTAGATTTT TGCCAGCTAG GCTACTGCAT GTCTTAGTGT CAGGCCTTAG GAAAGTGCCA   3524
CGCTCTGCAC TAAAGATATC AGAGCTCTTG GTGTTACTTA GACAAGAGTA TGAGCAAGTC   3584
GGACCTCTCA GAGTGTGGGA ACACAGTTTT GAAAGAAAAA CCATTTCTCT AAGCCAATTT   3644
TCTTTAAAGA CATTTTAACT TATTTAGCTG AGTTCTAGAT TTTCGGGTA AACTATCAAA    3704
TCTGTATATG TTGTAATAAA GTGTCTTATG CTAGGAGTTT ATTCAAAGTG TTTAAGTAAT   3764
AAAGGACTC AAATTACAC TGATAAAATA CTCTAGCTTG GGCCAGAGAA GACAGTGCTC     3824
ATTAGCGTTG TCCAGGAAAC CCTGCTTGCT TGCCAAGCCT AATGAAGGGA AAGTCAGCTT   3884
TCAGAGCCAA TGATGGAGGC CACATGAATG GCCCTGGAGC TGTGTGCCTT GTTCTGTGGC   3944
CAGGAGCTTG GTGACTGAAT CATTACGGG CTCCTTTGAT GGACCCATAA AAGCTCTTAG    4004
CTTCCTCAGG GGGTCAGCAG AGTTGTTGAA TCTTAATTTT TTTTTAATG TACCAGTTTT    4064
GTATAAATAA TAATAAAGAG CTCCTTATTT TGTATTCTAT CTAATGCTTC GAGTTCAGTC   4124
TTGGGAAGCT GACATCTCAT GTAGAAGATG GACTCTGAAA GACATTCCAA GAGTGCAGCG   4184
GCATCATGGG AGCCTCTTAG TGATTGTGTG TCAGTATTAT TGTGGAAGAT TGACTTTGCT   4244
TTTGTATGTG AAGTTTCAGA TTGCTCCCTCT TGTGACTTTT TAGCCAGTAA CATTTTATTT  4304
```

Figure 2-10

```
ACCTGAGCTT GTCATGGAAG TGGCAGTGAA AAGTATTGAG TATTCATGCT GGTGACTGTA    4364

ACCAATGTCA TCTTGCTAAA AACTCATGTT TTGTACAATT ACTAAATTGT ATACATTTTG    4424

TTATAGAATA CTTTTTCCAG TTGAGTAAAT TATGAAAGGA AGTTAACATT AACAGGTGTA    4484

AGCGGTGGCT TTTTAAAAT GAAGGATTAA CCCTAAGCCC GAGACCCAGA AGCTAGCAAA     4544

GTCTGGCAGA GTGGTAAACT GTCCTGCTGG GGCCATCCAA TCATCTCTCT CCATTACACT    4604

TTCTAACTTT GCAGCATTGG TGCTGGCCAG TGTATTGTTT CATTGATCTT CCTTACGCTT    4664

AGAGGGTTTG ATTGGTTCAG ATCTATAATC TCAGCCACAT TGTCTTGGTA TCAGCTGGAG    4724

AGAGTTAAGA GGAAGGGAAA ATAAAGTTCA GATAGCCAAA ACAC                     4768
```

Figure 2-11

```
TTTATTAACT TATTTTTTC TTCTTTCTAC CCAATTCTAG TCAGGAAAAG ACTAAGGGCT          60

GGAACATAGT GTATCATTGT CTAATTGTTG ATACAAAGTA GATAAATACA TAAAACAAGC         120

ATG CCG CCG CTA TTC AAG GGA CTG AAA CAG ATG GCA AAG CCA ATT GCC          168
Met Pro Pro Leu Phe Lys Gly Leu Lys Gln Met Ala Lys Pro Ile Ala
  1               5                  10                 15

TAT GTT TCA AGA TTT TCG GCG AAA CGA CCA ATT CAT ATA ATA CTT TTT          216
Tyr Val Ser Arg Phe Ser Ala Lys Arg Pro Ile His Ile Ile Leu Phe
         20                  25                 30

TCT CTA ATC ATA TCC GCA TTC GCT TAT CTA TCC GTC ATT CAG TAT TAC          264
Ser Leu Ile Ile Ser Ala Phe Ala Tyr Leu Ser Val Ile Gln Tyr Tyr
     35                  40                 45

TTC AAT GGT TGG CAA CTA GAT TCA AAT AGT GTT TTT GAA ACT GCT CCA          312
Phe Asn Gly Trp Gln Leu Asp Ser Asn Ser Val Phe Glu Thr Ala Pro
 50                  55                 60

AAT AAA GAC TCC AAC ACT CTA TTT CAA GAA TGT TCC CAT TAC TAC AGA          360
Asn Lys Asp Ser Asn Thr Leu Phe Gln Glu Cys Ser His Tyr Tyr Arg
         65                  70                 75                 80

GAT TCC TCT CTA GAT GGT TGG GTA TCA ATC ACC GCG CAT GAA GCT AGT          408
Asp Ser Ser Leu Asp Gly Trp Val Ser Ile Thr Ala His Glu Ala Ser
             85                  90                 95
```

Figure 3-1

```
GAG TTA CCA GCC CCA CAC CAT TAC TAT CTA TTA AAC CTG AAC TTC AAT       456
Glu Leu Pro Ala Pro His His Tyr Tyr Leu Leu Asn Leu Asn Phe Asn
        100                 105                 110

AGT CCT AAT GAA ACT GAC TCC ATT CCA GAA CTA GCT AAC ACG GTT TTT       504
Ser Pro Asn Glu Thr Asp Ser Ile Pro Glu Leu Ala Asn Thr Val Phe
            115                 120                 125

GAG AAA GAT AAT ACA AAA TAT CTG CAA GAA GAT CTC AGT GTT TCC           552
Glu Lys Asp Asn Thr Lys Tyr Ile Leu Gln Glu Asp Leu Ser Val Ser
        130                 135                 140

AAA GAA ATT TCT ACT TCT GAT GGA ACG AAA TGG TTA AGA AGT GAC           600
Lys Glu Ile Ser Thr Ser Asp Gly Thr Lys Trp Leu Arg Ser Asp
145                 150                 155                 160

AGA AAA AGT CTT TTC GAC GTA AAG ACG TTA GCA TAT TCT CTC TAC GAT       648
Arg Lys Ser Leu Phe Asp Val Lys Thr Leu Ala Tyr Ser Leu Tyr Asp
        165                 170                 175

GTA TTT TCA GAA CTT AAT GTA ACC CAA GCA GAC CCG TTT GAC GTC CTT ATT   696
Val Phe Ser Glu Leu Asn Val Thr Gln Ala Asp Pro Phe Asp Val Leu Ile
            180                 185                 190

ATG GTT ACT GCC TAC CTA ATG ATG TTC TAC ACC ATA TTC GGC CTC TTC       744
Met Val Thr Ala Tyr Leu Met Met Phe Tyr Thr Ile Phe Gly Leu Phe
        195                 200                 205
```

Figure 3-2

```
AAT GAC ATG AGG AAG ACC GGG TCA AAT TTT TGG TTG AGC GCC TCT ACA    792
Asn Asp Met Arg Lys Thr Gly Ser Asn Phe Trp Leu Ser Ala Ser Thr
210                 215                 220

GTG GTC AAT TCT GCA TCA CTT TTC TTA GCA TTG TAT GTC ACC CAA        840
Val Val Asn Ser Ala Ser Leu Phe Leu Ala Leu Tyr Val Thr Gln
225                 230                 235                 240

TGT ATT CTA GGC AAA GAA GTT TCC GCA TTA ACT CTT TTT GAA GGT TTG    888
Cys Ile Leu Gly Lys Glu Val Ser Ala Leu Thr Leu Phe Glu Gly Leu
                245                 250                 255

CCT TTC ATT GTA GTT GTT GTT GGT TTC AAG CAC AAA ATC AAG ATT GCC    936
Pro Phe Ile Val Val Val Val Gly Phe Lys His Lys Ile Lys Ile Ala
            260                 265                 270

CAG TAT GCC CTG GAG AAA TTT GAA AGA GTC GGT TTA TCT AAA AGG ATT    984
Gln Tyr Ala Leu Glu Lys Phe Glu Arg Val Gly Leu Ser Lys Arg Ile
275                 280                 285

ACT ACC GAT GAA ATC GTT TTT GAA TCC GTG AGC GAA GAG GGT GGT CGT   1032
Thr Thr Asp Glu Ile Val Phe Glu Ser Val Ser Glu Glu Gly Gly Arg
        290                 295                 300

TTG ATT CAA GAC CAT TTG CTT TGT ATT TTT GCC TTT ATC GGA TGC TCT   1080
Leu Ile Gln Asp His Leu Leu Cys Ile Phe Ala Phe Ile Gly Cys Ser
305                 310                 315                 320
```

Figure 3-3

| | | | | | | | | | | | | | | | |
|---|---|---|---|---|---|---|---|---|---|---|---|---|---|---|---|
| ATG | TAT | GCT | CAC | CAA | TTG | AAG | ACT | TTG | ACA | AAC | TTC | TGC | ATA | TTA | TCA | 1128
| Met | Tyr | Ala | His | Gln | Leu | Lys | Thr | Leu | Thr | Asn | Phe | Cys | Ile | Leu | Ser |
| | | | 325 | | | | | 330 | | | | | 335 | | |
| GCA | TTT | ATC | CTA | ATT | TTT | GAA | TTG | ATT | TTA | ACT | CCT | ACA | TTT | TAT | TCT | 1176
| Ala | Phe | Ile | Leu | Ile | Phe | Glu | Leu | Ile | Leu | Thr | Pro | Thr | Phe | Tyr | Ser |
| | | | 340 | | | | | 345 | | | | | 350 | | |
| GCT | ATC | TTA | GCG | CTT | AGA | CTG | GAA | ATG | AAT | GTT | ATC | CAC | AGA | TCT | ACT | 1224
| Ala | Ile | Leu | Ala | Leu | Arg | Leu | Glu | Met | Asn | Val | Ile | His | Arg | Ser | Thr |
| | | | 355 | | | | | 360 | | | | | 365 | | |
| ATT | ATC | AAG | CAA | ACA | TTA | GAA | GAC | GGT | GTT | GTT | CCA | TCT | TCT | ACA | GCA | 1272
| Ile | Ile | Lys | Gln | Thr | Leu | Glu | Asp | Gly | Val | Val | Pro | Ser | Ser | Thr | Ala |
| | | | 370 | | | | | 375 | | | | | 380 | | |
| AGA | ATC | ATT | TCT | AAA | GCA | GAA | AAG | AAA | TCC | GTA | TCT | TCT | TTC | TTA | AAT | 1320
| Arg | Ile | Ile | Ser | Lys | Ala | Glu | Lys | Lys | Ser | Val | Ser | Phe | Leu | Asn |
| | 385 | | | | | 390 | | | | | 395 | | | | 400 |
| CTC | AGT | GTG | GTT | GTC | ATT | ATC | ATG | AAA | CTC | TCT | GTC | ATA | CTG | TTG | TTT | 1368
| Leu | Ser | Val | Val | Val | Ile | Ile | Met | Lys | Leu | Ser | Val | Ile | Leu | Leu | Phe |
| | | | 405 | | | | | 410 | | | | | 415 | | |
| GTT | TTC | ATC | AAC | TTT | TAT | AAC | TTT | GGT | GCA | AAT | TGG | GTC | AAT | GAT | GCC | 1416
| Val | Phe | Ile | Asn | Phe | Tyr | Asn | Phe | Gly | Ala | Asn | Trp | Val | Asn | Asp | Ala |
| | | | 420 | | | | | 425 | | | | | 430 | | |

Figure 3-4

```
TTC AAT TCA TTG TAC TTC GAT AAG GAA CGT GTT TCT CTA CCA GAT TTT   1464
Phe Asn Ser Leu Tyr Phe Asp Lys Glu Arg Val Ser Leu Pro Asp Phe
        435                 440                 445

ATT ACC TCG AAT GCC TCT GAA AAC TTT AAA GAG CAA GCT ATT GTT AGT   1512
Ile Thr Ser Asn Ala Ser Glu Asn Phe Lys Glu Gln Ala Ile Val Ser
        450                 455                 460

GTC ACC CCA TTA TAT TAC AAA CCC ATT AAG TCC TAC CAA CGC ATT       1560
Val Thr Pro Leu Tyr Tyr Lys Pro Ile Lys Ser Tyr Gln Arg Ile
        465                 470                 475           480

GAG GAT ATG GTT CTT CTA TTG CTT CGT AAT GTC AGT GTT GCC ATT CGT   1608
Glu Asp Met Val Leu Leu Leu Leu Arg Asn Val Ser Val Ala Ile Arg
        485                 490                 495

GAT AGG TTC GTC AGT AAA TTA GTT CTT TCC GCC TTA GTA TGC AGT GCT   1656
Asp Arg Phe Val Ser Lys Leu Val Leu Ser Ala Leu Val Cys Ser Ala
        500                 505                 510

GTC AAT GTG TAT TTA TTG AAT GCT GCT AGA ATT CAT ACC AGT TAT       1704
Val Ile Asn Val Tyr Leu Leu Asn Ala Ala Arg Ile His Thr Ser Tyr
        515                 520                 525

ACT GCA GAC CAA TTG GTG AAA ACT GAA GTC ACC AAG AAG TCT TTT ACT   1752
Thr Ala Asp Gln Leu Val Lys Thr Glu Val Thr Lys Lys Ser Phe Thr
        530                 535                 540
```

Figure 3-5

| GCT Ala 545 | CCT Pro | GTA Val | CAA Gln | AAG Lys | GCT Ala 550 | TCT Ser | ACA Thr | CCA Pro | GTT Val | TTA Leu 555 | ACC Thr | AAT Asn | AAA Lys | ACA Thr | GTC Val 560 | 1800 |

| ATT Ile | TCT Ser | GGA Gly | TCG Ser | AAA Lys 565 | GTC Val | AAA Lys | AGT Ser | TTA Leu | TCA Ser 570 | TCT Ser | GCG Ala | CAA Gln | TCG Ser | AGC Ser 575 | TCA Ser | 1848 |

| TCA Ser | GGA Gly | CCT Pro | TCA Ser | TCA Ser 580 | TCT Ser | AGT Ser | GAG Glu | GAA Glu | GAT Asp 585 | GAT Asp | TCC Ser | CGC Arg | GAT Asp | ATT Ile 590 | GAA Glu | 1896 |

| AGC Ser | TTG Leu | GAT Asp | AAG Lys | AAA Lys 595 | ATA Ile | CGT Arg | CCT Pro | TTA Leu | GAA Glu 600 | GAA Glu | TTA Leu | GAA Glu | GCA Ala | TTA Leu 605 | TTA Leu | 1944 |

| AGT Ser | AGT Ser | GGA Gly | AAT Asn | ACA Thr 610 | AAA Lys | CAA Gln | TTG Leu | AAC Asn | AAA Lys 615 | AAA Lys | GAG Glu | GTC Val | GCT Ala | GCC Ala 620 | TTG Leu | 1992 |

| GTT Val | ATT Ile | CAC His | GGT Gly | AAG Lys 625 | TTA Leu | CCT Pro | TTG Leu | TAC Tyr | GCT Ala 630 | TTG Leu | GAG Glu | AAA Lys | TTA Leu | GGT Gly 635 | GGT Gly | 2040 |

| GAT Asp | ACT Thr | ACG Thr | AGA Arg | GCG Ala 640 | GTT Val | GCG Ala | GTA Val | CGT Arg | AGG Arg 645 | AAG Lys | GCT Ala | CTT Leu | TCA Ser | ATT Ile 650 | TTG Leu | 2088 |

Figure 3-6

| | | | | | | | | | | | | | | | |
|---|---|---|---|---|---|---|---|---|---|---|---|---|---|---|---|
| GCA | GAA | GCT | CCT | GTA | TTA | GCA | TCT | GAT | CGT | TTA | CCA | TAT | AAA | AAT | TAT |
| Ala | Glu | Ala | Pro | Val | Leu | Ala | Ser | Asp | Arg | Leu | Pro | Tyr | Lys | Asn | Tyr |
| | | | 660 | | | | | 665 | | | | | 670 | | | 2136 |

| GAC | TAC | GAC | CGC | GTA | TTT | GGC | GCT | TGT | TGT | GAA | AAT | GTT | ATA | GGT | TAC |
|---|---|---|---|---|---|---|---|---|---|---|---|---|---|---|---|
| Asp | Tyr | Asp | Arg | Val | Phe | Gly | Ala | Cys | Cys | Glu | Asn | Val | Ile | Gly | Tyr |
| | | 675 | | | | | 680 | | | | | 685 | | | | 2184 |

| ATG | CCT | TTG | CCC | GTT | GGT | GTT | ATA | GGC | CCC | TTG | GTT | ATC | GAT | GGT | ACA |
|---|---|---|---|---|---|---|---|---|---|---|---|---|---|---|---|
| Met | Pro | Leu | Pro | Val | Gly | Val | Ile | Gly | Pro | Leu | Val | Ile | Asp | Gly | Thr |
| 690 | | | | | 695 | | | | | 700 | | | | | | 2232 |

| TCT | TAT | CAT | ATA | CCA | ATG | GCA | ACT | ACA | GAG | GGT | TGT | TTG | GTA | GCT | TCT |
|---|---|---|---|---|---|---|---|---|---|---|---|---|---|---|---|
| Ser | Tyr | His | Ile | Pro | Met | Ala | Thr | Thr | Glu | Gly | Cys | Leu | Val | Ala | Ser |
| 705 | | | | | 710 | | | | | 715 | | | | | 720 | 2280 |

| GCC | ATG | CGT | GGC | TGT | AAG | GCA | ATC | AAT | GCT | GGC | GGT | GGT | GCA | ACA | ACT |
|---|---|---|---|---|---|---|---|---|---|---|---|---|---|---|---|
| Ala | Met | Arg | Gly | Cys | Lys | Ala | Ile | Asn | Ala | Gly | Gly | Gly | Ala | Thr | Thr |
| | | | | 725 | | | | | 730 | | | | | 735 | | 2328 |

| GTT | TTA | ACT | AAG | GAT | GGT | ATG | ACA | AGA | GGC | CCA | GTA | GTC | CGT | TTC | CCA |
|---|---|---|---|---|---|---|---|---|---|---|---|---|---|---|---|
| Val | Leu | Thr | Lys | Asp | Gly | Met | Thr | Arg | Gly | Pro | Val | Val | Arg | Phe | Pro |
| | | | 740 | | | | | 745 | | | | | 750 | | | 2376 |

| ACT | TTG | AAA | AGA | TCT | GGT | GCC | TGT | AAG | ATA | TGG | TTA | GAC | TCA | GAA | GAG |
|---|---|---|---|---|---|---|---|---|---|---|---|---|---|---|---|
| Thr | Leu | Lys | Arg | Ser | Gly | Ala | Cys | Lys | Ile | Trp | Leu | Asp | Ser | Glu | Glu |
| | | 755 | | | | | 760 | | | | | 765 | | | | 2424 |

Figure 3-7

| | | | | | | | | | | | | | | | |
|---|---|---|---|---|---|---|---|---|---|---|---|---|---|---|---|
| GGA | CAA | AAC | GCA | ATT | AAA | GCT | TTT | AAC | TCT | ACA | TCA | AGA | TTT | GCA | 2472 |
| Gly | Gln | Asn | Ala | Ile | Lys | Ala | Phe | Asn | Ser | Thr | Ser | Arg | Phe | Ala | |
| 770 | | | | | 775 | | | | | 780 | | | | | |
| CGT | CTG | CAA | CAT | ATT | CAA | ACT | TGT | CTA | GCA | GGA | GAT | TTA | CTC | TTC | ATG | 2520 |
| Arg | Leu | Gln | His | Ile | Gln | Thr | Cys | Leu | Ala | Gly | Asp | Leu | Leu | Phe | Met |
| 785 | | | | 790 | | | | | 795 | | | | | 800 | |
| AGA | TTT | AGA | ACA | ACT | GGT | GAC | GCA | ATG | GGT | ATG | AAT | ATG | ATT | TCT | 2568 |
| Arg | Phe | Arg | Thr | Thr | Gly | Asp | Ala | Met | Gly | Met | Asn | Met | Ile | Ser | |
| | | 805 | | | | | 810 | | | | | 815 | | | |
| AAA | GGT | GTC | GAA | GTT | GTC | TCC | GTT | TAC | TCA | TTA | AAG | CAA | ATG | GTA | GAA | GAG | TAT | GGC | TGG | 2616 |
| Lys | Gly | Val | Glu | Val | Val | Ser | Val | Tyr | Ser | Leu | Lys | Gln | Met | Val | Glu | Glu | Tyr | Gly | Trp |
| | 820 | | | | | | 825 | | | | | | 830 | | | | | | |
| GAA | GAT | ATG | GAG | GTT | GTC | TCC | GTT | TCT | GGT | AAC | TAC | TGT | ACC | GAC | AAA | 2664 |
| Glu | Asp | Met | Glu | Val | Val | Ser | Val | Ser | Gly | Asn | Tyr | Cys | Thr | Asp | Lys |
| | 835 | | | | | 840 | | | | | 845 | | | | |
| AAA | CCA | GCT | GCC | ATC | AAC | TGG | ATC | GAA | GGT | CGT | GGT | AAG | AGT | GTC | GTC | 2712 |
| Lys | Pro | Ala | Ala | Ile | Asn | Trp | Ile | Glu | Gly | Arg | Gly | Lys | Ser | Val | Val |
| 850 | | | | | 855 | | | | | 860 | | | | | |
| GCA | GAA | GCT | ACT | ATT | CCT | GGT | GAT | GTT | GTC | AGA | GTG | TTA | AAA | AGT | 2760 |
| Ala | Glu | Ala | Thr | Ile | Pro | Gly | Asp | Val | Val | Arg | Val | Leu | Lys | Ser | |
| 865 | | | | | 870 | | | | | 875 | | | | | 880 |

Figure 3-8

| | | | | | | | | | | | | | | | |
|---|---|---|---|---|---|---|---|---|---|---|---|---|---|---|---|
| GAT | GTT | TCC | GCA | TTG | GTT | GAG | TTG | AAC | ATT | GCT | AAG | AAT | TTG | GTT | GGA |
| Asp | Val | Ser | Ala | Leu | Val | Glu | Leu | Asn | Ile | Ala | Lys | Asn | Leu | Val | Gly |
| | | | | 885 | | | | | 890 | | | | | 895 | 2808 |
| TCT | GCA | ATG | GCT | GTT | GGT | GGA | TCT | GTT | TTC | TTG | GCA | CAT | GCA | GCT | AAT |
| Ser | Ala | Met | Ala | Val | Gly | Gly | Ser | Val | Phe | Leu | Ala | His | Ala | Ala | Asn |
| | | 900 | | | | 905 | | | | 910 | | | | | 2856 |
| TTA | GTG | ACA | GCT | GTT | TTC | TTG | GCA | TTA | GGA | CAA | GAT | CCT | GCA | CAA | AAT |
| Leu | Val | Thr | Ala | Val | Phe | Leu | Ala | Leu | Gly | Gln | Asp | Pro | Ala | Gln | Asn |
| | | 915 | | | | 920 | | | | 925 | | | | | 2904 |
| GTT | GAA | AGT | TCC | AAC | TGT | ATA | ACA | TTG | ATG | AAA | GAA | GTG | GAC | GGT | GAT |
| Val | Glu | Ser | Ser | Asn | Cys | Ile | Thr | Leu | Met | Lys | Glu | Val | Asp | Gly | Asp |
| | 930 | | | | 935 | | | | 940 | | | | | | 2952 |
| TTG | AGA | ATT | TCC | GTA | TCC | ATG | CCA | TCC | ATC | GAA | GTA | GGT | ACC | ATC | GGT |
| Leu | Arg | Ile | Ser | Val | Ser | Met | Pro | Ser | Ile | Glu | Val | Gly | Thr | Ile | Gly |
| 945 | | | | | 950 | | | | 955 | | | | | 960 | 3000 |
| GGT | ACT | GTT | CTA | GAA | CCA | CAA | GGT | GCC | ATG | TTG | GAC | TTA | TTA | GGT | |
| Gly | Thr | Val | Leu | Glu | Pro | Gln | Gly | Ala | Met | Leu | Asp | Leu | Leu | Gly | |
| | 965 | | | | | 970 | | | | 975 | | | | | 3048 |
| GTA | AGA | GGC | CCG | CAT | GCT | ACC | GCT | CCT | GGT | ACC | AAC | GCA | CGT | CAA | TTA |
| Val | Arg | Gly | Pro | His | Ala | Thr | Ala | Pro | Gly | Thr | Asn | Ala | Arg | Gln | Leu |
| | | 980 | | | | 985 | | | | 990 | | | | | 3096 |

Figure 3-9

```
GCA AGA ATA GTT GCC TGT GCC GTC TTG GCA GGT GAA TTA TCC TTA TGT    3144
Ala Arg Ile Val Ala Cys Ala Val Leu Ala Gly Glu Leu Ser Leu Cys
        995                         1000                     1005

GCT GCC CTA GCA GCC GGC CAT TTG GTT CAA AGT CAT ATG ACC CAC AAC    3192
Ala Ala Leu Ala Ala Gly His Leu Val Gln Ser His Met Thr His Asn
        1010                        1015                    1020

AGG AAA CCT GCT GAA CCA ACA AAA CCT AAC AAT TTG GAC GCC ACT GAT    3240
Arg Lys Pro Ala Glu Pro Thr Lys Pro Asn Asn Leu Asp Ala Thr Asp
        1025                        1030                    1035                    1040

ATA AAT CGT TTG AAA GAT GGG TCC GTC ACC TGC ATT AAA TCC             3282
Ile Asn Arg Leu Lys Asp Gly Ser Val Thr Cys Ile Lys Ser
        1045                        1050

TAAACTTAGT CATACGTCAT TGGTATTCTC TTGAAAAGA AGCACAACAG CACCATGTGT   3342

TACGTAAAAT ATTTACTT                                                 3360
```

Figure 3-10

METHOD AND COMPOSITION FOR INCREASING STEROL ACCUMULATION IN HIGHER PLANTS

TECHNICAL FIELD

The present invention relates to methods and compositions for increasing the accumulation of sterols in higher plants, and more particularly to increasing sterol accumulation by increasing the number of copies of a gene encoding a polypeptide having HMG-CoA reductase activity.

BACKGROUND OF THE INVENTION

Mevalonate ($C_6H_{11}O_4$) is the metabolic precursor of a vast array of compounds vital for cell and organism viability. In plants, the major endproducts derived from mevalonate are the sterols and other isoprenoids. (see FIG. 1).

Exemplary plant isoprenoids include the terpenes (volatile $C_{10}$ and $C_{15}$ compounds giving rise to fragrances of many plants) the carotenoids ($C_{40}$ compounds giving rise to the color of many plants) and polymers such as natural rubber.

Free sterols are constituents of virtually all eukaryotic membranes. The most abundant sterols of vascular plants are campesterol, 24-methylcholesterol, sitosterol and stigmasterol.

Mevalonate is formed from the reduction of 3-hydroxy-3-methylglutaryl coenzyme A (HMG-CoA). The reduction of HMG-CoA to mevalonate is catalyzed by the enzyme HMG-CoA reductase.

The HMG-CoA reductase enzymes of animals and yeasts are integral membrane glycoproteins of the endoplasmic reticulum. The intact enzyme comprises three regions: a catalytic region, containing the active site of the enzyme, a membrane binding region, anchoring the enzyme to the endoplasmic reticulum and a linker region, joining the catalytic and membrane binding regions of the enzymes. The membrane binding region occupies the $NH_2$-terminal portion of the intact protein, whereas the catalytic region occupies the COOH-terminal portion of the protein, with the linker region constituting the remaining portion. Basson, M. E. et al., *Mol. Cell Biol.*, 8(9):3797-3808 (1988). At present, the subcellular localization of HMG-CoA reductase in plants is not known. Russell, D. W. et al., *Current Topics in Plant Biochemistry*, Vol. 4, ed. by D. D. Randall et al., Univ. of Missouri (1985).

The activity of HMG-CoA reductase in animals and yeasts is known to be subject to feedback inhibition by sterols. Such feedback inhibition requires the presence of the membrane binding region of the enzyme. See, e.g., Gil, G. et al., *Cell*, 41: 249-258(1985); Bard, M. and Downing, J. F. *Journal of General Microbiology*, 125:415-420(1981).

Given that mevalonate is the precursor for sterols and other isoprenoids, it might be expected that increases in the amount or activity of HMG-CoA reductase would lead to increases in the accumulation of both sterols and other isoprenoids. In yeasts and non-photosynthetic microorganisms, increases in HMG-CoA reductase activity are not associated with predictable increases in the production of sterols or other isoprenoids.

In mutant strains of the yeast *Saccharomyces cerevisiae* (*S. cerevisiae*) having abnormally high levels of HMG-CoA reductase activity, the production of two sterols, 4,14-dimethylzymosterol and 14-methylfecosterol, is markedly increased above normal. Downing, J. F. et al., *Biochemical and Biophysical Research Communications*, 94(3): 974-979(1980).

When HMG-CoA reductase activity was increased by illumination in non-photosynthetic microorganisms, isoprenoid (carotenoid), but not sterol (ergosterol), synthesis was enhanced. Tada, M. and Shiroishi, M. *Plant and Cell Physiology*, 23(4): 615-621(1982). There are no studies reporting the effects of such increases in HMG-CoA reductase activity in plants.

SUMMARY OF THE INVENTION

The present invention provides a method of increasing sterol accumulation in a plant that comprises increasing the copy number of a structural gene that encodes a polypeptide having HMG-CoA reductase activity, thereby increasing the activity of that enzyme relative to the activity in the native plant. A polypeptide having HMG-CoA reductase activity includes an intact HMG-CoA reductase enzyme as well as an active, truncated HMG-CoA reductase enzyme. In a preferred embodiment, an active, truncated HMG-CoA reductase enzyme comprises the catalytic and linker regions, but not the membrane binding region, of hamster HMG-CoA reductase.

The copy number of a gene encoding a polypeptide having HMG-CoA reductase activity is increased by transforming a plant with a recombinant DNA molecule comprising a vector operatively linked to an exogenous DNA segment that encodes a polypeptide having HMG-CoA reductase activity, and a promoter suitable for driving the expression of said polypeptide in the plant. A preferred recombinant DNA molecule is plasmid HMGRΔ227-pKYLX71.

The promoter is preferably a promoter whose regulatory function is substantially unaffected by the level of sterol in the transformed plant. A preferred promoter is the CaMV 35S promoter. In particularly preferred practice, the level of an accumulated sterol, cycloartenol, is particularly enhanced.

The present invention still further provides a method of increasing pest resistance in plants. In this method, the copy number of a structural gene that encodes a polypeptide having HMG-CoA reductase activity is increased over that of the native plant, as discussed before.

A transformed plant having an increased copy number of a structural gene that encodes a polypeptide having HMG-CoA reductase activity is also contemplated. Such a plant exhibits a higher total sterol, particularly cycloartenol, content than does a native, untransformed plant. Such a transformed plant also exhibits resistance to pests such as hormworm, relative to an untransformed plant, native plant.

The present invention further provides a plant seed capable of germinating into a plant that over accumulates sterol relative to a native, untransformed plant of the same strain and mutants, recombinants, genetically engineered derivatives thereof and hybrids derived therefrom.

BRIEF DESCRIPTION OF THE DRAWINGS

In the drawings forming a portion of this disclosure.

*Current Topics in Plant Biochemistry*, Vol. 4, ed. by D. D. Randall et al., Univ. of Missouri (1985).

FIGS. 2-1 to 2-11, shown as eleven panels designated FIG. 2-1 and 2-11, is a composite nucleotide sequence of the cDNA corresponding to the mRNA for hamster HMG-CoA reductase (SEQ. ID No. 1), and the predicted amino acid sequence (SEQ. ID No. 2) of the protein as published by Chin, D. J. et al., *Nature*, 308:613–617 (1984). Nucleotides are numbered (left-hand side) in the 5' to 3' direction. Position 1 corresponds to the first nucleotide of the ATG triplet coding for the initiator methionine. The predicted amino acid sequence is shown below the nucleotide sequence. The amino acid residues are numbered (right-hand side) beginning with the initiator methionine.

FIGS. 3-1, 3-2, 3-3 and 3-4 to 3-10, shown as ten panels designated FIG. 3-1 to 3-10, is the nucleotide base sequence (SEQ. ID No. 3) and derived amino acid residue sequence (SEQ. ID No. 4) for *S. cerevisiae* HMG-CoA reductase 1 published by Basson, M. E. et al., *Mol. Cell Biol.*, 8(9):3797–3808 (1988). Nucleotides are shown and numbered as discussed for FIG. 2 as are the derived amino acid residues.

Figure 1:
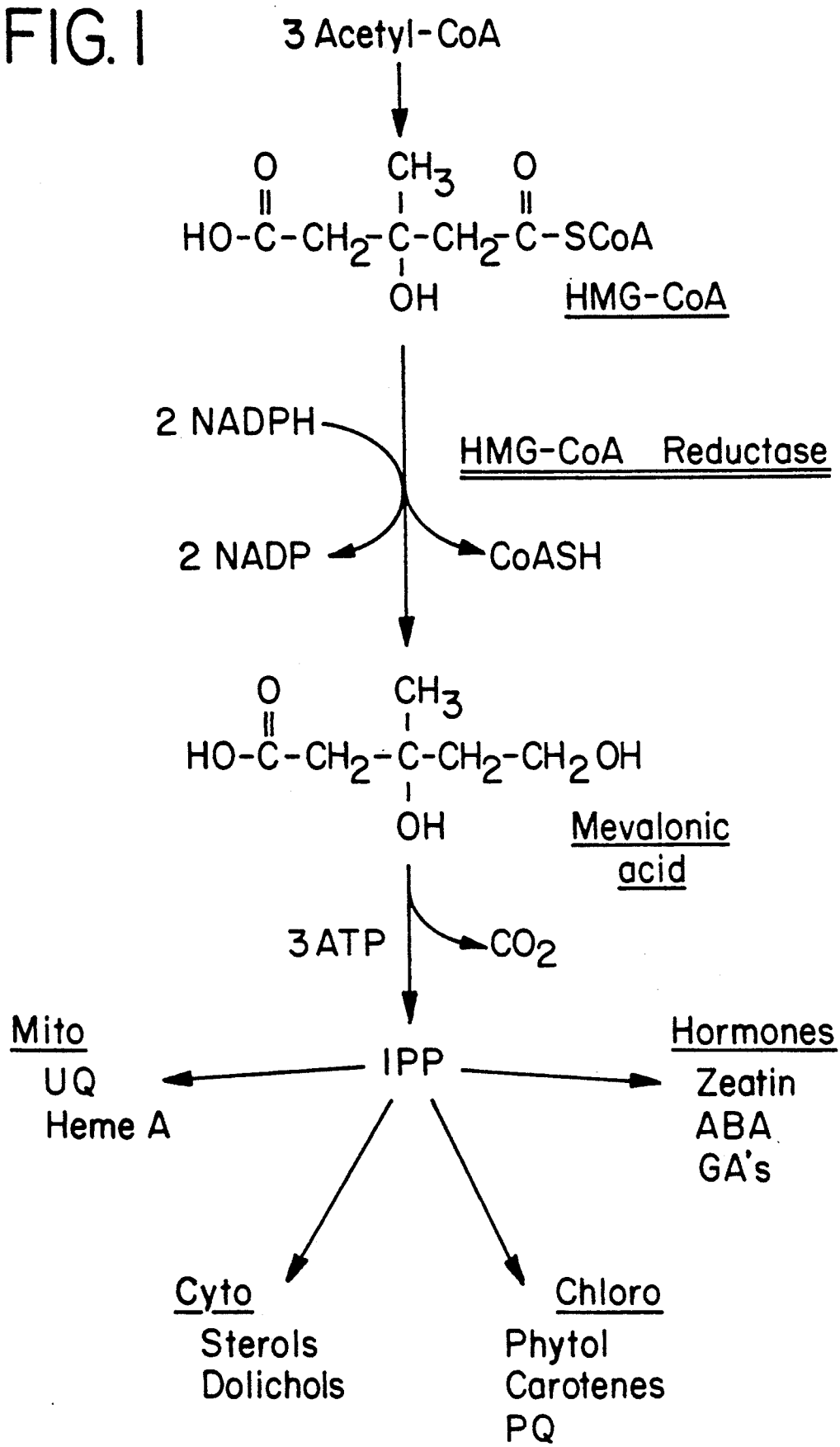
FIG. 1 is a schematic representation of the metabolism of acetyl coenzyme A to sterols and other isoprenoids in plants as published by Russell, D. W. et al.
Figures 4, 5:
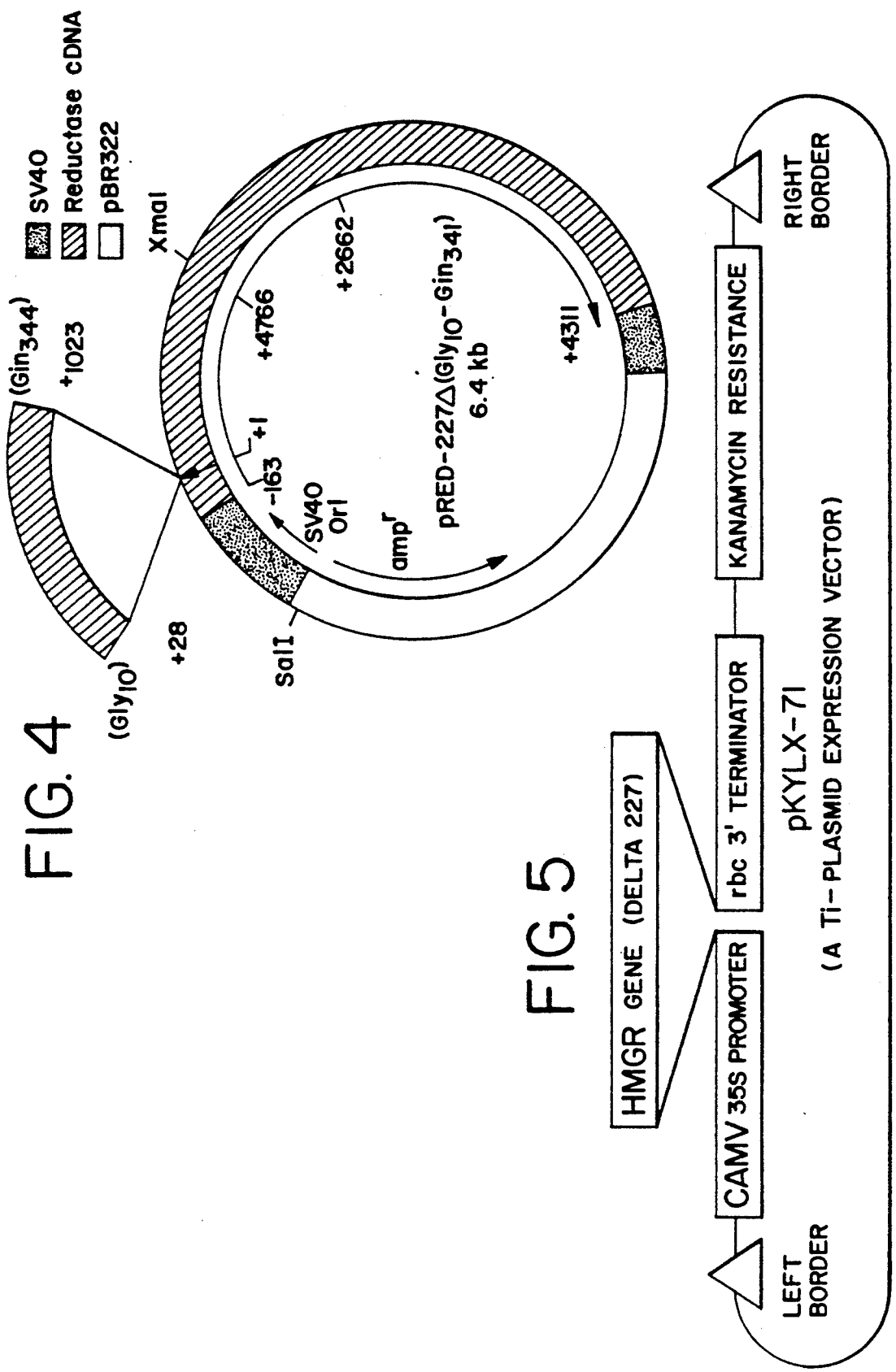

FIG. 4 is a schematic drawing showing the structure of a plasmid (pRed-227Δ) used to insert a truncated hamster gene encoding for hamster HMG-CoA reductase into cells lacking such hamster enzyme. Base pairs of the reductase coding sequence (nucleotides 28 to 1023) that encode amino acids 10 to 341 have been deleted and are shown externally of the plasmid. The hatched area denotes the reductase cDNA sequence portion of the plasmid. The reductase cDNA initiator methionine codon (nucleotide 1) and terminator codon (nucleotide 2662) are indicated, as are other features of the plasmid.

FIG. 5 is a schematic restriction map of plasmid HMGRΔ227-pKYLX71 used to transform the plants of the present invention.

DETAILED DESCRIPTION OF THE INVENTION

I. Definitions

The following words and phrases have the meanings set forth below.

Expression: The combination of intracellular processes, including transcription and translation undergone by a structural gene to produce a polypeptide.

Expression vector: A DNA sequence that forms control elements that regulate expression of structural genes when operatively linked to those genes.

Operatively linked: A structural gene is covalently bonded in correct reading frame to another DNA (or RNA as appropriate) segment, such as to an expression vector so that the structural gene is under the control of the expression vector.

Promoter: A recognition site on a DNA sequence or group of DNA sequences that provide an expression control element for a structural gene and to which RNA polymerase specifically binds and initiates RNA synthesis (transcription) of that gene.

Recombinant DNA molecule: A hybrid DNA sequence comprising at least two nucleotide sequences not normally found together in nature.

Structural gene: A DNA sequence that is expressed as a polypeptide, i.e., an amino acid residue sequence.

Vector: A DNA molecule capable of replication in a cell and/or to which another DNA segment can be operatively linked so as to bring about replication of the attached segment. A plasmid is an exemplary vector.

II. The Invention

The present invention relates to compositions and methods for increasing sterol accumulation in plants, as well as to the plants that exhibit increased sterol accumulation relative to a native variety of the plant. Plants contemplated by this invention are the vascular, multicellular higher plants. Such higher plants will hereinafter be usually referred to simply as "plants". Exemplary plants are tobacco, tomato, corn, carrot, soybean, cotton, barley, arabidopsis, guayule and petunia. A preferred plant is tobacco of the strain *Nicotiana tabacum* (*N. tabacum*).

A plant contemplated by this invention is transformed with an added structural gene that encodes a polypeptide having HMG-CoA reductase activity, that encoded polypeptide being expressed in the transformed plant. An untransformed plant that is a precursor to the transformed plant is referred to herein as a "native" plant. The native and transformed plants compared are of the same type such as siblings from the same seed pod, clones from the same parent, or plants of the same strain.

Sterol production in a plant of the present invention is increased by increasing the cellular activity of the enzyme HMG-CoA reductase, which enzyme catalyzes the conversion of 3-hydroxy-3-methylglutaryl Coenzyme A (HMG-CoA) to mevalonate. As used herein, "cellular activity" means the total catalytic activity of HMG-CoA reductase in a plant cell.

Cellular HMG-CoA reductase activity is increased by increasing the copy number of a gene encoding a polypeptide having HMG-CoA reductase catalytic activity. Expression of that encoded structural gene enhances the cellular activity of that enzyme.

The copy number is increased by transforming a plant cell with a recombinant DNA molecule comprising a vector operatively linked to an exogenous DNA segment that encodes a polypeptide having HMG-CoA reductase activity, and a promoter suitable for driving the expression of said polypeptide in said plant. Such a polypeptide includes intact as well as catalytically active, truncated HMG-CoA reductase proteins.

Thus, a transformed plant cell and plant have one or more added genes that encode a polypeptide having HMG-CoA reductase activity relative to a native, untransformed plant of the same type. As such, a transformed plant can be distinguished from a native plant by standard technology such as agarose separation of DNA fragments or mRNAs followed by transfer and appropriate blotting with DNA or RNA or by use of polymerase chain reaction technology, as are well known. Relative HMG-CoA reductase activity of the transformed and native plants or cell cultures therefrom can also be compared, with a relative activity of 1.5:1 for transformed:native showing transformation.

Sterol accumulation can also be used to distinguish between native and transformed plants. A transformed plant has at least about twice the total sterol content of a native plant where a single added gene is present.

A. Structural Genes

The present invention contemplates transforming a plant with a structural gene that encodes a polypeptide having HMG-CoA reductase activity. The HMG-CoA reductase enzymes of both animal and yeast cells comprise three distinct amino acid residue sequence regions, which regions are designated the catalytic region, the membrane binding region and the linker region. The catalytic region contains the active site of the HMG-CoA reductase enzyme and comprises about forty percent of the COOH-terminal portion of intact HMG-CoA reductase enzyme. The membrane binding region contains hydrophobic amino acid residues and comprises about fifty percent of the $NH_2$-terminal portion of intact HMG-CoA reductase enzyme. The linker region connects the catalytic and membrane binding regions, and constitutes the remaining about ten percent of the intact enzyme.

As discussed in greater detail below, only the catalytic region of HMG-CoA reductase is needed herein. Thus, a structural gene that encodes a polypeptide corresponding to that catalytic region is the minimal gene required for transforming plants. However, larger enzymes and their structural genes are preferred. Thus, the present invention contemplates use of both intact and truncated structural genes that encode a polypeptide having HMG-CoA reductase activity.

A structural gene encoding a polypeptide having HMG-CoA reductase activity can be obtained or constructed from a variety of sources and by a variety of methodologies. See, e.g., Carlson, M. and Botstein, D., *Cell*, 28:145 (1982); Rine, J., et al., *Proc. Nat. Acad. Sci. U.S.A.*, 80:6750 (1983). Exemplary of such structural genes are the mammalian and yeast genes encoding HMG-CoA reductase.

The mammalian genome contains a single gene encoding HMG-CoA reductase. The nucleotide base sequence of the hamster and human gene for HMG-CoA reductase have been described. A composite nucleotide sequence of cDNA corresponding to the mRNA (SEQ. ID No. 1), as well as the derived amino acid residue sequence (SEQ. ID No. 2), for hamster HMG-CoA reductase is provided in FIG. 2, reprinted from Chin, D. J. et al., *Nature*, 308:613 (1984). The composite nucleotide sequence of FIG. 2 (SEQ. ID No. 1), comprising about 4606 base pairs, includes the nucleotide sequence encoding the intact hamster HMG-CoA reductase enzyme.

Intact hamster HMG-CoA reductase comprises about 887 amino acid residues (SEQ. ID No. 2). A structural gene encoding an intact hamster HMG-CoA reductase enzyme of 887 amino acid residues comprises base pairs from about nucleotide position 1 to about nucleotide position 2661 of FIG. 2 (SEQ. ID No. 1).

A preferred structural gene is one that encodes a polypeptide corresponding to only the catalytic region of the enzyme. Two catalytically active segments of hamster HMG-CoA reductase have been defined. Liscum, L. et al., *N Biol. Chem.*, 260(1):522 (1985). One catalytic region has an apparent molecular weight of 62 kDa and comprises amino acid residues from about position 373 to about position 887. A second catalytic region has an apparent molecular weight of 53 kDa segment and comprises amino acid residues from about position 460 to about position 887. The 63 kDa catalytically active segment is encoded by base pairs from about nucleotide position 1119 to about nucleotide position 2661 of FIG. 2 (SEQ. ID No. 1). The 53 kDa catalytically active segment is encoded by base pairs from about nucleotide position 1380 to about nucleotide position 2661 of FIG. 2 (SEQ. ID No. 1).

In a preferred embodiment, the utilized structural gene encodes the catalytic region and at least a portion of the linker region of HMG-CoA reductase. The linker region of hamster HMG-CoA reductase comprises amino acid residues from about position 340 to about position 373 or from about position 340 to about position 460, depending upon how the catalytic region is defined. These linker regions are encoded by base pairs from about nucleotide position 1020 to about nucleotide position 1119 or from about position 1020 to about position 1380 respectively of FIG. 2 (SEQ. ID No. 1). The structural gene encoding region is operatively linked to the structural gene encoding the catalytic region.

In one particularly preferred embodiment, a structural gene encoding a catalytically active, truncated HMG-CoA reductase enzyme can optionally contain base pairs encoding a small portion of the membrane region of the enzyme. A truncated hamster HMG-CoA reductase gene, designated HMGR-Δ227, comprising nucleotides 1–27 and 1024–2661 from FIG. 2 (SEQ. ID No. 1), which encodes amino acid residues 1–9 (from the membrane binding region) and 342–887 has been used to transform cells lacking HMG-CoA reductase. The schematic structure of the transforming plasmid (pRED-227Δ) containing the truncated gene is reprinted in FIG. 4. A structural gene encoding a polypeptide comprising a catalytically active, truncated or intact HMG-CoA reductase enzyme from other organisms such as yeast can also be used in accordance with the present invention.

Yeast cells contain two genes encoding HMG-CoA reductase. The two yeast genes, designated HMG1 and HMG2, encode two distinct forms of HMG-CoA reductase, designated HMG-CoA reductase 1 and HMG-CoA reductase 2. The nucleotide base sequences of HMG1 (SEQ. ID No. 3) and HMG2 (SEQ. ID No. 5) as well as the amino acid residue sequences of HMG-CoA reductase 1 (SEQ. ID No. 4) and HMG-CoA reductase 2 (SEQ. ID No. 6) are presented in FIG. 3, reprinted from Basson, M. E. et al., *Mol. Cell Biol.*, 8(9):3797 (1988).

The entire HMG1 gene comprises about 3240 base pairs (SEQ. ID No. 3). Intact HMG-CoA reductase 1 comprises an amino acid sequence of about 1054 amino acid residues (SEQ. ID No. 4). Thus, the minimal portion of the HMG1 gene that encodes an intact enzyme comprises base pairs from about nucleotide position 1 to about position 3162 of FIG. 3 (SEQ. ID No. 3).

The entire HMG2 gene comprises about 3228 base pairs (SEQ. ID No. 5). Intact HMG-CoA reductase 2 comprises about 1045 amino acid residues (SEQ. ID No. 6). Thus, the minimal portion of HMG2 gene that encodes intact HMG-CoA reductase 2 comprises base pairs from about nucleotide position 1 to about position 3135 of FIG. 3 (SEQ. ID No. 5).

By analogy to the truncated hamster structural gene, structural genes encoding polypeptides comprising catalytically active, truncated HMG-CoA reductase enzymes from yeast can also be used in accordance with the present invention.

The catalytic region of HMG-CoA reductase 1 comprises amino acid residues from about residue 618 to about residue 1054: i.e., the COOH-terminus. A structural gene that encodes the catalytic region comprises base pairs from about nucleotide position 1854 to about position 3162 of FIG. 3.

The linker region of HMG-CoA reductase 1 comprises an amino acid sequence from about residue 525 to about residue 617. A structural gene that encodes the linker region comprises nucleotides from about position 1575 to about position 1854 of FIG. 3. A structural gene encoding a polypeptide comprising the catalytic region and at least a portion of the linker region of yeast HMG-CoA reductase 1 preferably comprises the structural gene encoding the linker region of the enzyme operatively linked to the structural gene encoding the catalytic region of the enzyme.

Also by analogy to the truncated hamster gene, a truncated HMG1 gene can optionally contain nucleotide base pair sequences encoding a small portion of the membrane binding region of the enzyme. Such a structural gene preferably comprises base pairs from about nucleotide position 1 to about position 26 and from about position 1575 to about position 3162 of FIG. 3.

A construct similar to those above from an analogous portion of yeast HMG-CoA reductase 2 can also be utilized.

It will be apparent to those of skill in the art that the nucleic acid sequences set forth herein, either explicitly, as in the case of the sequences set forth above, or implicitly with respect to nucleic acid sequences generally known and not presented herein, can be modified due to the built-in redundancy of the genetic code and non-critical areas of the polypeptide that are subject to modification and alteration. In this regard, the present invention contemplates allelic variants of structural genes encoding a polypeptide having HMG-CoA reductase activity.

The previously described DNA segments are noted as having a minimal length, as well as total overall lengths. That minimal length defines the length of a DNA segment having a sequence that encodes a particular polypeptide having HMG-CoA reductase activity. As is well known in the art, so long as the required DNA sequence is present, (including start and stop signals), additional base pairs can be present at either end of the segment and that segment can still be utilized to express the protein. This, of course, presumes the absence in the segment of an operatively linked DNA sequence that represses expression, expresses a further product that consumes the enzyme desired to be expressed, expresses a product other than the desired enzyme or otherwise interferes with the structural gene of the DNA segment.

Thus, so long as the DNA segment is free of such interfering DNA sequences, a DNA segment of the invention can be up to 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known.

B. Recombinant DNA Molecules

A recombinant DNA molecule of the present invention can be produced by operatively linking a vector to a useful DNA segment to form a plasmid such as those discussed and deposited herein. A particularly preferred recombinant DNA molecule is discussed in detail in Example 1, hereafter. A vector capable of directing the expression of a polypeptide having HMG-CoA reductase activity is referred to herein as an "expression vector".

Such expression vectors contain expression control elements including the promoter. The polypeptide coding genes are operatively linked to the expression vector to allow the promoter sequence to direct RNA polymerase binding and expression of the desired polypeptide coding gene. Useful in expressing the polypeptide coding gene are promoters that are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chau et al., *Science*, 244:174-181 (1989). The promoter preferably comprises a promoter sequence whose function in regulating expression of the structural gene is substantially unaffected by the amount of sterol in the cell. As used herein, the term "substantially unaffected" means that the promoter is not responsive to direct feedback control by the sterols accumulated in transformed cells.

A promoter is also selected for its ability to direct the transformed plant cell's transcriptional activity to the structural gene encoding a polypeptide having HMG-CoA reductase activity. Structural genes can be driven by a variety of promoters in plant tissues. Promoters can be near-constitutive, such as the CaMV 35S promoter, or tissue specific or developmentally specific promoters affecting dicots or monocots. Exemplary promoters are corn sucrose synthestase 1 (Yang, N. S., et al. *Proc. Natl. Acad. Sci. U.S.A.*, 87:4144-48 (1990)), corn alcohol dehydrogenase 1 (Vogel, J. M., et al., *J. Cell Biochem.*, (supplement 13D, 312)(1989)), corn zein 19KD gene (storage protein) (Boston, R. S., et al., *Plant Physiol.*, 83:742-46), corn light harvesting complex (Simpson, J., *Science*, 233:34 (1986), corn heat shock protein (O'Dell, J. T., et al., *Nature*, 313:810-12 (1985), pea small subunit RuBP Carboxylase (Poulsen, C., et al., *Mol. Gen. Genet.*, 205:193-200 (1986); Cushmore, A. R., et al., *Gen. Eng. of Plants*, Plenum Press, New York, 29-38 (1983), Ti plasmid mannopine synthase (Langridge, W. H. R., et al., *Proc. Natl. Acad. Sci. U.S.A.*, 86:3219-3223 (1989), Ti plasmid nopaline synthase (Langridge, W. H. R., et al., *Proc. Natl. Acad. Sci. U.S.A.*, 86:3219-3223 (1989), petunia chalcone isomerase (Van Tunen, A. J., et al., *EMBO J.*, 7:1257 (1988), bean glycine rich protein 1 (Keller, B., et al., *EMBO J.*, 8:1309-14 (1989), CaMV 35s transcript (O'Dell, J. T., et al., *Nature*, 313:810-12 (1985) and Potato patatin (Wenzler, H. C., et al., *Plant Mol. Biol.*, 12:41-50 (1989). Preferred promoters are the cauliflower mosaic virus (CaMV) 35S promoter and the S-E9 small subunit RuBP carboxylase promoter.

The choice of which expression vector and ultimately to which promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding gene included in the DNA segment to which it is operatively linked.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253-277 (1987). However, several other expression vector systems are known to function in plants including pCaMVCN transfer control vector described by Fromm et al., *Proc. Natl. Acad. Sci. USA*, 82:5824 (1985). Plasmid pCaMVCN (available from Pharmacia, Piscataway, N.J.) includes the cauliflower mosaic virus CaMV 35 S promoter.

The use of retroviral expression vectors to form the recombinant DNAs of the present invention is also contemplated. As used herein, the term "retroviral expression vector" refers to a DNA molecule that includes a promoter sequence derived from the long terminal repeat (LTR) region of a retrovirus genome.

In preferred embodiments, the vector used to express the polypeptide coding gene includes a selection marker that is effective in a plant cell, preferably a drug resistance selection marker. One preferred drug resistance marker is the gene whose expression results in kanamycin resistance, i.e., the chimeric gene containing the nopaline synthase promoter, Tn5 neomycin phosphotransferase II and nopaline synthase 3' nontranslated region described by Rogers et al., in *Methods For Plant Molecular Biology*, A. Weissbach and H. Weissbach, eds., Academic Press Inc., San Diego, Calif. (1988). Another preferred marker is the assayble chloramphenicol acetyltransferase (cat) gene from the transposon Tn9.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

A preferred recombinant DNA molecule utilized in accordance with the present invention is plasmid HMGRΔ227-pKYLX71.

C. Transformed Plants and Methods of Transformation

The copy number of a gene coding for a polypeptide having HMG-CoA reductase activity is increased by transforming a desired plant with a suitable vector that contains that structural gene. Expression of that gene in the transformed plant enhances the activity of HMG-CoA reductase.

Methods for transforming polypeptide coding genes into plants include Agrobacterium-mediated plant transformation, protoplast transformation, gene transfer into pollen, injection into reproductive organs and injection into immature embryos. Each of these methods has distinct advantages and disadvantages. Thus, one particular method of introducing genes into a particular plant species may not necessarily be the most effective for another plant species, but it is well known which methods are useful for a particular plant species.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated expression vectors to introduce DNA into plant cells is well known in the art. See, for example, the methods described by Fraley et al., *Biotechnology*, 3:629 (1985) and Rogers et al., *Methods in Enzymology*, 153:253-277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179-203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

In those plant species where Agrobacterium-mediated transformation is efficient, it is the method of choice because of the facile and defined nature of the gene transfer.

Agrobacterium-mediated transformation of leaf disks and other tissues appears to be limited to plant species that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described by Bytebier et al., *Proc. Natl. Acad. Sci. U.S.A.*, 84:5345 (1987). Therefore, commercially important cereal grains such as rice, corn, and wheat must be transformed using alternative methods. However, as mentioned above, the transformation of asparagus using Agrobacterium can also be achieved. See, for example, Bytebier, et al., *Proc. Natl. Acad. Sci.*, 84:5345 (1987).

A plant transformed using Agrobacterium typically contains a single gene on one chromosome. Such plants are heterozygous for the added gene. A heterozygous transformant containing a single structural gene that encodes a polypeptide having HMG-CoA reductase activity is a preferred transformed plant.

More preferred is a plant that is homozygous for the added structural gene; i.e., a plant that contains two added genes, one gene on each chromosome of a chromosome pair. A homozygous transformed plant can be obtained by sexually mating (selfing) a heterozygous plant, germinating some of the seed produced and analyzing the resulting plants produced for enhanced HMG-CoA reductase activity or sterol accumulation, or both, relative to a control or a heterozygous plant. A homozygous plant exhibits enhanced HMG-CoA reductase activity and sterol accumulation.

Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985): Fromm et al., *Nature*, 319:791 (1986): Uchimiya et al., *Mol. Gen. Genet.*, 204:204 (1986): Callis et al., *Genes and Development*, 1:1183 (1987): and Marcotte et al., *Nature*, 335:454 (1988).

Application of these systems to different plant species depends upon the ability to regenerate that particular plant species from protoplasts. Illustrative methods for the regeneration of cereals from protoplasts are described in Fujimura et al., *Plant Tissue Culture Letters*, 2:74 (1985); Toriyama et al., *Theor Appl. Genet.*, 73:16 (1986); Yamada et al., *Plant Cell Rep.*, 4:85 (1986); Abdullah et al., *Biotechnology*, 4:1087 (1986).

To transform plant species that cannot be successfully regenerated from protoplasts, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized.

Using that latter technology, DNA is carried through the cell wall and into the cytoplasm on the surface of small metal particles as described in Klein et al., *Nature*, 327:70 (1987); Klein et al., *Proc. Natl. Acad. Sci. U.S.A.*, 85:8502 (1988); and McCabe et al., *Biotechnology*, 6:923 (1988). The metal particles penetrate through several layers of cells and thus allow the transformation of cells within tissue explants.

Metal particles have been used to successfully transform corn cells and to produce fertile, stably transformed tobacco plants as described by Gordon-Kamm, W. J. et al., *The Plant Cell*, 2:603-618 (1990); Klein, T. M. et al., *Plant Physiol.* 91:440-444 (1989); Klein, T. M. et al., *Proc. Natl. Acad. Sci. USA*, 85:8502-8505 (1988); and Tomes, D. T. et al., *Plant Mol. Biol.* 14:261-268 (1990). Transformation of tissue explants eliminates the need for passage through a protoplast stage and thus speeds the production of transgenic plants.

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo* 1986, Butterworth, Stoneham, Mass., pp. 27-54 (1986).

The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the foreign gene introduced by Agrobacterium from leaf explants can be achieved as described by Horsch et al., *Science*, 227:1229-1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983).

This procedure typically produces shoots within two to four months and these transformant shoots are then transferred to an appropriate root-inducing medium containing the selective agent and an antibiotic to prevent bacterial growth. Transformant shoots that rooted in the presence of the selective agent to form plantlets are then transplanted to soil or other media to allow the production of roots. These procedures vary depending upon the particular plant species employed, such variations being well known in the art.

Mature regenerated plants are obtained that exhibit increased sterol accumulation due to expression of the HMG-CoA reductase polypeptide gene. Preferably, the regenerated plants are self pollinated. Otherwise, pollen obtained from the regenerated plants is crossed to seed-grown plants of agronomically important, preferably inbred lines. Conversely, pollen from plants of those important lines is used to pollinate regenerated plants. The presence of the added gene in the progeny is assessed as discussed hereinafter.

A plant of the present invention containing a desired HMG-CoA reductase polypeptide is cultivated using methods well known to one skilled in the art. Any of the transgenic plants of the present invention can be cultivated to isolate the desired sterol products they contain.

A transformed plant of this invention thus has an increased copy number of a structural gene that encodes a polypeptide having HMG-CoA reductase activity. A preferred transformed plant is heterozygous for the added HMG-CoA reductase structural gene, whereas a more preferred transformed plant is homozygous for that gene, and transmits that gene to all of its offspring on sexual mating.

A transformed plant of the invention accumulates sterols relative to a native plant, as is discussed immediately below. A transformed plant also exhibits resistance to pests such as the hornworms as is discussed hereinafter.

D. Development of Commercial Hybrid Seed

Seed from a transformed plant is grown in the field or greenhouse and self-pollinated to generate true breeding plants. The progeny from these plants become true breeding lines that are evaluated for sterol accumulation, preferably in the field, under a range of environmental conditions.

The commercial value of a plant with increased sterol accumulation is enhanced if many different hybrid combinations are available for sale. The user typically grows more than one kind of hybrid based on such differences as maturity, standability or other agronomic traits. Additionally, hybrids adapted to one part of a country are not necessarily adapted to another part because of differences in such traits as maturity, disease and herbicide resistance. Because of this, sterol accumulation is preferably bread into a large number of parental lines so that many hybrid combinations can be produced.

Adding an enhanced sterol accumulation trait to an agronomically elite line is accomplished by a variety of techniques well known to those of skill in the art. For example, parent plants that are either homozygous or heterozygous for enhanced sterol accumulation are crossed with lines having other desireable traits, such as herbicide resistance (U.S. Pat. No. 4,761,373) produce hybrids. Preferably, plants homozygous for enhanced sterol accumulation are used to generate hybrids.

For example, a plant homozygous for enhanced sterol accumulation is crossed with a parent plant having other desired traits. The progeny, which are heterozygous for enhanced sterol accumulation, are backcrossed with the parent to obtain plants having enhanced sterol accumulation and the other desired traits. The backcrossing of progeny with the parent may have to be repeated more than once to obtain a plant that possesses all desireable traits.

Alternatively, plants with the enhanced sterol accumulation trait are transformed by introducing into such plants other genes that encode and express other desireable traits or mutated as with radiation, e.g. X-rays or gamma rays, as in U.S. Pat. No. 4,616,099, whose disclosures are incorporates by reference. Thus, the present invention also contemplates mutants and genetically engineered derivatives of plants having enhanced sterol accumulation.

E. Accumulation of Sterols in Transformed Plants

The present invention provides methods for increasing the accumulation of sterols, particularly cycloartenol, in plants. This is accomplished by increasing the copy number of a gene encoding for a polypeptide having HMG-CoA reductase activity and subsequent expression of that encoded polypeptide.

In normal, non-transformed plants sterol accumulation is equal to about 0.3 weight percent of the dry weight on the plant. The predominant sterols accumulated by such normal plants are campesterol, sitosterol, stigmasterol and derivatives of cholesterol. These sterols, $\Delta 5$-derivatives of cycloartenol that have undergone desaturation of the 5(6) carbon-carbon bond of cycloartenol, comprise over 80 weight percent of total sterols in normal plants. Cycloartenol normally comprises from about 3 to about 30 percent of the total sterols present in a plant.

Plants having an increased copy number of a gene encoding a polypeptide having HMG-CoA reductase activity demonstrate a marked increase in total sterol accumulation. Further, the predominant sterol found in such plants is cycloartenol, which represents from about 60 to about 70 weight percent of total sterols of a transformed plant.

Thus, the present invention provides plants that over accumulate sterols relative to a native plant. Transformed heterozygous plants accumulate total sterol to a level about twice that found in native untransformed plants. In particular, transformed heterozygous plants accumulate cycloartenol to a level from about ten to about one hundred times greater than found in native plants.

These results are surprising and unexpected in light of studies relating HMG-CoA reductase activity and sterol accumulation in other organisms.

In yeast, increases in HMG-CoA reductase activity are associated with increases in squalene (a sterol precursor), 4,14-dimethylzymosterol and 14-methylfecosterol (analogous to the $\Delta 5$-sterols of plants). Downing, J. F. et al., *Biochemical and Biophysical Research Communications*, 94(3): 974–979(1980). Increases in HMG-CoA reductase activity of yeast were not associated with increases in lanosterol, (a sterol of yeast analogous to cycloartenol). Benveniste, P., *Ann. Rev. Plant Physiol.*, 37: 275–308 (1986).

In non-photosynthetic microorganisms, increases in HMG-CoA reductase activity were not associated with increases in sterol accumulation. Tada, M. and Shiroishi, M. *Plant and Cell Physiology*, 23(4): 615–621(1982).

F. Harvesting of Sterols

If desired, after cultivation, the transgenic plant is harvested to recover the sterol product. This harvesting step can consist of harvesting the entire plant, or only the leaves, or roots of the plant. This step can either kill the plant or, if only a non-essential portion of the transgenic plant is harvested, can permit the remainder of the plant to continue to grow.

In preferred embodiments this harvesting step further comprises the steps of:

(i) homogenizing at least a sterol-containing portion of the transgenic plant to produce a plant pulp and using the sterol-containing pulp directly, as in dried pellets or tablets as where an animal food is contemplated; or (ii) extracting the sterol(s) from the plant pulp with an appropriate solvent such as an organic solvent or by supercritical extraction [Favati et al., *J. Food Sci.*, 53:1532 (1988) and the citations therein] to produce a sterol-containing liquid solution or suspension; and (iii) isolating the sterol(s) from the solution or suspension.

At least a portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of the sterol of interest, residual amounts of precursors, cellular particles and cytosol contents. This pulp can be dried and compressed into pellets or tablets and eaten or otherwise used to derive the benefits, or the pulp can be subjected to extraction procedures.

The sterol can be extracted from the plant pulp produced above to form a sterol-containing solution or suspension. Such extraction processes are common and well known to one skilled in this art. For example, the extracting step can consist of soaking or immersing the plant pulp in a suitable solvent. This suitable solvent is capable of dissolving or suspending the sterol present in the plant pulp to produce a sterol-containing solution or suspension. Solvents useful for such an extraction process are well known to those skilled in the art and include several organic solvents and combinations thereof such as methanol, ethanol, isopropanol, acetone, acetonitrile, tetrahydrofuran (THF), hexane, and chloroform as well as water-organic solvent mixtures. A vegetable oil such as peanut, corn, soybean and similar oils can also be used for this extraction.

A plant transfected with a structural gene for a polypeptide having HMG-CoA reductase activity is grown under suitable conditions for a period of time sufficient for sterols to be synthesized. The sterol-containing plant cells, preferably in dried form, are then lysed chemically or mechanically, and the sterol is extracted from the lysed cells using a liquid organic solvent, as described before, to form a sterol-containing liquid solution or suspension. The sterol is thereafter isolated from the liquid solution or suspension by usual means such as chromatography.

The sterol is isolated from the solution or suspension produced above using methods that are well known to those skilled in the art of sterol isolation. These methods include, but are not limited to, purification procedures based on solubility in various liquid media, chromatographic techniques such as column chromatography and the like.

G. Pest Resistance of Transformed Plants

Certain sterols accumulated by the transformed plants of the present invention have use as systemic pesticidal agents. This embodiment of the present invention relates to a method of increasing pest resistance of a plant comprising transforming a native plant with a recombinant DNA molecule comprising a vector operatively linked to an exogenous DNA segment that encodes the catalytic region of HMG-CoA reductase, and a promoter suitable for driving the expression said reductase in said plant. In preferred practice, the exogenous DNA segment also encodes at least a portion of the linker region but not the membrane binding region of HMG-CoA reductase. Use of the hamster gene is particularly preferred.

Tobacco hornworm larvae grown on the leaves of plants transformed with a truncated hamster HMG-CoA reductase gene, which plants have increased levels of cyclartenol, demonstrated retarded development. Preliminary studies also indicate that boll worms fed on leaves of a similarly transformed plant had retarded development under similar condition.

The following examples illustrate the best mode of carrying out the invention and are not to be construed as limiting of the specification and claims in any way.

BEST MODE FOR CARRYING OUT THE INVENTION

Example 1

Transformation of Plant Cells

Plant cells were transformed in accordance with standard methods for expressing foreign genes in plants. Schardl, C. L., et al. *Gene* 61:1-11 (1987). A pKYLX series of vectors was used as the expression system. Preferred vectors are plasmids pKYLX6 and pKYLX7. Berger, P. J., et al., *Proc. Natl. Acad. Sci. USA*, 86: 8402-8406 (1989).

Transformations were performed with a truncated Hamster HMG-CoA reductase gene (HMGR-Δ227) obtained from the laboratories of Dr. J. L. Goldstein, See, e.g., Gil, G. et al., *Cell*, 41: 249-258(1985); Bard, M. and Downing, J. F. *Journal of General Microbiology*, 125:415-420(1981).

The HMGR-Δ227 gene was incorporated into modified vectors pKYLX6 (an *E. coli* vector designed for intermediate constructs) and pKYLX7 (an *A. tumefaciens* vector designed for integration of cloned genes). Berger, P. J., et al., *Proc. Natl. Acad. Sci. USA*, 86: 8402-8406 (1989). The modified vectors pKYLX61 and pKYLX71 contained Hind III, Xho I, Bam HI, Pst I, and Sst I sites in place of the original Hind III Sst I fragment multiple cloning site region.

The HMGR-Δ227 gene was digested with Bam HI and Sst I, and the approximately, 2500 bp HMGR-Δ227-Bam HI-Sst I fragment was inserted into plasmid pKYLX61. The resulting HMGRΔ227-pKYLX61 construct was cleaved with Eco RI and Cla I, and an approximately 4000 bp fragment containing the promoter-gene-terminator was inserted into corresponding sites of pKYLX71 to generate plasmid HMGRΔ227-pKYLX71 (see FIG. 5). In plasmid HMGRΔ227-KYLX71, the truncated HMGR-Δ227 gene is under control of the strong, constitutive CaMV35S promoter.

The HMGRΔ227-pKYLX71 plasmid was mobilized into *Agrobacterium tumefaciens* by a standard triparental mating between *E. coli*, harboring the HMGRΔ227-pKYLX71 construct, *Argrobacterium tumefaciens*, harboring disarmed Ti-plasmid, GV3850, and *E. coli* harboring the conjugation helper plasmid pRK2013. See. e.g., Schardl, et al., Supra; Ditta, G. et al., *Proc. Natl. Acad. Sci. USA* 77:7347-7351 (1980). As a result of the cross, Agrobacterium harboring the HMGRΔ227-pKYLX71 construct, was selected for by resistance to rifampicin (encoded on the chromosome of Agrobacterium), and to tetracycline and kanamycin (encoded on the pKYLX71 vector).

*Nicotiana tabacum* L. cv. xanthii (*N. tabacum*) was transformed by the well known "leaf disk method". Horsch, R. B., et al., *Science* 27:1229-1231 (1985). Leaf disks were incubated with Agrobacteria containing Δ227-pKYLX71 for about 3 days. Transformed tissue was selected for by resistance to kanamycin (encoded by the pKYLX71 vector), cured of Agrobacteria using the antibiotic mefoxin, and regenerated into whole plants. Horsch, R. B., et al., *Science* 27:1229-1231 (1985).

Plant tissue was checked for the presence of integrated copies of the HMGR Δ227 gene sequences by the method of Mettler, *Plant Mol. Biol. Reporter* 5:346-349 (1987). RNA transcription levels were determined by northern blotting or S-1 protection assays. Maniatis, T., et al., *Molecular Cloning: A Laboratory Manual*, Cold Spring Harbour Lab., Cold Spring Harbour, N.Y. (1982).

Plants exhibiting HMG-CoA reductase activity greater than control plants [untransformed (native) or transformed without the HMGR-Δ227-construct] were sexually crossed with themselves, to generate progeny.

Example 2

HMG-CoA Reductase Enzyme Activity in Transgenic Plants

Transgenic plants were screened for expression of the truncated HMGR gene by examining HMG-CoA reductase activity in the 100,000 xG supernatant of lysed cells using a standard assay, Chappell, J., and Nable, R., *Plant Physiol.* 85:469-473 (1987).

Soluble HMG-CoA reductase enzyme activity was measured in callus cultures grown on selection (kanamycin) medium, seedlings germinated in the presence of kanamycin or on moistened filter paper, and leaves of various sizes from plants grown in the greenhouse. Results of studies of HMG-CoA reductase activity in leaves from greenhouse-grown plants are also summarized in Table 1 below:

TABLE 1

| Plant Sample No. | Total HMG-CoA Reductase Activity (pmol/hr./leaf) | % of Control |
|---|---|---|
| Control |  |  |
| 30 | 258 | 100 |
| Transformed |  |  |
| 5 | 860 | 300 |

TABLE 1-continued

| Plant Sample No. | Total HMG-CoA Reductase Activity (pmol/hr./leaf) | % of Control |
|---|---|---|
| 14 | 1,100 | 390 |
| 15 | 633 | 220 |
| 18 | 456 | 160 |
| 23 | 713 | 250 |

The control plant, 30, was transformed with a selection marker but not with the Δ227 gene. Plants 5, 14, 15, 18 and 23 (independently transformed) were transformed with the HMGR-Δ227 gene.

Total HMG-CoA reductase activity was 1.6 to 3.9 times greater in plants harboring the Δ227 gene as compared to the control plant.

Example 3

Sterol Accumulation in Transformed Plants

*N. tabacum*, transformed with the HMGR-Δ227 gene according to the method of Example 1 were analyzed for total sterol content. Sterols were measured by analytical gas chromatography using an internal standard. The results are presented in Table 2.

TABLE 2

| Plant Sample | HMG-CoA Reductase (pmol/mg dry wt.) | Total Sterols (% of dry wt) |
|---|---|---|
| Control Plants (n = 6) | 2.00 ± 0.19 | 0.27 ± 0.02 |
| Transformed Plants (n = 12) | 5.75 ± 1.55 | 0.89 ± 0.17 |

Transformed plants had elevated HMG-CoA reductase activity and increased sterol content.

In addition to determining total sterol content, transformed *N. tabacum* were examined for the accumulation of specific sterols. The results of such an analysis in a control (Cntrl) and HMGR-Δ227 transformed (Trf) plant are presented in Table 3.

TABLE 3

| | Percent Dry weight of Sterols | | | | | |
|---|---|---|---|---|---|---|
| | Callus | | Leaf | | Root | |
| Sterols | Cntrl | Trf | Cntrl | Trf | Cntrl | Trf |
| Campesterol | 0.009 | 0.021 | 0.057 | 0.056 | 0.058 | 0.022 |
| Cholesterol | 0.004 | tr | tr | tr | tr | tr |
| Cycloartenol | 0.003 | 0.258 | 0.011 | 0.678 | 0.039 | 0.642 |
| Sitosterol | 0.027 | 0.077 | 0.083 | 0.187 | 0.029 | 0.194 |
| Stigmasterol | 0.003 | 0.012 | 0.132 | 0.078 | tr | 0.238 | tr = trace (<0.001 % dry wt.)

In the control plant, cycloartenol represented from about 3(0.011/0.283 percent dry weight) (leaf) to about 30(0.039/0.126 percent dry weight) (root) percent of total sterol accumulation. The predominant sterols accumulated by control plants (i.e. sitosterol, Campersterol) are Δ5-sterol derivatives of cycloartenol that have undergone additional metabolic transformation.

As a result of transformation with the HMGR-Δ227 gene, the ratio of cycloartenol to its derivatives is reversed. In transformed plants, cycloartenol accumulation represents from about 60 (root) to about 70 (leaf) percent by weight of total sterol accumulation.

These data show that transformed plants of the present invention over accumulate sterols relative to a native, untransformed plant. Transformed, heterozygous plants over accumulate total sterols to a level about twice that found in a native plant. The data further show that transformed heterozygous plants over accumulate cycloartenol to a level about ten to about one hundred times greater than found in a native plant.

Example 4

Insecticidal Effects of Transformed Plants

First instar larvae of the tobacco pests Tobacco Hornworm or Manduca Sexta, were placed onto leaves of control or HMGR-Δ227 transformed *N. tabacum* on a moistened filtered paper in a petri dish. Additional leaf material, from control or transformed plants, was added to each dish, and the larvae were grown for an additional 7 days. Larvae were then examined to determine growth and development. The results are presented in Table 4.

TABLE 4

| | Control | Transformed |
|---|---|---|
| Development | | |
| % of larvae in second instar | 28.6 | 100 |
| % of larvae in premolt or third instar | 71.4 | 0 |
| Growth | | |
| Fresh Wet Weight (mg) | 42.8 | 24.4 |

Tobacco Hornworm or Manduca Sexta larvae grown on leaves from HMGR-Δ227-transformed plants demonstrated retarded development (no progression beyond the second instar stage) and inhibited growth (wet weight) as compared to controls. The cycloartenol levels of the control and transformed plants used in this study were 0.017 and 1.02 percent of dry leaf weight, respectively. This study thus illustrates both the method of increasing the accumulation of cycloartenol in a plant and of enhancing pest resistance in a plant.

Preliminary studies with a member of the helio- thus group of insect pests, the boll worm, indicate a slower growth rate for insects fed on leaves of transformed plant 14 (Example 2) than on leaves of the native, control plant 30 (Example 2). An effect on the fecundity of the insects fed on either type of leaf was also noted.

Example 5

Homozygous Transformed Plants

The previously described transformed plants were heterozygous for the introduced HMG-CoA reductase gene. One of those plants, plant 14 of Example 2, was selfed; i.e., sexually mated with itself.

Twelve seed from that cross were germinated and raised into plants. The tissues of those siblings were then analyzed for HMG-CoA reductase activity, total protein and total sterol content. The specific activity of HMG-CoA reductase was also calculated. The results of that assay compared to similar data from siblings from a selfing of plant 30 (Example 2) are presented in Table 5, below.

TABLE 5

| Plant | HMGR Activity[1] | Protein[2] | Specific Activity[3] | Sterols[4] |
|---|---|---|---|---|
| 30-1 | 3.78 | 30.22 | 184 | 0.20 |
| 30-2 | 2.20 | 30.00 | 146 | 0.25 |
| 30-3 | 1.44 | 18.70 | 154 | 0.29 |
| 30-4 | 2.13 | 23.67 | 180 | 0.31 |
| 30-5 | 1.70 | 19.27 | 176 | 0.36 |
| 30-6 | 1.77 | 19.32 | 183 | 0.22 |
| 14-1 | 1.36 | 23.60 | 115 | 0.21 |

TABLE 5-continued

| Plant | HMGR Activity[1] | Protein[2] | Specific Activity[3] | Sterols[4] |
|---|---|---|---|---|
| 14-2 | 2.07 | 26.55 | 156 | 0.17 |
| 14-3 | 10.28 | 17.60 | 1168 | 1.10 |
| 14-4 | 7.08 | 27.25 | 520 | 0.74 |
| 14-5 | 4.13 | 20.92 | 394 | 1.59 |
| 14-6 | 1.58 | 11.00 | 143 | 0.25 |
| 14-7 | 20.35 | 16.77 | 2,426 | 2.05* |
| 14-8 | 4.87 | 24.20 | 402 | 0.97 |
| 14-9 | 2.37 | 12.95 | 366 | 0.19 |
| 14-10 | 7.94 | 11.00 | 1,444 | 1.02 |
| 14-11 | 2.56 | 15.25 | 334 | 1.10 |
| 14-12 | 4.39 | 21.10 | 416 | 1.29 |

[1] pmoles/0.5 hours.
[2] micrograms (mg).
[3] pmoles of enzyme/hour/mg of total protein.
[4] percentage of dry weight.
*this plant died.

On the basis of the above data, the plants were classified as to (a) having no added HMG-CoA reductase gene, (b) being heterozygous for the added gene, as was plant 14, or (c) homozygous for the added gene. Illustratively, plant 14-2 was thus determined to be heterozygous for the added gene, plant 14-6 was determined to be heterozygous for the added gene and plant 14-8 was determined to be homozygous for the added gene; i.e., it contained an added gene on each of two chromosomes.

These data show that seeds from a transformed plant are capable of germinating into a plant capable of expressing enhanced sterol accumulation due to an increased copy number of gene encoding a polypeptide having HMG-CoA reductase activity.

Taken together with the data of Example 3, these data show that the transformed plants of the present invention over accumulate sterols relative to a native plant and that such plants are capable of producing seeds, which germinate into plants that over accumulate sterols.

Seeds from a selfing of plant 14-8 were deposited pursuant to the Budapest Treaty requirements with the American Type Culture Collection (ATCC) at 12301 Parklawn Drive, Rockville, Md. 20852 U.S.A. on Sep. 28, 1990, and were assigned accession number ATCC 40904.

The present invention has been described with respect to preferred embodiments. It will be clear to those skilled in the art that modifications and/or variations of the disclosed subject matter can be made without departing from the scope of the invention set forth herein.

---

We claim:

1. A method of increasing sterol accumulation in a plant, said method comprising: transforming plant material with a DNA construct comprising a structural gene, said structural gene consisting essentially of necleotides encoding an HMG-CoA reductase enzyme catalytic region and at least a portion of the HMG-CoA reductase linker region; and regenerating the transformed plant, wherein said transformed plant has a total sterol level of about twice that found in a native, untransformed plant and said transformed plant has a cycloartenol level greater than that found in a native, untransformed plant.

2. A method according to claim 1 wherein the transformed plant has a cycloartenol level of at least about ten times greater than that found in a native, untransformed plant.

3. A method according to claim 1 wherein the DNA construct further comprises a promoter operatively linked to said structural gene.

4. A method according to claim 3 wherein said promoter is a promoter whose regulatory function is substantially unaffected by the level of sterol in said plant.

5. A method according to claim 4 wherein the promoter is the CaMV promoter.

6. A method according to claim 1 wherein the plant to be transformed is selected from the group consisting of: tobacco, tomato, corn, carrot, soybean, cotton, barley, arabidopsis, guayule, and petunia.

7. A method according to claim 3 wherein the DNA construct is plasmid HMGRΔ227-pKYLX71.

8. A method of increasing cycloartenol accumulation in a plant, said method comprising: transforming plant material with a DNA construct comprising a structural gene, said structural gene consisting essentially of nucleotides encoding an HMG-CoA reductase enzyme catalytic region and at least a portion of the HMG-CoA reductase linker region; and regenerating the transformed plant.

9. A method according to claim 8, wherein the DNA construct further comprises a promoter operatively linked to said structural gene.

10. A method according to claim 9 wherein said promoter is a promoter whose regulatory function is substantially unaffected by the level of cycloartenol in said plant.

11. A method according to claim 10 wherein the promoter is the CaMV promoter.

12. A method according to claim 8 wherein the plant to be transformed is selected form the group consisting of: tobacco, tomato, corn, carrot, soybean, cotton, barley, arabidopsis, guayule, and petunia.

13. A method according to claim 9 wherein the DNA construct is plasmid HMGRΔ227-pKYLX71.

14. A transformed plant which overaccumulates sterols relative to a native, untransformed plant, wherein said transformed plant has a total sterol level of about twice that found in a native, untransformed plant and said transformed plant also has a increased cycloartenol level relative to that found in a native, untransformed plant, said transformed plant containing a genome comprising a DNA construct comprising a structural gene, said structural gene consisting essentially of nucleotides encoding an HMG-CoA reductase enzyme catalytic region and at least a portion of the HMG-CoA reductase linker region.

15. A plant according to claim 14 wherein said cycloartenol level is at least about ten times greater than that found in a native, untransformed plant.

16. A transformed plant according to claim 14 wherein the DNA construct is from plasmid HMGRΔ227-pKYLX71.

17. A plant according to claim 14 which is selected from the group consisting of: tobacco, tomato, corn, carrot, soybean, cotton, barley, arabidopsis, guayule, and petunia.

18. A seed which germinates into a transformed plant wherein said transformed plant has a total sterol level of about twice that found in native, untransformed plant and said transformed plant has an increased cycloartenol level relative to that found in a native, untransformed plant; said transformed plant containing a genome comprising a DNA construct comprising a structural gene, said structural gene consisting essentially of nucleotides encoding an HMG-CoA reductase enzyme catalytic region and at least a portion of the HMG-CoA reductase linker region.

19. A seed according to claim 18, wherein the cycloartenol level is at least about ten times greater than that found in a native, untransformed plant.

20. A seed according to claim 18 which is selected from the group consisting of: tobacco, tomato, corn, carrot, soybean, cotton, barley, arabidopsis, guayule, and petunia.

21. A seed according to claim 18 wherein the DNA construct is from plasmid HMGRΔ227-pKYLX71.

22. A seed designated ATCC 40904.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4768 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 164..2827

( x i ) SEQUENCE DESCRIPTION: SEQ ID NO:1:

```
TGTATGTCTT  GTCTTTCTCC  TAAGGGGCGT  AGGCTCATTG  ATAACTCATG  TCCTCACCTT         60

GCACTCCTTT  TGGAATTATT  TGGTTTGAGT  GAAGAAGACC  GGACCTTCGA  GGTTCGCAAC        120

TTAAACAATA  GACTTGTGAG  GATCCAGGGA  CCGAGTGGCT  ACA ATG TTG TCA CGA           175
                                                 Met Leu Ser Arg
                                                  1

CTT TTC CGT ATG CAT GGC CTC TTT GTG GCC TCC CAT CCC TGG GAA GTT              223
Leu Phe Arg Met His Gly Leu Phe Val Ala Ser His Pro Trp Glu Val
  5              10                  15                  20

ATT GTG GGG ACG GTG ACA CTT ACC ATC TGT ATG ATG TCC ATG AAC ATG              271
Ile Val Gly Thr Val Thr Leu Thr Ile Cys Met Met Ser Met Asn Met
                 25                  30                  35

TTC ACT GGC AAC AAC AAG ATC TGT GGT TGG AAT TAC GAG TGC CCA AAA              319
Phe Thr Gly Asn Asn Lys Ile Cys Gly Trp Asn Tyr Glu Cys Pro Lys
             40                  45                  50

TTT GAG GAG GAT GTA TTG AGC AGT GAC ATC ATC ATC CTC ACC ATA ACA              367
Phe Glu Glu Asp Val Leu Ser Ser Asp Ile Ile Ile Leu Thr Ile Thr
                 55                  60                  65

CGG TGC ATC GCC ATC CTG TAC ATT TAC TTC CAG TTC CAG AAC TTA CGT              415
Arg Cys Ile Ala Ile Leu Tyr Ile Tyr Phe Gln Phe Gln Asn Leu Arg
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 70  |     |     |     | 75  |     |     |     |     | 80  |     |     |     |     |      |
| CAG | CTT | GGG | TCG | AAG | TAT | ATT | TTA | GGT | ATT | GCT | GGC | CTG | TTC | ACA | ATT | 463  |
| Gln | Leu | Gly | Ser | Lys | Tyr | Ile | Leu | Gly | Ile | Ala | Gly | Leu | Phe | Thr | Ile |      |
| 85  |     |     |     | 90  |     |     |     |     | 95  |     |     |     |     | 100 |     |      |
| TTC | TCA | AGT | TTT | GTC | TTT | AGT | ACA | GTC | GTC | ATT | CAC | TTC | TTA | GAC | AAA | 511  |
| Phe | Ser | Ser | Phe | Val | Phe | Ser | Thr | Val | Val | Ile | His | Phe | Leu | Asp | Lys |      |
|     |     |     |     | 105 |     |     |     |     | 110 |     |     |     |     | 115 |     |      |
| GAA | CTG | ACG | GGC | TTA | AAT | GAA | GCT | TTG | CCC | TTT | TTC | CTG | CTT | TTG | ATT | 559  |
| Glu | Leu | Thr | Gly | Leu | Asn | Glu | Ala | Leu | Pro | Phe | Phe | Leu | Leu | Leu | Ile |      |
|     |     |     | 120 |     |     |     |     | 125 |     |     |     |     | 130 |     |     |      |
| GAC | CTT | TCT | AGA | GCG | AGT | GCA | CTA | GCA | AAG | TTT | GCC | CTA | AGT | TCA | AAC | 607  |
| Asp | Leu | Ser | Arg | Ala | Ser | Ala | Leu | Ala | Lys | Phe | Ala | Leu | Ser | Ser | Asn |      |
|     |     | 135 |     |     |     |     | 140 |     |     |     |     | 145 |     |     |     |      |
| TCT | CAG | GAT | GAA | GTA | AGG | GAA | AAT | ATA | GCT | CGC | GGA | ATG | GCA | ATT | CTG | 655  |
| Ser | Gln | Asp | Glu | Val | Arg | Glu | Asn | Ile | Ala | Arg | Gly | Met | Ala | Ile | Leu |      |
|     | 150 |     |     |     |     | 155 |     |     |     |     | 160 |     |     |     |     |      |
| GGC | CCC | ACA | TTC | ACC | CTT | GAT | GCT | CTT | GTG | GAA | TGT | CTT | GTA | ATT | GGA | 703  |
| Gly | Pro | Thr | Phe | Thr | Leu | Asp | Ala | Leu | Val | Glu | Cys | Leu | Val | Ile | Gly |      |
| 165 |     |     |     |     | 170 |     |     |     |     | 175 |     |     |     |     | 180 |      |
| GTT | GGC | ACC | ATG | TCA | GGG | GTG | CGT | CAG | CTT | GAA | ATC | ATG | TGC | TGC | TTT | 751  |
| Val | Gly | Thr | Met | Ser | Gly | Val | Arg | Gln | Leu | Glu | Ile | Met | Cys | Cys | Phe |      |
|     |     |     |     | 185 |     |     |     |     | 190 |     |     |     |     | 195 |     |      |
| GGC | TGC | ATG | TCT | GTG | CTT | GCC | AAC | TAC | TTC | GTG | TTC | ATG | ACA | TTT | TTC | 799  |
| Gly | Cys | Met | Ser | Val | Leu | Ala | Asn | Tyr | Phe | Val | Phe | Met | Thr | Phe | Phe |      |
|     |     |     | 200 |     |     |     |     | 205 |     |     |     |     | 210 |     |     |      |
| CCA | GCG | TGT | GTG | TCC | CTG | GTC | CTT | GAG | CTT | TCT | CGG | GAA | AGT | CGA | GAG | 847  |
| Pro | Ala | Cys | Val | Ser | Leu | Val | Leu | Glu | Leu | Ser | Arg | Glu | Ser | Arg | Glu |      |
|     |     | 215 |     |     |     |     | 220 |     |     |     |     | 225 |     |     |     |      |
| GGT | CGT | CCA | ATT | TGG | CAG | CTT | AGC | CAT | TTT | GCC | CGA | GTT | TTG | GAA | GAA | 895  |
| Gly | Arg | Pro | Ile | Trp | Gln | Leu | Ser | His | Phe | Ala | Arg | Val | Leu | Glu | Glu |      |
|     | 230 |     |     |     |     | 235 |     |     |     |     | 240 |     |     |     |     |      |
| GAA | GAG | AAT | AAA | CCA | AAC | CCT | GTA | ACC | CAA | AGG | GTC | AAG | ATG | ATT | ATG | 943  |
| Glu | Glu | Asn | Lys | Pro | Asn | Pro | Val | Thr | Gln | Arg | Val | Lys | Met | Ile | Met |      |
| 245 |     |     |     |     | 250 |     |     |     |     | 255 |     |     |     |     | 260 |      |
| TCT | TTA | GGT | TTG | GTT | CTT | GTT | CAT | GCT | CAC | AGT | CGA | TGG | ATA | GCT | GAT | 991  |
| Ser | Leu | Gly | Leu | Val | Leu | Val | His | Ala | His | Ser | Arg | Trp | Ile | Ala | Asp |      |
|     |     |     |     | 265 |     |     |     |     | 270 |     |     |     |     | 275 |     |      |
| CCT | TCC | CCT | CAG | AAT | AGC | ACA | ACA | GAA | CAT | TCT | AAA | GTC | TCC | TTG | GGA | 1039 |
| Pro | Ser | Pro | Gln | Asn | Ser | Thr | Thr | Glu | His | Ser | Lys | Val | Ser | Leu | Gly |      |
|     |     |     | 280 |     |     |     |     | 285 |     |     |     |     | 290 |     |     |      |
| CTG | GAT | GAA | GAT | GTG | TCC | AAG | AGA | ATT | GAA | CCA | AGT | GTT | TCT | CTC | TGG | 1087 |
| Leu | Asp | Glu | Asp | Val | Ser | Lys | Arg | Ile | Glu | Pro | Ser | Val | Ser | Leu | Trp |      |
|     |     | 295 |     |     |     |     | 300 |     |     |     |     | 305 |     |     |     |      |
| CAG | TTT | TAT | CTC | TCC | AAG | ATG | ATC | AGC | ATG | GAC | ATT | GAA | CAA | GTG | GTT | 1135 |
| Gln | Phe | Tyr | Leu | Ser | Lys | Met | Ile | Ser | Met | Asp | Ile | Glu | Gln | Val | Val |      |
|     | 310 |     |     |     |     | 315 |     |     |     |     | 320 |     |     |     |     |      |
| ACC | CTG | AGC | TTA | GCT | TTT | CTG | TTG | GCT | GTC | AAG | TAC | ATT | TTC | TTT | GAA | 1183 |
| Thr | Leu | Ser | Leu | Ala | Phe | Leu | Leu | Ala | Val | Lys | Tyr | Ile | Phe | Phe | Glu |      |
| 325 |     |     |     |     | 330 |     |     |     |     | 335 |     |     |     |     | 340 |      |
| CAA | GCA | GAG | ACA | GAG | TCC | ACA | CTG | TCT | TTA | AAA | AAT | CCT | ATC | ACG | TCT | 1231 |
| Gln | Ala | Glu | Thr | Glu | Ser | Thr | Leu | Ser | Leu | Lys | Asn | Pro | Ile | Thr | Ser |      |
|     |     |     |     | 345 |     |     |     |     | 350 |     |     |     |     | 355 |     |      |
| CCT | GTC | GTG | ACC | CCA | AAG | AAA | GCT | CCA | GAC | AAC | TGT | TGT | AGA | CGG | GAG | 1279 |
| Pro | Val | Val | Thr | Pro | Lys | Lys | Ala | Pro | Asp | Asn | Cys | Cys | Arg | Arg | Glu |      |
|     |     |     | 360 |     |     |     |     | 365 |     |     |     |     | 370 |     |     |      |
| CCT | CTG | CTT | GTG | AGA | AGG | AGC | GAG | AAG | CTT | TCA | TCG | GTT | GAG | GAG | GAG | 1327 |
| Pro | Leu | Leu | Val | Arg | Arg | Ser | Glu | Lys | Leu | Ser | Ser | Val | Glu | Glu | Glu |      |
|     |     | 375 |     |     |     |     | 380 |     |     |     |     | 385 |     |     |     |      |
| CCT | GGG | GTG | AGC | CAA | GAT | AGA | AAA | GTT | GAG | GTT | ATA | AAA | CCA | TTA | GTG | 1375 |
| Pro | Gly | Val | Ser | Gln | Asp | Arg | Lys | Val | Glu | Val | Ile | Lys | Pro | Leu | Val |      |
|     | 390 |     |     |     |     | 395 |     |     |     |     | 400 |     |     |     |     |      |

| | | | | | | | | | | | | | | | | |
|---|---|---|---|---|---|---|---|---|---|---|---|---|---|---|---|---|
| GTG | GAA | ACT | GAG | AGT | GCA | AGC | AGA | GCT | ACA | TTT | GTG | CTT | GGC | GCC | TCT | 1423 |
| Val | Glu | Thr | Glu | Ser | Ala | Ser | Arg | Ala | Thr | Phe | Val | Leu | Gly | Ala | Ser | |
| 405 | | | | 410 | | | | | 415 | | | | | 420 | | |
| GGG | ACC | AGC | CCT | CCA | GTG | GCA | GCG | AGG | ACA | CAG | GAG | CTT | GAA | ATT | GAA | 1471 |
| Gly | Thr | Ser | Pro | Pro | Val | Ala | Ala | Arg | Thr | Gln | Glu | Leu | Glu | Ile | Glu | |
| | | | | 425 | | | | 430 | | | | | 435 | | | |
| CTC | CCC | AGT | GAG | CCT | CGG | CCT | AAT | GAA | GAA | TGT | CTG | CAG | ATA | CTG | GAG | 1519 |
| Leu | Pro | Ser | Glu | Pro | Arg | Pro | Asn | Glu | Glu | Cys | Leu | Gln | Ile | Leu | Glu | |
| | | | 440 | | | | | 445 | | | | | 450 | | | |
| AGT | GCC | GAG | AAA | GGT | GCA | AAG | TTC | CTT | AGC | GAT | GCA | GAG | ATC | ATC | CAG | 1567 |
| Ser | Ala | Glu | Lys | Gly | Ala | Lys | Phe | Leu | Ser | Asp | Ala | Glu | Ile | Ile | Gln | |
| | | 455 | | | | | 460 | | | | | 465 | | | | |
| TTG | GTC | AAT | GCC | AAG | CAC | ATC | CCA | GCC | TAC | AAA | TTG | GAA | ACC | TTA | ATG | 1615 |
| Leu | Val | Asn | Ala | Lys | His | Ile | Pro | Ala | Tyr | Lys | Leu | Glu | Thr | Leu | Met | |
| | 470 | | | | 475 | | | | | 480 | | | | | | |
| GAA | ACT | CAT | GAA | CGT | GGT | GTA | TCT | ATT | CGC | CGG | CAG | CTC | CTC | TCC | ACA | 1663 |
| Glu | Thr | His | Glu | Arg | Gly | Val | Ser | Ile | Arg | Arg | Gln | Leu | Leu | Ser | Thr | |
| 485 | | | | 490 | | | | | 495 | | | | | 500 | | |
| AAG | CTT | CCA | GAG | CCT | TCT | TCT | CTG | CAG | TAC | CTG | CCT | TAC | AGA | GAT | TAT | 1711 |
| Lys | Leu | Pro | Glu | Pro | Ser | Ser | Leu | Gln | Tyr | Leu | Pro | Tyr | Arg | Asp | Tyr | |
| | | | | 505 | | | | 510 | | | | | 515 | | | |
| AAT | TAT | TCC | CTG | GTG | ATG | GGA | GCT | TGC | TGT | GAG | AAT | GTG | ATC | GGA | TAT | 1759 |
| Asn | Tyr | Ser | Leu | Val | Met | Gly | Ala | Cys | Cys | Glu | Asn | Val | Ile | Gly | Tyr | |
| | | | 520 | | | | | 525 | | | | | 530 | | | |
| ATG | CCC | ATC | CCT | GTC | GGA | GTA | GCA | GGG | CCT | CTG | TGC | CTG | GAT | GGT | AAA | 1807 |
| Met | Pro | Ile | Pro | Val | Gly | Val | Ala | Gly | Pro | Leu | Cys | Leu | Asp | Gly | Lys | |
| | | 535 | | | | | 540 | | | | | 545 | | | | |
| GAG | TAC | CAG | GTT | CCA | ATG | GCA | ACA | ACG | GAA | GGC | TGT | CTG | GTG | GCC | AGC | 1855 |
| Glu | Tyr | Gln | Val | Pro | Met | Ala | Thr | Thr | Glu | Gly | Cys | Leu | Val | Ala | Ser | |
| | 550 | | | | | 555 | | | | | 560 | | | | | |
| ACC | AAC | AGA | GGC | TGC | AGG | GCA | ATA | GGT | CTT | GGT | GGA | GGT | GCC | AGC | AGC | 1903 |
| Thr | Asn | Arg | Gly | Cys | Arg | Ala | Ile | Gly | Leu | Gly | Gly | Gly | Ala | Ser | Ser | |
| 565 | | | | 570 | | | | | 575 | | | | | 580 | | |
| CGG | GTC | CTT | GCA | GAT | GGG | ATG | ACC | CGG | GGC | CCA | GTG | GTG | CGT | CTT | CCT | 1951 |
| Arg | Val | Leu | Ala | Asp | Gly | Met | Thr | Arg | Gly | Pro | Val | Val | Arg | Leu | Pro | |
| | | | 585 | | | | | 590 | | | | | 595 | | | |
| CGT | GCT | TGT | GAT | TCT | GCA | GAA | GTG | AAG | GCC | TGG | CTT | GAA | ACA | CCC | GAA | 1999 |
| Arg | Ala | Cys | Asp | Ser | Ala | Glu | Val | Lys | Ala | Trp | Leu | Glu | Thr | Pro | Glu | |
| | | | 600 | | | | | 605 | | | | | 610 | | | |
| GGG | TTT | GCG | GTG | ATA | AAG | GAC | GCC | TTC | GAT | AGC | ACT | AGC | AGA | TTT | GCA | 2047 |
| Gly | Phe | Ala | Val | Ile | Lys | Asp | Ala | Phe | Asp | Ser | Thr | Ser | Arg | Phe | Ala | |
| | | 615 | | | | | 620 | | | | | 625 | | | | |
| CGT | CTA | CAG | AAG | CTT | CAT | GTG | ACC | ATG | GCA | GGG | CGC | AAC | CTG | TAC | ATC | 2095 |
| Arg | Leu | Gln | Lys | Leu | His | Val | Thr | Met | Ala | Gly | Arg | Asn | Leu | Tyr | Ile | |
| | 630 | | | | | 635 | | | | | 640 | | | | | |
| CGT | TTC | CAG | TCC | AAG | ACA | GGG | GAT | GCC | ATG | GGG | ATG | AAC | ATG | ATT | TCC | 2143 |
| Arg | Phe | Gln | Ser | Lys | Thr | Gly | Asp | Ala | Met | Gly | Met | Asn | Met | Ile | Ser | |
| 645 | | | | 650 | | | | | 655 | | | | | 660 | | |
| AAG | GGC | ACT | GAG | AAA | GCA | CTT | CTG | AAG | CTT | CAG | GAG | TTC | TTT | CCT | GAA | 2191 |
| Lys | Gly | Thr | Glu | Lys | Ala | Leu | Leu | Lys | Leu | Gln | Glu | Phe | Phe | Pro | Glu | |
| | | | | 665 | | | | 670 | | | | | 675 | | | |
| ATG | CAG | ATT | CTG | GCA | GTT | AGT | GGT | AAC | TAC | TGC | ACT | GAC | AAG | AAA | CCT | 2239 |
| Met | Gln | Ile | Leu | Ala | Val | Ser | Gly | Asn | Tyr | Cys | Thr | Asp | Lys | Lys | Pro | |
| | | | 680 | | | | | 685 | | | | | 690 | | | |
| GCC | GCC | ATA | AAC | TGG | ATC | GAG | GGA | AGA | GGA | AAG | ACA | GTT | GTG | TGT | GAA | 2287 |
| Ala | Ala | Ile | Asn | Trp | Ile | Glu | Gly | Arg | Gly | Lys | Thr | Val | Val | Cys | Glu | |
| | | 695 | | | | | 700 | | | | | 705 | | | | |
| GCT | GTT | ATT | CCA | GCC | AAG | GTG | GTG | AGA | GAA | GTA | TTA | AAG | ACA | ACT | ACG | 2335 |
| Ala | Val | Ile | Pro | Ala | Lys | Val | Val | Arg | Glu | Val | Leu | Lys | Thr | Thr | Thr | |
| | 710 | | | | | 715 | | | | | 720 | | | | | |
| GAA | GCT | ATG | ATT | GAC | GTA | AAC | ATT | AAC | AAG | AAT | CTT | GTG | GGT | TCT | GCC | 2383 |
| Glu | Ala | Met | Ile | Asp | Val | Asn | Ile | Asn | Lys | Asn | Leu | Val | Gly | Ser | Ala | |

-continued

```
   725                          730                          735                          740
ATG GCT GGG AGC ATA GGA GGC TAC AAT GCC CAT GCA GCA AAC ATC GTC                              2431
Met Ala Gly Ser Ile Gly Gly Tyr Asn Ala His Ala Ala Asn Ile Val
                745                          750                          755

ACT GCT ATC TAC ATT GCA TGT GGC CAG GAT GCA GCA CAG AAT GTG GGG                              2479
Thr Ala Ile Tyr Ile Ala Cys Gly Gln Asp Ala Ala Gln Asn Val Gly
                760                          765                          770

AGT TCA AAC TGT ATT ACT TTA ATG GAA GCA AGT GGT CCC ACG AAT GAA                              2527
Ser Ser Asn Cys Ile Thr Leu Met Glu Ala Ser Gly Pro Thr Asn Glu
                775                          780                          785

GAC TTG TAT ATC AGC TGC ACC ATG CCA TCT ATA GAG ATA GGA ACT GTG                              2575
Asp Leu Tyr Ile Ser Cys Thr Met Pro Ser Ile Glu Ile Gly Thr Val
                790                          795                          800

GGT GGT GGG ACC AAC CTC CTA CCA CAG CAG GCC TGT CTG CAG ATG CTA                              2623
Gly Gly Gly Thr Asn Leu Leu Pro Gln Gln Ala Cys Leu Gln Met Leu
805                          810                          815                          820

GGT GTT CAA GGA GCG TGC AAA GAC AAT CCT GGA GAA AAT GCA CGG CAA                              2671
Gly Val Gln Gly Ala Cys Lys Asp Asn Pro Gly Glu Asn Ala Arg Gln
                825                          830                          835

CTT GCC CGA ATT GTG TGT GGT ACT GTA ATG GCT GGG GAG TTG TCC TTG                              2719
Leu Ala Arg Ile Val Cys Gly Thr Val Met Ala Gly Glu Leu Ser Leu
                840                          845                          850

ATG GCA GCA TTG GCA GCA GGA CAT CTT GTT AGA AGT CAC ATG GTT CAT                              2767
Met Ala Ala Leu Ala Ala Gly His Leu Val Arg Ser His Met Val His
                855                          860                          865

AAC AGA TCG AAG ATA AAT TTA CAA GAT CTG CAA GGA ACG TGC ACC AAG                              2815
Asn Arg Ser Lys Ile Asn Leu Gln Asp Leu Gln Gly Thr Cys Thr Lys
        870                          875                          880

AAG TCA GCT TGAGCAGCCT GACAGTATTG AACTGAAACA CGGGCATTGG                                      2864
Lys Ser Ala
885

GTTCTCAAGG ACTAACATGA AATCTGTGAA TTAAAAATCT CAATGCAGTG TCTTGTGGAA                            2924

GATGAATGAA CGTGATCAGT GAGACGCCTG CTTGGTTTCT GGCTCTTTCA GAGACGTCTG                            2984

AGGTCCTTTG CTCGGAGACT CCTCAGATCT GGAAACAGTG TGGTCCTTCC CATGCTGTAT                            3044

TCTGAAAAGA TCTCATATGG ATGTTGTGCT CTGAGCACCA CAGATGTGAT CTGCAGCTCG                            3104

TTTCTGAAAT GATGGAGTTC ATGGTGATCA GTGTGAGACT GGCCTCTCCC AGCAGGTTAA                            3164

AAATGGAGTT TTAAATTATA CTGTAGCTGA CAGTACTTCT GATTTTATAT TTATTTAGTC                            3224

TGAGTTGTAG AACTTTGCAA TCTAAGTTTA TTTTTTGTAA CCTAATAATT CATTTGGTGC                            3284

TGGTCTATTG ATTTTTGGGG GTAAACAATA TTATTCTTCA GAAGGGGACC TACTTCTTCA                            3344

TGGGAAGAAT TACTTTTATT CTCAAACTAC AGAACAATGT GCTAAGCAGT GCTAAATTGT                            3404

TCTCATGAAG AAAACAGTCA CTGCATTTAT CTCTGTAGGC CTTTTTTCAG AGAGGCCTTG                            3464

TCTAGATTTT TGCCAGCTAG GCTACTGCAT GTCTTAGTGT CAGGCCTTAG GAAAGTGCCA                            3524

CGCTCTGCAC TAAAGATATC AGAGCTCTTG GTGTTACTTA GACAAGAGTA TGAGCAAGTC                            3584

GGACCTCTCA GAGTGTGGGA ACACAGTTTT GAAAGAAAAA CCATTTCTCT AAGCCAATTT                            3644

TCTTTAAAGA CATTTTAACT TATTTAGCTG AGTTCTAGAT TTTTCGGGTA AACTATCAAA                            3704

TCTGTATATG TTGTAATAAA GTGTCTTATG CTAGGAGTTT ATTCAAAGTG TTTAAGTAAT                            3764

AAAAGGACTC AAATTTACAC TGATAAAATA CTCTAGCTTG GGCCAGAGAA GACAGTGCTC                            3824

ATTAGCGTTG TCCAGGAAAC CCTGCTTGCT TGCCAAGCCT AATGAAGGGA AAGTCAGCTT                            3884

TCAGAGCCAA TGATGGAGGC CACATGAATG GCCCTGGAGC TGTGTGCCTT GTTCTGTGGC                            3944

CAGGAGCTTG GTGACTGAAT CATTTACGGG CTCCTTTGAT GGACCCATAA AAGCTCTTAG                            4004

CTTCCTCAGG GGGTCAGCAG AGTTGTTGAA TCTTAATTTT TTTTTAATG TACCAGTTTT                             4064
```

```
GTATAAATAA TAATAAAGAG CTCCTTATTT TGTATTCTAT CTAATGCTTC GAGTTCAGTC     4124

TTGGGAAGCT GACATCTCAT GTAGAAGATG GACTCTGAAA GACATTCCAA GAGTGCAGCG     4184

GCATCATGGG AGCCTCTTAG TGATTGTGTG TCAGTATTAT TGTGGAAGAT TGACTTTGCT     4244

TTTGTATGTG AAGTTTCAGA TTGCTCCTCT TGTGACTTTT TAGCCAGTAA CATTTTATTT     4304

ACCTGAGCTT GTCATGGAAG TGGCAGTGAA AAGTATTGAG TATTCATGCT GGTGACTGTA     4364

ACCAATGTCA TCTTGCTAAA AACTCATGTT TTGTACAATT ACTAAATTGT ATACATTTTG     4424

TTATAGAATA CTTTTTCCAG TTGAGTAAAT TATGAAAGGA AGTTAACATT AACAGGTGTA     4484

AGCGGTGGCT TTTTTAAAAT GAAGGATTAA CCCTAAGCCC GAGACCCAGA AGCTAGCAAA     4544

GTCTGGCAGA GTGGTAAACT GTCCTGCTGG GGCCATCCAA TCATCTCTCT CCATTACACT     4604

TTCTAACTTT GCAGCATTGG TGCTGGCCAG TGTATTGTTT CATTGATCTT CCTTACGCTT     4664

AGAGGGTTTG ATTGGTTCAG ATCTATAATC TCAGCCACAT TGTCTTGGTA TCAGCTGGAG     4724

AGAGTTAAGA GGAAGGGAAA ATAAAGTTCA GATAGCCAAA ACAC                     4768
```

( 2 ) INFORMATION FOR SEQ ID NO:2:

( i ) SEQUENCE CHARACTERISTICS:
      ( A ) LENGTH: 887 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

```
Met Leu Ser Arg Leu Phe Arg Met His Gly Leu Phe Val Ala Ser His
 1               5                  10                  15

Pro Trp Glu Val Ile Val Gly Thr Val Thr Leu Thr Ile Cys Met Met
                20                  25                  30

Ser Met Asn Met Phe Thr Gly Asn Asn Lys Ile Cys Gly Trp Asn Tyr
            35                  40                  45

Glu Cys Pro Lys Phe Glu Glu Asp Val Leu Ser Ser Asp Ile Ile Ile
        50                  55                  60

Leu Thr Ile Thr Arg Cys Ile Ala Ile Leu Tyr Ile Tyr Phe Gln Phe
 65                  70                  75                  80

Gln Asn Leu Arg Gln Leu Gly Ser Lys Tyr Ile Leu Gly Ile Ala Gly
                85                  90                  95

Leu Phe Thr Ile Phe Ser Ser Phe Val Phe Ser Thr Val Val Ile His
                100                 105                 110

Phe Leu Asp Lys Glu Leu Thr Gly Leu Asn Glu Ala Leu Pro Phe Phe
            115                 120                 125

Leu Leu Leu Ile Asp Leu Ser Arg Ala Ser Ala Leu Ala Lys Phe Ala
        130                 135                 140

Leu Ser Ser Asn Ser Gln Asp Glu Val Arg Glu Asn Ile Ala Arg Gly
145                 150                 155                 160

Met Ala Ile Leu Gly Pro Thr Phe Thr Leu Asp Ala Leu Val Glu Cys
                165                 170                 175

Leu Val Ile Gly Val Gly Thr Met Ser Gly Val Arg Gln Leu Glu Ile
                180                 185                 190

Met Cys Cys Phe Gly Cys Met Ser Val Leu Ala Asn Tyr Phe Val Phe
            195                 200                 205

Met Thr Phe Phe Pro Ala Cys Val Ser Leu Val Leu Glu Leu Ser Arg
        210                 215                 220

Glu Ser Arg Glu Gly Arg Pro Ile Trp Gln Leu Ser His Phe Ala Arg
225                 230                 235                 240

Val Leu Glu Glu Glu Glu Asn Lys Pro Asn Pro Val Thr Gln Arg Val
```

-continued

|   |   |   |   |   | 245 |   |   |   |   | 250 |   |   |   |   | 255 |   |
|---|---|---|---|---|---|---|---|---|---|---|---|---|---|---|---|---|
| Lys | Met | Ile | Met | Ser | Leu | Gly | Leu | Val | Leu | Val | His | Ala | His | Ser | Arg |
|   |   |   | 260 |   |   |   | 265 |   |   |   |   | 270 |   |   |   |
| Trp | Ile | Ala | Asp | Pro | Ser | Pro | Gln | Asn | Ser | Thr | Thr | Glu | His | Ser | Lys |
|   |   |   | 275 |   |   |   | 280 |   |   |   |   | 285 |   |   |   |
| Val | Ser | Leu | Gly | Leu | Asp | Glu | Asp | Val | Ser | Lys | Arg | Ile | Glu | Pro | Ser |
|   |   | 290 |   |   |   | 295 |   |   |   |   | 300 |   |   |   |   |
| Val | Ser | Leu | Trp | Gln | Phe | Tyr | Leu | Ser | Lys | Met | Ile | Ser | Met | Asp | Ile |
|   | 305 |   |   |   | 310 |   |   |   |   | 315 |   |   |   |   | 320 |
| Glu | Gln | Val | Val | Thr | Leu | Ser | Leu | Ala | Phe | Leu | Leu | Ala | Val | Lys | Tyr |
|   |   |   |   | 325 |   |   |   |   | 330 |   |   |   |   | 335 |   |
| Ile | Phe | Phe | Glu | Gln | Ala | Glu | Thr | Glu | Ser | Thr | Leu | Ser | Leu | Lys | Asn |
|   |   |   | 340 |   |   |   |   | 345 |   |   |   |   | 350 |   |   |
| Pro | Ile | Thr | Ser | Pro | Val | Val | Thr | Pro | Lys | Lys | Ala | Pro | Asp | Asn | Cys |
|   |   |   | 355 |   |   |   |   | 360 |   |   |   | 365 |   |   |   |
| Cys | Arg | Arg | Glu | Pro | Leu | Leu | Val | Arg | Arg | Ser | Glu | Lys | Leu | Ser | Ser |
|   |   | 370 |   |   |   | 375 |   |   |   |   | 380 |   |   |   |   |
| Val | Glu | Glu | Glu | Pro | Gly | Val | Ser | Gln | Asp | Arg | Lys | Val | Glu | Val | Ile |
|   | 385 |   |   |   | 390 |   |   |   |   | 395 |   |   |   |   | 400 |
| Lys | Pro | Leu | Val | Val | Glu | Thr | Glu | Ser | Ala | Ser | Arg | Ala | Thr | Phe | Val |
|   |   |   |   | 405 |   |   |   |   | 410 |   |   |   |   | 415 |   |
| Leu | Gly | Ala | Ser | Gly | Thr | Ser | Pro | Pro | Val | Ala | Ala | Arg | Thr | Gln | Glu |
|   |   |   | 420 |   |   |   |   | 425 |   |   |   |   | 430 |   |   |
| Leu | Glu | Ile | Glu | Leu | Pro | Ser | Glu | Pro | Arg | Pro | Asn | Glu | Glu | Cys | Leu |
|   |   | 435 |   |   |   |   | 440 |   |   |   |   | 445 |   |   |   |
| Gln | Ile | Leu | Glu | Ser | Ala | Glu | Lys | Gly | Ala | Lys | Phe | Leu | Ser | Asp | Ala |
|   | 450 |   |   |   |   | 455 |   |   |   |   | 460 |   |   |   |   |
| Glu | Ile | Ile | Gln | Leu | Val | Asn | Ala | Lys | His | Ile | Pro | Ala | Tyr | Lys | Leu |
| 465 |   |   |   |   | 470 |   |   |   |   | 475 |   |   |   |   | 480 |
| Glu | Thr | Leu | Met | Glu | Thr | His | Glu | Arg | Gly | Val | Ser | Ile | Arg | Arg | Gln |
|   |   |   |   | 485 |   |   |   |   | 490 |   |   |   |   | 495 |   |
| Leu | Leu | Ser | Thr | Lys | Leu | Pro | Glu | Pro | Ser | Ser | Leu | Gln | Tyr | Leu | Pro |
|   |   |   | 500 |   |   |   |   | 505 |   |   |   |   | 510 |   |   |
| Tyr | Arg | Asp | Tyr | Asn | Tyr | Ser | Leu | Val | Met | Gly | Ala | Cys | Cys | Glu | Asn |
|   |   |   | 515 |   |   |   |   | 520 |   |   |   | 525 |   |   |   |
| Val | Ile | Gly | Tyr | Met | Pro | Ile | Pro | Val | Gly | Val | Ala | Gly | Pro | Leu | Cys |
|   |   |   | 530 |   |   |   | 535 |   |   |   |   | 540 |   |   |   |
| Leu | Asp | Gly | Lys | Glu | Tyr | Gln | Val | Pro | Met | Ala | Thr | Thr | Glu | Gly | Cys |
| 545 |   |   |   |   | 550 |   |   |   |   | 555 |   |   |   |   | 560 |
| Leu | Val | Ala | Ser | Thr | Asn | Arg | Gly | Cys | Arg | Ala | Ile | Gly | Leu | Gly | Gly |
|   |   |   |   | 565 |   |   |   |   | 570 |   |   |   |   | 575 |   |
| Gly | Ala | Ser | Ser | Arg | Val | Leu | Ala | Asp | Gly | Met | Thr | Arg | Gly | Pro | Val |
|   |   |   | 580 |   |   |   |   | 585 |   |   |   |   | 590 |   |   |
| Val | Arg | Leu | Pro | Arg | Ala | Cys | Asp | Ser | Ala | Glu | Val | Lys | Ala | Trp | Leu |
|   |   |   | 595 |   |   |   |   | 600 |   |   |   |   | 605 |   |   |
| Glu | Thr | Pro | Glu | Gly | Phe | Ala | Val | Ile | Lys | Asp | Ala | Phe | Asp | Ser | Thr |
|   |   | 610 |   |   |   |   | 615 |   |   |   |   | 620 |   |   |   |
| Ser | Arg | Phe | Ala | Arg | Leu | Gln | Lys | Leu | His | Val | Thr | Met | Ala | Gly | Arg |
| 625 |   |   |   |   | 630 |   |   |   |   | 635 |   |   |   |   | 640 |
| Asn | Leu | Tyr | Ile | Arg | Phe | Gln | Ser | Lys | Thr | Gly | Asp | Ala | Met | Gly | Met |
|   |   |   |   | 645 |   |   |   |   | 650 |   |   |   |   | 655 |   |
| Asn | Met | Ile | Ser | Lys | Gly | Thr | Glu | Lys | Ala | Leu | Leu | Lys | Leu | Gln | Glu |
|   |   |   | 660 |   |   |   |   | 665 |   |   |   |   | 670 |   |   |
| Phe | Phe | Pro | Glu | Met | Gln | Ile | Leu | Ala | Val | Ser | Gly | Asn | Tyr | Cys | Thr |
|   |   |   | 675 |   |   |   |   | 680 |   |   |   | 685 |   |   |   |

| | | | | | | | | | | | | | | |
|---|---|---|---|---|---|---|---|---|---|---|---|---|---|---|
| Asp | Lys | Lys | Pro | Ala | Ala | Ile | Asn | Trp | Ile | Glu | Gly | Arg | Gly | Lys | Thr |
| | 690 | | | | 695 | | | | | 700 | | | | | |
| Val | Val | Cys | Glu | Ala | Val | Ile | Pro | Ala | Lys | Val | Val | Arg | Glu | Val | Leu |
| 705 | | | | | 710 | | | | | 715 | | | | | 720 |
| Lys | Thr | Thr | Thr | Glu | Ala | Met | Ile | Asp | Val | Asn | Ile | Asn | Lys | Asn | Leu |
| | | | | 725 | | | | | 730 | | | | | 735 | |
| Val | Gly | Ser | Ala | Met | Ala | Gly | Ser | Ile | Gly | Gly | Tyr | Asn | Ala | His | Ala |
| | | | 740 | | | | | 745 | | | | | 750 | | |
| Ala | Asn | Ile | Val | Thr | Ala | Ile | Tyr | Ile | Ala | Cys | Gly | Gln | Asp | Ala | Ala |
| | | 755 | | | | | 760 | | | | | 765 | | | |
| Gln | Asn | Val | Gly | Ser | Ser | Asn | Cys | Ile | Thr | Leu | Met | Glu | Ala | Ser | Gly |
| | 770 | | | | | 775 | | | | | 780 | | | | |
| Pro | Thr | Asn | Glu | Asp | Leu | Tyr | Ile | Ser | Cys | Thr | Met | Pro | Ser | Ile | Glu |
| 785 | | | | | 790 | | | | | 795 | | | | | 800 |
| Ile | Gly | Thr | Val | Gly | Gly | Gly | Thr | Asn | Leu | Leu | Pro | Gln | Gln | Ala | Cys |
| | | | | 805 | | | | | 810 | | | | | 815 | |
| Leu | Gln | Met | Leu | Gly | Val | Gln | Gly | Ala | Cys | Lys | Asp | Asn | Pro | Gly | Glu |
| | | | 820 | | | | | 825 | | | | | 830 | | |
| Asn | Ala | Arg | Gln | Leu | Ala | Arg | Ile | Val | Cys | Gly | Thr | Val | Met | Ala | Gly |
| | | 835 | | | | | 840 | | | | | 845 | | | |
| Glu | Leu | Ser | Leu | Met | Ala | Ala | Leu | Ala | Ala | Gly | His | Leu | Val | Arg | Ser |
| | 850 | | | | | 855 | | | | | 860 | | | | |
| His | Met | Val | His | Asn | Arg | Ser | Lys | Ile | Asn | Leu | Gln | Asp | Leu | Gln | Gly |
| 865 | | | | | 870 | | | | | 875 | | | | | 880 |
| Thr | Cys | Thr | Lys | Lys | Ser | Ala | | | | | | | | | |
| | | | | 885 | | | | | | | | | | | |

( 2 ) INFORMATION FOR SEQ ID NO:3:

( i ) SEQUENCE CHARACTERISTICS:
        ( A ) LENGTH: 3360 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 121..3282

( x i ) SEQUENCE DESCRIPTION: SEQ ID NO:3:

```
TTTATTAACT TATTTTTTTC TTCTTTCTAC CCAATTCTAG TCAGGAAAAG ACTAAGGGCT      60

GGAACATAGT GTATCATTGT CTAATTGTTG ATACAAAGTA GATAAATACA TAAAACAAGC     120
```

| | | | | | | | | | | | | | | | | |
|---|---|---|---|---|---|---|---|---|---|---|---|---|---|---|---|---|
| ATG | CCG | CCG | CTA | TTC | AAG | GGA | CTG | AAA | CAG | ATG | GCA | AAG | CCA | ATT | GCC | 168 |
| Met | Pro | Pro | Leu | Phe | Lys | Gly | Leu | Lys | Gln | Met | Ala | Lys | Pro | Ile | Ala | |
| 1 | | | | 5 | | | | | 10 | | | | | 15 | | |
| TAT | GTT | TCA | AGA | TTT | TCG | GCG | AAA | CGA | CCA | ATT | CAT | ATA | ATA | CTT | TTT | 216 |
| Tyr | Val | Ser | Arg | Phe | Ser | Ala | Lys | Arg | Pro | Ile | His | Ile | Ile | Leu | Phe | |
| | | | 20 | | | | | 25 | | | | | 30 | | | |
| TCT | CTA | ATC | ATA | TCC | GCA | TTC | GCT | TAT | CTA | TCC | GTC | ATT | CAG | TAT | TAC | 264 |
| Ser | Leu | Ile | Ile | Ser | Ala | Phe | Ala | Tyr | Leu | Ser | Val | Ile | Gln | Tyr | Tyr | |
| | | 35 | | | | | 40 | | | | | 45 | | | | |
| TTC | AAT | GGT | TGG | CAA | CTA | GAT | TCA | AAT | AGT | GTT | TTT | GAA | ACT | GCT | CCA | 312 |
| Phe | Asn | Gly | Trp | Gln | Leu | Asp | Ser | Asn | Ser | Val | Phe | Glu | Thr | Ala | Pro | |
| | 50 | | | | | 55 | | | | | 60 | | | | | |
| AAT | AAA | GAC | TCC | AAC | ACT | CTA | TTT | CAA | GAA | TGT | TCC | CAT | TAC | TAC | AGA | 360 |
| Asn | Lys | Asp | Ser | Asn | Thr | Leu | Phe | Gln | Glu | Cys | Ser | His | Tyr | Tyr | Arg | |
| 65 | | | | | 70 | | | | | 75 | | | | | 80 | |
| GAT | TCC | TCT | CTA | GAT | GGT | TGG | GTA | TCA | ATC | ACC | GCG | CAT | GAA | GCT | AGT | 408 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Asp | Ser | Ser | Leu | Asp | Gly | Trp | Val | Ser | Ile | Thr | Ala | His | Glu | Ala | Ser |     |
|     |     |     |     | 85  |     |     |     | 90  |     |     |     |     | 95  |     |     |     |
| GAG | TTA | CCA | GCC | CCA | CAC | CAT | TAC | TAT | CTA | TTA | AAC | CTG | AAC | TTC | AAT | 456 |
| Glu | Leu | Pro | Ala | Pro | His | His | Tyr | Tyr | Leu | Leu | Asn | Leu | Asn | Phe | Asn |     |
|     |     |     | 100 |     |     |     |     | 105 |     |     |     |     | 110 |     |     |     |
| AGT | CCT | AAT | GAA | ACT | GAC | TCC | ATT | CCA | GAA | CTA | GCT | AAC | ACG | GTT | TTT | 504 |
| Ser | Pro | Asn | Glu | Thr | Asp | Ser | Ile | Pro | Glu | Leu | Ala | Asn | Thr | Val | Phe |     |
|     |     |     | 115 |     |     |     |     | 120 |     |     |     |     | 125 |     |     |     |
| GAG | AAA | GAT | AAT | ACA | AAA | TAT | ATT | CTG | CAA | GAA | GAT | CTC | AGT | GTT | TCC | 552 |
| Glu | Lys | Asp | Asn | Thr | Lys | Tyr | Ile | Leu | Gln | Glu | Asp | Leu | Ser | Val | Ser |     |
|     |     |     | 130 |     |     |     |     | 135 |     |     |     |     | 140 |     |     |     |
| AAA | GAA | ATT | TCT | TCT | ACT | GAT | GGA | ACG | AAA | TGG | AGG | TTA | AGA | AGT | GAC | 600 |
| Lys | Glu | Ile | Ser | Ser | Thr | Asp | Gly | Thr | Lys | Trp | Arg | Leu | Arg | Ser | Asp |     |
| 145 |     |     |     |     | 150 |     |     |     |     | 155 |     |     |     |     | 160 |     |
| AGA | AAA | AGT | CTT | TTC | GAC | GTA | AAG | ACG | TTA | GCA | TAT | TCT | CTC | TAC | GAT | 648 |
| Arg | Lys | Ser | Leu | Phe | Asp | Val | Lys | Thr | Leu | Ala | Tyr | Ser | Leu | Tyr | Asp |     |
|     |     |     |     | 165 |     |     |     |     | 170 |     |     |     |     | 175 |     |     |
| GTA | TTT | TCA | GAA | AAT | GTA | ACC | CAA | GCA | GAC | CCG | TTT | GAC | GTC | CTT | ATT | 696 |
| Val | Phe | Ser | Glu | Asn | Val | Thr | Gln | Ala | Asp | Pro | Phe | Asp | Val | Leu | Ile |     |
|     |     |     |     | 180 |     |     |     |     | 185 |     |     |     |     | 190 |     |     |
| ATG | GTT | ACT | GCC | TAC | CTA | ATG | ATG | TTC | TAC | ACC | ATA | TTC | GGC | CTC | TTC | 744 |
| Met | Val | Thr | Ala | Tyr | Leu | Met | Met | Phe | Tyr | Thr | Ile | Phe | Gly | Leu | Phe |     |
|     |     |     | 195 |     |     |     |     | 200 |     |     |     |     | 205 |     |     |     |
| AAT | GAC | ATG | AGG | AAG | ACC | GGG | TCA | AAT | TTT | TGG | TTG | AGC | GCC | TCT | ACA | 792 |
| Asn | Asp | Met | Arg | Lys | Thr | Gly | Ser | Asn | Phe | Trp | Leu | Ser | Ala | Ser | Thr |     |
| 210 |     |     |     |     | 215 |     |     |     |     | 220 |     |     |     |     |     |     |
| GTG | GTC | AAT | TCT | GCA | TCA | TCA | CTT | TTC | TTA | GCA | TTG | TAT | GTC | ACC | CAA | 840 |
| Val | Val | Asn | Ser | Ala | Ser | Ser | Leu | Phe | Leu | Ala | Leu | Tyr | Val | Thr | Gln |     |
| 225 |     |     |     |     | 230 |     |     |     |     | 235 |     |     |     |     | 240 |     |
| TGT | ATT | CTA | GGC | AAA | GAA | GTT | TCC | GCA | TTA | ACT | CTT | TTT | GAA | GGT | TTG | 888 |
| Cys | Ile | Leu | Gly | Lys | Glu | Val | Ser | Ala | Leu | Thr | Leu | Phe | Glu | Gly | Leu |     |
|     |     |     |     | 245 |     |     |     |     | 250 |     |     |     |     | 255 |     |     |
| CCT | TTC | ATT | GTA | GTT | GTT | GGT | TTC | AAG | CAC | AAA | ATC | AAG | ATT | GCC |     | 936 |
| Pro | Phe | Ile | Val | Val | Val | Val | Gly | Phe | Lys | His | Lys | Ile | Lys | Ile | Ala |     |
|     |     |     | 260 |     |     |     |     | 265 |     |     |     |     | 270 |     |     |     |
| CAG | TAT | GCC | CTG | GAG | AAA | TTT | GAA | AGA | GTC | GGT | TTA | TCT | AAA | AGG | ATT | 984 |
| Gln | Tyr | Ala | Leu | Glu | Lys | Phe | Glu | Arg | Val | Gly | Leu | Ser | Lys | Arg | Ile |     |
|     |     |     | 275 |     |     |     |     | 280 |     |     |     |     | 285 |     |     |     |
| ACT | ACC | GAT | GAA | ATC | GTT | TTT | GAA | TCC | GTG | AGC | GAA | GAG | GGT | GGT | CGT | 1032 |
| Thr | Thr | Asp | Glu | Ile | Val | Phe | Glu | Ser | Val | Ser | Glu | Glu | Gly | Gly | Arg |     |
|     |     |     | 290 |     |     |     |     | 295 |     |     |     |     | 300 |     |     |     |
| TTG | ATT | CAA | GAC | CAT | TTG | CTT | TGT | ATT | TTT | GCC | TTT | ATC | GGA | TGC | TCT | 1080 |
| Leu | Ile | Gln | Asp | His | Leu | Leu | Cys | Ile | Phe | Ala | Phe | Ile | Gly | Cys | Ser |     |
| 305 |     |     |     |     | 310 |     |     |     |     | 315 |     |     |     |     | 320 |     |
| ATG | TAT | GCT | CAC | CAA | TTG | AAG | ACT | TTG | ACA | AAC | TTC | TGC | ATA | TTA | TCA | 1128 |
| Met | Tyr | Ala | His | Gln | Leu | Lys | Thr | Leu | Thr | Asn | Phe | Cys | Ile | Leu | Ser |     |
|     |     |     |     | 325 |     |     |     |     | 330 |     |     |     |     | 335 |     |     |
| GCA | TTT | ATC | CTA | ATT | TTT | GAA | TTG | ATT | TTA | ACT | CCT | ACA | TTT | TAT | TCT | 1176 |
| Ala | Phe | Ile | Leu | Ile | Phe | Glu | Leu | Ile | Leu | Thr | Pro | Thr | Phe | Tyr | Ser |     |
|     |     |     | 340 |     |     |     |     | 345 |     |     |     |     | 350 |     |     |     |
| GCT | ATC | TTA | GCG | CTT | AGA | CTG | GAA | ATG | AAT | GTT | ATC | CAC | AGA | TCT | ACT | 1224 |
| Ala | Ile | Leu | Ala | Leu | Arg | Leu | Glu | Met | Asn | Val | Ile | His | Arg | Ser | Thr |     |
|     |     |     | 355 |     |     |     |     | 360 |     |     |     |     | 365 |     |     |     |
| ATT | ATC | AAG | CAA | ACA | TTA | GAA | GAA | GAC | GGT | GTT | GTT | CCA | TCT | ACA | GCA | 1272 |
| Ile | Ile | Lys | Gln | Thr | Leu | Glu | Glu | Asp | Gly | Val | Val | Pro | Ser | Thr | Ala |     |
|     |     |     | 370 |     |     |     |     | 375 |     |     |     |     | 380 |     |     |     |
| AGA | ATC | ATT | TCT | AAA | GCA | GAA | AAG | AAA | TCC | GTA | TCT | TCT | TTC | TTA | AAT | 1320 |
| Arg | Ile | Ile | Ser | Lys | Ala | Glu | Lys | Lys | Ser | Val | Ser | Ser | Phe | Leu | Asn |     |
| 385 |     |     |     |     | 390 |     |     |     |     | 395 |     |     |     |     | 400 |     |
| CTC | AGT | GTG | GTT | GTC | ATT | ATC | ATG | AAA | CTC | TCT | GTC | ATA | CTG | TTG | TTT | 1368 |
| Leu | Ser | Val | Val | Val | Ile | Ile | Met | Lys | Leu | Ser | Val | Ile | Leu | Leu | Phe |     |
|     |     |     |     | 405 |     |     |     |     | 410 |     |     |     |     | 415 |     |     |

```
                                                        -continued

GTT  TTC  ATC  AAC  TTT  TAT  AAC  TTT  GGT  GCA  AAT  TGG  GTC  AAT  GAT  GCC      1416
Val  Phe  Ile  Asn  Phe  Tyr  Asn  Phe  Gly  Ala  Asn  Trp  Val  Asn  Asp  Ala
               420                     425                          430

TTC  AAT  TCA  TTG  TAC  TTC  GAT  AAG  GAA  CGT  GTT  TCT  CTA  CCA  GAT  TTT      1464
Phe  Asn  Ser  Leu  Tyr  Phe  Asp  Lys  Glu  Arg  Val  Ser  Leu  Pro  Asp  Phe
          435                     440                     445

ATT  ACC  TCG  AAT  GCC  TCT  GAA  AAC  TTT  AAA  GAG  CAA  GCT  ATT  GTT  AGT      1512
Ile  Thr  Ser  Asn  Ala  Ser  Glu  Asn  Phe  Lys  Glu  Gln  Ala  Ile  Val  Ser
          450                     455                     460

GTC  ACC  CCA  TTA  TTA  TAT  TAC  AAA  CCC  ATT  AAG  TCC  TAC  CAA  CGC  ATT      1560
Val  Thr  Pro  Leu  Leu  Tyr  Tyr  Lys  Pro  Ile  Lys  Ser  Tyr  Gln  Arg  Ile
465                      470                     475                          480

GAG  GAT  ATG  GTT  CTT  CTA  TTG  CTT  CGT  AAT  GTC  AGT  GTT  GCC  ATT  CGT      1608
Glu  Asp  Met  Val  Leu  Leu  Leu  Leu  Arg  Asn  Val  Ser  Val  Ala  Ile  Arg
                    485                     490                     495

GAT  AGG  TTC  GTC  AGT  AAA  TTA  GTT  CTT  TCC  GCC  TTA  GTA  TGC  AGT  GCT      1656
Asp  Arg  Phe  Val  Ser  Lys  Leu  Val  Leu  Ser  Ala  Leu  Val  Cys  Ser  Ala
               500                     505                     510

GTC  ATC  AAT  GTG  TAT  TTA  TTG  AAT  GCT  GCT  AGA  ATT  CAT  ACC  AGT  TAT      1704
Val  Ile  Asn  Val  Tyr  Leu  Leu  Asn  Ala  Ala  Arg  Ile  His  Thr  Ser  Tyr
          515                     520                     525

ACT  GCA  GAC  CAA  TTG  GTG  AAA  ACT  GAA  GTC  ACC  AAG  AAG  TCT  TTT  ACT      1752
Thr  Ala  Asp  Gln  Leu  Val  Lys  Thr  Glu  Val  Thr  Lys  Lys  Ser  Phe  Thr
530                      535                     540

GCT  CCT  GTA  CAA  AAG  GCT  TCT  ACA  CCA  GTT  TTA  ACC  AAT  AAA  ACA  GTC      1800
Ala  Pro  Val  Gln  Lys  Ala  Ser  Thr  Pro  Val  Leu  Thr  Asn  Lys  Thr  Val
545                      550                     555                          560

ATT  TCT  GGA  TCG  AAA  GTC  AAA  AGT  TTA  TCA  TCT  GCG  CAA  TCG  AGC  TCA      1848
Ile  Ser  Gly  Ser  Lys  Val  Lys  Ser  Leu  Ser  Ser  Ala  Gln  Ser  Ser  Ser
                    565                     570                     575

TCA  GGA  CCT  TCA  TCA  TCT  AGT  GAG  GAA  GAT  GAT  TCC  CGC  GAT  ATT  GAA      1896
Ser  Gly  Pro  Ser  Ser  Ser  Ser  Glu  Glu  Asp  Asp  Ser  Arg  Asp  Ile  Glu
               580                     585                     590

AGC  TTG  GAT  AAG  AAA  ATA  CGT  CCT  TTA  GAA  GAA  TTA  GAA  GCA  TTA  TTA      1944
Ser  Leu  Asp  Lys  Lys  Ile  Arg  Pro  Leu  Glu  Glu  Leu  Glu  Ala  Leu  Leu
          595                     600                     605

AGT  AGT  GGA  AAT  ACA  AAA  CAA  TTG  AAG  AAC  AAA  GAG  GTC  GCT  GCC  TTG      1992
Ser  Ser  Gly  Asn  Thr  Lys  Gln  Leu  Lys  Asn  Lys  Glu  Val  Ala  Ala  Leu
          610                     615                     620

GTT  ATT  CAC  GGT  AAG  TTA  CCT  TTG  TAC  GCT  TTG  GAG  AAA  AAA  TTA  GGT      2040
Val  Ile  His  Gly  Lys  Leu  Pro  Leu  Tyr  Ala  Leu  Glu  Lys  Lys  Leu  Gly
625                      630                     635                          640

GAT  ACT  ACG  AGA  GCG  GTT  GCG  GTA  CGT  AGG  AAG  GCT  CTT  TCA  ATT  TTG      2088
Asp  Thr  Thr  Arg  Ala  Val  Ala  Val  Arg  Arg  Lys  Ala  Leu  Ser  Ile  Leu
                    645                     650                     655

GCA  GAA  GCT  CCT  GTA  TTA  GCA  TCT  GAT  CGT  TTA  CCA  TAT  AAA  AAT  TAT      2136
Ala  Glu  Ala  Pro  Val  Leu  Ala  Ser  Asp  Arg  Leu  Pro  Tyr  Lys  Asn  Tyr
               660                     665                     670

GAC  TAC  GAC  CGC  GTA  TTT  GGC  GCT  TGT  TGT  GAA  AAT  GTT  ATA  GGT  TAC      2184
Asp  Tyr  Asp  Arg  Val  Phe  Gly  Ala  Cys  Cys  Glu  Asn  Val  Ile  Gly  Tyr
          675                     680                     685

ATG  CCT  TTG  CCC  GTT  GGT  GTT  ATA  GGC  CCC  TTG  GTT  ATC  GAT  GGT  ACA      2232
Met  Pro  Leu  Pro  Val  Gly  Val  Ile  Gly  Pro  Leu  Val  Ile  Asp  Gly  Thr
          690                     695                     700

TCT  TAT  CAT  ATA  CCA  ATG  GCA  ACT  ACA  GAG  GGT  TGT  TTG  GTA  GCT  TCT      2280
Ser  Tyr  His  Ile  Pro  Met  Ala  Thr  Thr  Glu  Gly  Cys  Leu  Val  Ala  Ser
705                      710                     715                          720

GCC  ATG  CGT  GGC  TGT  AAG  GCA  ATC  AAT  GCT  GGC  GGT  GGT  GCA  ACA  ACT      2328
Ala  Met  Arg  Gly  Cys  Lys  Ala  Ile  Asn  Ala  Gly  Gly  Gly  Ala  Thr  Thr
                    725                     730                     735

GTT  TTA  ACT  AAG  GAT  GGT  ATG  ACA  AGA  GGC  CCA  GTA  GTC  CGT  TTC  CCA      2376
```

|  |  |  |  |  |  |  |  |  |  |  |  |  |  |  |  |  |
|--|--|--|--|--|--|--|--|--|--|--|--|--|--|--|--|--|
| Val | Leu | Thr | Lys<br>740 | Asp | Gly | Met | Thr | Arg<br>745 | Gly | Pro | Val | Val<br>750 | Arg | Phe | Pro | |
| ACT | TTG | AAA | AGA | TCT | GGT | GCC | TGT | AAG | ATA | TGG | TTA | GAC | TCA | GAA | GAG | 2424 |
| Thr | Leu | Lys<br>755 | Arg | Ser | Gly | Ala | Cys<br>760 | Lys | Ile | Trp | Leu | Asp<br>765 | Ser | Glu | Glu | |
| GGA | CAA | AAC | GCA | ATT | AAA | AAA | GCT | TTT | AAC | TCT | ACA | TCA | AGA | TTT | GCA | 2472 |
| Gly | Gln<br>770 | Asn | Ala | Ile | Lys | Lys<br>775 | Ala | Phe | Asn | Ser | Thr<br>780 | Ser | Arg | Phe | Ala | |
| CGT | CTG | CAA. | CAT | ATT | CAA | ACT | TGT | CTA | GCA | GGA | GAT | TTA | CTC | TTC | ATG | 2520 |
| Arg<br>785 | Leu | Gln | His | Ile | Gln<br>790 | Thr | Cys | Leu | Ala | Gly<br>795 | Asp | Leu | Leu | Phe | Met<br>800 | |
| AGA | TTT | AGA | ACA | ACT | ACT | GGT | GAC | GCA | ATG | GGT | ATG | AAT | ATG | ATT | TCT | 2568 |
| Arg | Phe | Arg | Thr<br>805 | Thr | Thr | Gly | Asp | Ala | Met<br>810 | Gly | Met | Asn | Met | Ile<br>815 | Ser | |
| AAA | GGT | GTC | GAA | TAC | TCA | TTA | AAG | CAA | ATG | GTA | GAA | GAG | TAT | GGC | TGG | 2616 |
| Lys | Gly | Val<br>820 | Glu | Tyr | Ser | Leu | Lys<br>825 | Gln | Met | Val | Glu | Glu<br>830 | Tyr | Gly | Trp | |
| GAA | GAT | ATG | GAG | GTT | GTC | TCC | GTT | TCT | GGT | AAC | TAC | TGT | ACC | GAC | AAA | 2664 |
| Glu | Asp | Met<br>835 | Glu | Val | Val | Ser | Val<br>840 | Ser | Gly | Asn | Tyr | Cys<br>845 | Thr | Asp | Lys | |
| AAA | CCA | GCT | GCC | ATC | AAC | TGG | ATC | GAA | GGT | CGT | GGT | AAG | AGT | GTC | GTC | 2712 |
| Lys | Pro<br>850 | Ala | Ala | Ile | Asn | Trp<br>855 | Ile | Glu | Gly | Arg | Gly<br>860 | Lys | Ser | Val | Val | |
| GCA | GAA | GCT | ACT | ATT | CCT | GGT | GAT | GTT | GTC | AGA | AAA | GTG | TTA | AAA | AGT | 2760 |
| Ala<br>865 | Glu | Ala | Thr | Ile | Pro<br>870 | Gly | Asp | Val | Val | Arg<br>875 | Lys | Val | Leu | Lys | Ser<br>880 | |
| GAT | GTT | TCC | GCA | TTG | GTT | GAG | TTG | AAC | ATT | GCT | AAG | AAT | TTG | GTT | GGA | 2808 |
| Asp | Val | Ser | Ala | Leu<br>885 | Val | Glu | Leu | Asn | Ile<br>890 | Ala | Lys | Asn | Leu | Val<br>895 | Gly | |
| TCT | GCA | ATG | GCT | GGG | TCT | GTT | GGT | GGA | TTT | AAC | GCA | CAT | GCA | GCT | AAT | 2856 |
| Ser | Ala | Met | Ala<br>900 | Gly | Ser | Val | Gly | Gly<br>905 | Phe | Asn | Ala | His | Ala<br>910 | Ala | Asn | |
| TTA | GTG | ACA | GCT | GTT | TTC | TTG | GCA | TTA | GGA | CAA | GAT | CCT | GCA | CAA | AAT | 2904 |
| Leu | Val | Thr | Ala<br>915 | Val | Phe | Leu | Ala | Leu<br>920 | Gly | Gln | Asp | Pro | Ala<br>925 | Gln | Asn | |
| GTT | GAA | AGT | TCC | AAC | TGT | ATA | ACA | TTG | ATG | AAA | GAA | GTG | GAC | GGT | GAT | 2952 |
| Val | Glu<br>930 | Ser | Ser | Asn | Cys | Ile<br>935 | Thr | Leu | Met | Lys | Glu<br>940 | Val | Asp | Gly | Asp | |
| TTG | AGA | ATT | TCC | GTA | TCC | ATG | CCA | TCC | ATC | GAA | GTA | GGT | ACC | ATC | GGT | 3000 |
| Leu<br>945 | Arg | Ile | Ser | Val | Ser<br>950 | Met | Pro | Ser | Ile | Glu<br>955 | Val | Gly | Thr | Ile | Gly<br>960 | |
| GGT | GGT | ACT | GTT | CTA | GAA | CCA | CAA | GGT | GCC | ATG | TTG | GAC | TTA | TTA | GGT | 3048 |
| Gly | Gly | Thr | Val | Leu<br>965 | Glu | Pro | Gln | Gly | Ala<br>970 | Met | Leu | Asp | Leu | Leu<br>975 | Gly | |
| GTA | AGA | GGC | CCG | CAT | GCT | ACC | GCT | CCT | GGT | ACC | AAC | GCA | CGT | CAA | TTA | 3096 |
| Val | Arg | Gly | Pro<br>980 | His | Ala | Thr | Ala | Pro<br>985 | Gly | Thr | Asn | Ala | Arg<br>990 | Gln | Leu | |
| GCA | AGA | ATA | GTT | GCC | TGT | GCC | GTC | TTG | GCA | GGT | GAA | TTA | TCC | TTA | TGT | 3144 |
| Ala | Arg | Ile<br>995 | Val | Ala | Cys | Ala | Val<br>1000 | Leu | Ala | Gly | Glu | Leu<br>1005 | Ser | Leu | Cys | |
| GCT | GCC | CTA | GCA | GCC | GGC | CAT | TTG | GTT | CAA | AGT | CAT | ATG | ACC | CAC | AAC | 3192 |
| Ala | Ala | Leu<br>1010 | Ala | Ala | Gly | His | Leu<br>1015 | Val | Gln | Ser | His | Met<br>1020 | Thr | His | Asn | |
| AGG | AAA | CCT | GCT | GAA | CCA | ACA | AAA | CCT | AAC | AAT | TTG | GAC | GCC | ACT | GAT | 3240 |
| Arg | Lys<br>1025 | Pro | Ala | Glu | Pro | Thr<br>1030 | Lys | Pro | Asn | Asn | Leu<br>1035 | Asp | Ala | Thr | Asp<br>1040 | |
| ATA | AAT | CGT | TTG | AAA | GAT | GGG | TCC | GTC | ACC | TGC | ATT | AAA | TCC |  |  | 3282 |
| Ile | Asn | Arg | Leu | Lys<br>1045 | Asp | Gly | Ser | Val | Thr<br>1050 | Cys | Ile | Lys | Ser |  |  | |

```
TAAACTTAGT CATACGTCAT TGGTATTCTC TTGAAAAAGA AGCACAACAG CACCATGTGT     3342

TACGTAAAAT ATTTACTT                                                   3360
```

( 2 ) INFORMATION FOR SEQ ID NO:4:

( i ) SEQUENCE CHARACTERISTICS:
        ( A ) LENGTH: 1054 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met<br>1 | Pro | Pro | Leu | Phe<br>5 | Lys | Gly | Leu | Lys | Gln<br>10 | Met | Ala | Lys | Pro | Ile<br>15 | Ala |
| Tyr | Val | Ser | Arg<br>20 | Phe | Ser | Ala | Lys | Arg<br>25 | Pro | Ile | His | Ile | Ile<br>30 | Leu | Phe |
| Ser | Leu | Ile<br>35 | Ile | Ser | Ala | Phe | Ala<br>40 | Tyr | Leu | Ser | Val | Ile<br>45 | Gln | Tyr | Tyr |
| Phe | Asn<br>50 | Gly | Trp | Gln | Leu | Asp<br>55 | Ser | Asn | Ser | Val | Phe<br>60 | Glu | Thr | Ala | Pro |
| Asn<br>65 | Lys | Asp | Ser | Asn | Thr<br>70 | Leu | Phe | Gln | Glu | Cys<br>75 | Ser | His | Tyr | Tyr | Arg<br>80 |
| Asp | Ser | Ser | Leu | Asp<br>85 | Gly | Trp | Val | Ser | Ile<br>90 | Thr | Ala | His | Glu | Ala<br>95 | Ser |
| Glu | Leu | Pro | Ala<br>100 | Pro | His | His | Tyr | Tyr<br>105 | Leu | Leu | Asn | Leu | Asn<br>110 | Phe | Asn |
| Ser | Pro | Asn<br>115 | Glu | Thr | Asp | Ser | Ile<br>120 | Pro | Glu | Leu | Ala | Asn<br>125 | Thr | Val | Phe |
| Glu | Lys<br>130 | Asp | Asn | Thr | Lys | Tyr<br>135 | Ile | Leu | Gln | Glu | Asp<br>140 | Leu | Ser | Val | Ser |
| Lys<br>145 | Glu | Ile | Ser | Ser | Thr<br>150 | Asp | Gly | Thr | Lys | Trp<br>155 | Arg | Leu | Arg | Ser | Asp<br>160 |
| Arg | Lys | Ser | Leu | Phe<br>165 | Asp | Val | Lys | Thr | Leu<br>170 | Ala | Tyr | Ser | Leu | Tyr<br>175 | Asp |
| Val | Phe | Ser | Glu<br>180 | Asn | Val | Thr | Gln | Ala<br>185 | Asp | Pro | Phe | Asp | Val<br>190 | Leu | Ile |
| Met | Val | Thr<br>195 | Ala | Tyr | Leu | Met | Met<br>200 | Phe | Tyr | Thr | Ile | Phe<br>205 | Gly | Leu | Phe |
| Asn | Asp<br>210 | Met | Arg | Lys | Thr | Gly<br>215 | Ser | Asn | Phe | Trp | Leu<br>220 | Ser | Ala | Ser | Thr |
| Val<br>225 | Val | Asn | Ser | Ala | Ser<br>230 | Ser | Leu | Phe | Leu | Ala<br>235 | Leu | Tyr | Val | Thr | Gln<br>240 |
| Cys | Ile | Leu | Gly | Lys<br>245 | Glu | Val | Ser | Ala | Leu<br>250 | Thr | Leu | Phe | Glu | Gly<br>255 | Leu |
| Pro | Phe | Ile | Val<br>260 | Val | Val | Val | Gly<br>265 | Phe | Lys | His | Lys | Ile<br>270 | Lys | Ile | Ala |
| Gln | Tyr | Ala<br>275 | Leu | Glu | Lys | Phe | Glu<br>280 | Arg | Val | Gly | Leu | Ser<br>285 | Lys | Arg | Ile |
| Thr | Thr<br>290 | Asp | Glu | Ile | Val | Phe<br>295 | Glu | Ser | Val | Ser | Glu<br>300 | Glu | Gly | Gly | Arg |
| Leu<br>305 | Ile | Gln | Asp | His | Leu<br>310 | Leu | Cys | Ile | Phe | Ala<br>315 | Phe | Ile | Gly | Cys<br>320 | Ser |
| Met | Tyr | Ala | His | Gln<br>325 | Leu | Lys | Thr | Leu | Thr<br>330 | Asn | Phe | Cys | Ile | Leu<br>335 | Ser |
| Ala | Phe | Ile | Leu<br>340 | Ile | Phe | Glu | Leu | Ile<br>345 | Leu | Thr | Pro | Thr | Phe<br>350 | Tyr | Ser |
| Ala | Ile | Leu<br>355 | Ala | Leu | Arg | Leu | Glu<br>360 | Met | Asn | Val | Ile | His<br>365 | Arg | Ser | Thr |

| | | | | | | | | | | | | | | |
|---|---|---|---|---|---|---|---|---|---|---|---|---|---|---|
| Ile | Ile | Lys | Gln | Thr | Leu | Glu | Glu | Asp | Gly | Val | Val | Pro | Ser | Thr | Ala |
| | 370 | | | | 375 | | | | | 380 | | | | | |
| Arg | Ile | Ile | Ser | Lys | Ala | Glu | Lys | Lys | Ser | Val | Ser | Ser | Phe | Leu | Asn |
| 385 | | | | | 390 | | | | | 395 | | | | | 400 |
| Leu | Ser | Val | Val | Val | Ile | Ile | Met | Lys | Leu | Ser | Val | Ile | Leu | Leu | Phe |
| | | | | 405 | | | | | 410 | | | | | 415 | |
| Val | Phe | Ile | Asn | Phe | Tyr | Asn | Phe | Gly | Ala | Asn | Trp | Val | Asn | Asp | Ala |
| | | | 420 | | | | | 425 | | | | | 430 | | |
| Phe | Asn | Ser | Leu | Tyr | Phe | Asp | Lys | Glu | Arg | Val | Ser | Leu | Pro | Asp | Phe |
| | | 435 | | | | | 440 | | | | | 445 | | | |
| Ile | Thr | Ser | Asn | Ala | Ser | Glu | Asn | Phe | Lys | Glu | Gln | Ala | Ile | Val | Ser |
| | 450 | | | | | 455 | | | | | 460 | | | | |
| Val | Thr | Pro | Leu | Leu | Tyr | Tyr | Lys | Pro | Ile | Lys | Ser | Tyr | Gln | Arg | Ile |
| 465 | | | | | 470 | | | | | 475 | | | | | 480 |
| Glu | Asp | Met | Val | Leu | Leu | Leu | Leu | Arg | Asn | Val | Ser | Val | Ala | Ile | Arg |
| | | | | 485 | | | | | 490 | | | | | 495 | |
| Asp | Arg | Phe | Val | Ser | Lys | Leu | Val | Leu | Ser | Ala | Leu | Val | Cys | Ser | Ala |
| | | | 500 | | | | | 505 | | | | | 510 | | |
| Val | Ile | Asn | Val | Tyr | Leu | Leu | Asn | Ala | Ala | Arg | Ile | His | Thr | Ser | Tyr |
| | | 515 | | | | | 520 | | | | | 525 | | | |
| Thr | Ala | Asp | Gln | Leu | Val | Lys | Thr | Glu | Val | Thr | Lys | Lys | Ser | Phe | Thr |
| | 530 | | | | | 535 | | | | | 540 | | | | |
| Ala | Pro | Val | Gln | Lys | Ala | Ser | Thr | Pro | Val | Leu | Thr | Asn | Lys | Thr | Val |
| 545 | | | | | 550 | | | | | 555 | | | | | 560 |
| Ile | Ser | Gly | Ser | Lys | Val | Lys | Ser | Leu | Ser | Ser | Ala | Gln | Ser | Ser | Ser |
| | | | | 565 | | | | | 570 | | | | | 575 | |
| Ser | Gly | Pro | Ser | Ser | Ser | Ser | Glu | Glu | Asp | Ser | Arg | Asp | Ile | Glu |
| | | | 580 | | | | | 585 | | | | | 590 | | |
| Ser | Leu | Asp | Lys | Lys | Ile | Arg | Pro | Leu | Glu | Glu | Leu | Glu | Ala | Leu | Leu |
| | | | 595 | | | | 600 | | | | | 605 | | | |
| Ser | Ser | Gly | Asn | Thr | Lys | Gln | Leu | Lys | Asn | Lys | Glu | Val | Ala | Ala | Leu |
| | | 610 | | | | | 615 | | | | | 620 | | | |
| Val | Ile | His | Gly | Lys | Leu | Pro | Leu | Tyr | Ala | Leu | Glu | Lys | Lys | Leu | Gly |
| 625 | | | | | 630 | | | | | 635 | | | | | 640 |
| Asp | Thr | Thr | Arg | Ala | Val | Ala | Val | Arg | Arg | Lys | Ala | Leu | Ser | Ile | Leu |
| | | | | 645 | | | | | 650 | | | | | 655 | |
| Ala | Glu | Ala | Pro | Val | Leu | Ala | Ser | Asp | Arg | Leu | Pro | Tyr | Lys | Asn | Tyr |
| | | | 660 | | | | | 665 | | | | | 670 | | |
| Asp | Tyr | Asp | Arg | Val | Phe | Gly | Ala | Cys | Cys | Glu | Asn | Val | Ile | Gly | Tyr |
| | | | 675 | | | | | 680 | | | | | 685 | | |
| Met | Pro | Leu | Pro | Val | Gly | Val | Ile | Gly | Pro | Leu | Val | Ile | Asp | Gly | Thr |
| | | | 690 | | | | 695 | | | | | 700 | | | |
| Ser | Tyr | His | Ile | Pro | Met | Ala | Thr | Thr | Glu | Gly | Cys | Leu | Val | Ala | Ser |
| 705 | | | | | 710 | | | | | 715 | | | | | 720 |
| Ala | Met | Arg | Gly | Cys | Lys | Ala | Ile | Asn | Ala | Gly | Gly | Gly | Ala | Thr | Thr |
| | | | | 725 | | | | | 730 | | | | | 735 | |
| Val | Leu | Thr | Lys | Asp | Gly | Met | Thr | Arg | Gly | Pro | Val | Val | Arg | Phe | Pro |
| | | | | 740 | | | | | 745 | | | | | 750 | |
| Thr | Leu | Lys | Arg | Ser | Gly | Ala | Cys | Lys | Ile | Trp | Leu | Asp | Ser | Glu | Glu |
| | | | 755 | | | | | 760 | | | | | 765 | | |
| Gly | Gln | Asn | Ala | Ile | Lys | Lys | Ala | Phe | Asn | Ser | Thr | Ser | Arg | Phe | Ala |
| | | | 770 | | | | 775 | | | | | 780 | | | |
| Arg | Leu | Gln | His | Ile | Gln | Thr | Cys | Leu | Ala | Gly | Asp | Leu | Leu | Phe | Met |
| 785 | | | | | 790 | | | | | 795 | | | | | 800 |
| Arg | Phe | Arg | Thr | Thr | Thr | Gly | Asp | Ala | Met | Gly | Met | Asn | Met | Ile | Ser |

|     |     |     |     | 805 |     |     |     |     | 810 |     |     |     |     | 815 |     |
|---|---|---|---|---|---|---|---|---|---|---|---|---|---|---|---|

Lys Gly Val Glu Tyr Ser Leu Lys Gln Met Val Glu Glu Tyr Gly Trp
            820                     825                     830

Glu Asp Met Glu Val Val Ser Val Ser Gly Asn Tyr Cys Thr Asp Lys
        835                     840                 845

Lys Pro Ala Ala Ile Asn Trp Ile Glu Gly Arg Gly Lys Ser Val Val
    850                     855                 860

Ala Glu Ala Thr Ile Pro Gly Asp Val Val Arg Lys Val Leu Lys Ser
865                 870                     875                 880

Asp Val Ser Ala Leu Val Glu Leu Asn Ile Ala Lys Asn Leu Val Gly
            885                     890                 895

Ser Ala Met Ala Gly Ser Val Gly Gly Phe Asn Ala His Ala Ala Asn
            900                     905                 910

Leu Val Thr Ala Val Phe Leu Ala Leu Gly Gln Asp Pro Ala Gln Asn
            915                     920                 925

Val Glu Ser Ser Asn Cys Ile Thr Leu Met Lys Glu Val Asp Gly Asp
    930                     935                 940

Leu Arg Ile Ser Val Ser Met Pro Ser Ile Glu Val Gly Thr Ile Gly
945                 950                     955                 960

Gly Gly Thr Val Leu Glu Pro Gln Gly Ala Met Leu Asp Leu Leu Gly
                965                     970                 975

Val Arg Gly Pro His Ala Thr Ala Pro Gly Thr Asn Ala Arg Gln Leu
            980                     985                 990

Ala Arg Ile Val Ala Cys Ala Val Leu Ala Gly Glu Leu Ser Leu Cys
            995                     1000                1005

Ala Ala Leu Ala Ala Gly His Leu Val Gln Ser His Met Thr His Asn
        1010                    1015                1020

Arg Lys Pro Ala Glu Pro Thr Lys Pro Asn Asn Leu Asp Ala Thr Asp
1025                    1030                    1035                1040

Ile Asn Arg Leu Lys Asp Gly Ser Val Thr Cys Ile Lys Ser
                1045                    1050

(2) INFORMATION FOR SEQ ID NO:5:

(i) SEQUENCE CHARACTERISTICS:
        (A) LENGTH: 3348 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 121..3255

(xi) SEQUENCE DESCRIPTION: SEQ ID NO:5:

```
GGAATATTTT GTACGAGCAA GTTATAGTAA GACACTTCAG TGAGAAATTA ATCTGACTTA      60

CTTTTACTTA ATTGTGTTCT TTCCAAATTA GTTCAACAAG GTTCCACAT ACAACCTCAA      120
```

ATG TCA CTT CCC TTA AAA ACG ATA GTA CAT TTG GTA AAG CCC TTT GCT      168
Met Ser Leu Pro Leu Lys Thr Ile Val His Leu Val Lys Pro Phe Ala
1               5                   10                  15

TGC ACT GCT AGG TTT AGT GCG AGA TAC CCA ATC CAC GTC ATT GTT GTT      216
Cys Thr Ala Arg Phe Ser Ala Arg Tyr Pro Ile His Val Ile Val Val
            20                  25                  30

GCT GTT TTA TTG AGT GCC GCT GCT TAT CTA TCC GTG ACA CAA TCT TAC      264
Ala Val Leu Leu Ser Ala Ala Ala Tyr Leu Ser Val Thr Gln Ser Tyr
            35                  40                  45

CTT AAC GAA TGG AAG CTG GAC TCT AAT CAG TAT TCT ACA TAC TTA AGC      312
Leu Asn Glu Trp Lys Leu Asp Ser Asn Gln Tyr Ser Thr Tyr Leu Ser

|       50        |                 | 55              |                 | 60              |      |
|-----------------|-----------------|-----------------|-----------------|-----------------|------|
| ATA AAG CCG GAT GAG TTG TTT GAA AAA TGC ACA CAC TAC TAT AGG TCT | 360 |
| Ile Lys Pro Asp Glu Leu Phe Glu Lys Cys Thr His Tyr Tyr Arg Ser | |
| 65              | 70              |                 | 75              | 80              | |

```
ATA AAG CCG GAT GAG TTG TTT GAA AAA TGC ACA CAC TAC TAT AGG TCT        360
Ile Lys Pro Asp Glu Leu Phe Glu Lys Cys Thr His Tyr Tyr Arg Ser
 65              70                   75                  80

CCT GTG TCT GAT ACA TGG AAG TTA CTC AGC TCT AAA GAA GCC GCC GAT        408
Pro Val Ser Asp Thr Trp Lys Leu Leu Ser Ser Lys Glu Ala Ala Asp
                 85                  90                  95

ATT TAT ACC CCT TTT CAT TAT TAT TTG TCT ACC ATA AGT TTT CAA AGT        456
Ile Tyr Thr Pro Phe His Tyr Tyr Leu Ser Thr Ile Ser Phe Gln Ser
            100                 105                 110

AAG GAC AAT TCA ACG ACT TTG CCT TCC CTT GAT GAC GTT ATT TAC AGT        504
Lys Asp Asn Ser Thr Thr Leu Pro Ser Leu Asp Asp Val Ile Tyr Ser
            115                 120                 125

GTT GAC CAT ACC AGG TAC TTA TTA AGT GAA GAG CCA AAG ATA CCA ACT        552
Val Asp His Thr Arg Tyr Leu Leu Ser Glu Glu Pro Lys Ile Pro Thr
130                 135                 140

GAA CTA GTG TCT GAA AAC GGA ACG AAA TGG AGA TTG AGA AAC AAC AGC        600
Glu Leu Val Ser Glu Asn Gly Thr Lys Trp Arg Leu Arg Asn Asn Ser
145                 150                 155                 160

AAT TTT ATT TTG GAC CTG CAT AAT ATT TAC CGA AAT ATG GTG AAG CAA        648
Asn Phe Ile Leu Asp Leu His Asn Ile Tyr Arg Asn Met Val Lys Gln
                165                 170                 175

TTT TCT AAC AAA ACG AGC GAA TTT GAT CAG TTC GAT TTG TTT ATC ATC        696
Phe Ser Asn Lys Thr Ser Glu Phe Asp Gln Phe Asp Leu Phe Ile Ile
                180                 185                 190

CTA GCT GCT TAC CTT ACT CTT TTT TAT ACT CTC TGT TGC CTG TTT AAT        744
Leu Ala Ala Tyr Leu Thr Leu Phe Tyr Thr Leu Cys Cys Leu Phe Asn
            195                 200                 205

GAC ATG AGG AAA ATC GGA TCA AAG TTT TGG TTA AGC TTT TCT GCT CTT        792
Asp Met Arg Lys Ile Gly Ser Lys Phe Trp Leu Ser Phe Ser Ala Leu
210                 215                 220

TCA AAC TCT GCA TGC GCA TTA TAT TTA TCG CTG TAC ACA ACT CAC AGT        840
Ser Asn Ser Ala Cys Ala Leu Tyr Leu Ser Leu Tyr Thr Thr His Ser
225                 230                 235                 240

TTA TTG AAG AAA CCG GCT TCC TTA TTA AGT TTG GTC ATT GGA CTA CCA        888
Leu Leu Lys Lys Pro Ala Ser Leu Leu Ser Leu Val Ile Gly Leu Pro
                245                 250                 255

TTT ATC GTA GTA ATT ATT GGC TTT AAG CAT AAA GTT CGA CTT GCG GCA        936
Phe Ile Val Val Ile Ile Gly Phe Lys His Lys Val Arg Leu Ala Ala
            260                 265                 270

TTC TCG CTA CAA AAA TTC CAC AGA ATT AGT ATT GAC AAG AAA ATA ACG        984
Phe Ser Leu Gln Lys Phe His Arg Ile Ser Ile Asp Lys Lys Ile Thr
        275                 280                 285

GTA AGC AAC ATT ATT TAT GAG GCT ATG TTT CAA GAA GGT GCC TAC TTA       1032
Val Ser Asn Ile Ile Tyr Glu Ala Met Phe Gln Glu Gly Ala Tyr Leu
290                 295                 300

ATC CGC GAC TAC TTA TTT TAT ATT AGC TCC TTC ATT GGA TGT GCT ATT       1080
Ile Arg Asp Tyr Leu Phe Tyr Ile Ser Ser Phe Ile Gly Cys Ala Ile
305                 310                 315                 320

TAT GCT AGA CAT CTT CCC GGA TTG GTC AAT TTC TGT ATT TTG TCT ACA       1128
Tyr Ala Arg His Leu Pro Gly Leu Val Asn Phe Cys Ile Leu Ser Thr
                325                 330                 335

TTT ATG CTA GTT TTC GAC TTG CTT TTG TCT GCT ACT TTT TAT TCT GCC       1176
Phe Met Leu Val Phe Asp Leu Leu Leu Ser Ala Thr Phe Tyr Ser Ala
            340                 345                 350

ATT TTA TCA ATG AAG CTG GAA ATT AAC ATC ATT CAC AGA TCA ACC GTC       1224
Ile Leu Ser Met Lys Leu Glu Ile Asn Ile Ile His Arg Ser Thr Val
        355                 360                 365

ATC AGA CAG ACT TTG GAA GAG GAC GGA GTT GTC CCA ACT ACA GCA GAT       1272
Ile Arg Gln Thr Leu Glu Glu Asp Gly Val Val Pro Thr Thr Ala Asp
370                 375                 380
```

| | | | | | | | | | | | | | | | | |
|---|---|---|---|---|---|---|---|---|---|---|---|---|---|---|---|---|
| ATT | ATA | TAT | AAG | GAT | GAA | ACT | GCC | TCA | GAA | CCA | CAT | TTT | TTG | AGA | TCT | 1320 |
| Ile | Ile | Tyr | Lys | Asp | Glu | Thr | Ala | Ser | Glu | Pro | His | Phe | Leu | Arg | Ser | |
| 385 | | | | 390 | | | | | | 395 | | | | | 400 | |
| AAC | GTG | GCT | ATC | ATT | CTG | GGA | AAA | GCA | TCA | GTT | ATT | GGT | CTT | TTG | CTT | 1368 |
| Asn | Val | Ala | Ile | Ile | Leu | Gly | Lys | Ala | Ser | Val | Ile | Gly | Leu | Leu | Leu | |
| | | | | 405 | | | | | 410 | | | | | 415 | | |
| CTG | ATC | AAC | CTT | TAT | GTT | TTC | ACA | GAT | AAG | TTA | AAT | GCT | ACA | ATA | CTA | 1416 |
| Leu | Ile | Asn | Leu | Tyr | Val | Phe | Thr | Asp | Lys | Leu | Asn | Ala | Thr | Ile | Leu | |
| | | | 420 | | | | | 425 | | | | | 430 | | | |
| AAC | ACG | GTA | TAT | TTT | GAC | TCT | ACA | ATT | TAC | TCG | TTA | CCA | AAT | TTT | ATC | 1464 |
| Asn | Thr | Val | Tyr | Phe | Asp | Ser | Thr | Ile | Tyr | Ser | Leu | Pro | Asn | Phe | Ile | |
| | | 435 | | | | | 440 | | | | | 445 | | | | |
| AAT | TAT | AAA | GAT | ATT | GGC | AAT | CTC | AGC | AAT | CAA | GTG | ATC | ATT | TCC | GTG | 1512 |
| Asn | Tyr | Lys | Asp | Ile | Gly | Asn | Leu | Ser | Asn | Gln | Val | Ile | Ile | Ser | Val | |
| | | 450 | | | | | 455 | | | | | 460 | | | | |
| TTG | CCA | AAG | CAA | TAT | TAT | ACT | CCG | CTG | AAA | AAA | TAC | CAT | CAG | ATC | GAA | 1560 |
| Leu | Pro | Lys | Gln | Tyr | Tyr | Thr | Pro | Leu | Lys | Lys | Tyr | His | Gln | Ile | Glu | |
| 465 | | | | | 470 | | | | | 475 | | | | | 480 | |
| GAT | TCT | GTT | CTA | CTT | ATC | ATT | GAT | TCC | GTT | AGC | AAT | GCT | ATT | CGG | GAC | 1608 |
| Asp | Ser | Val | Leu | Leu | Ile | Ile | Asp | Ser | Val | Ser | Asn | Ala | Ile | Arg | Asp | |
| | | | | 485 | | | | | 490 | | | | | 495 | | |
| CAA | TTT | ATC | AGC | AAG | TTA | CTT | TTT | TTT | GCA | TTT | GCA | GTT | AGT | ATT | TCC | 1656 |
| Gln | Phe | Ile | Ser | Lys | Leu | Leu | Phe | Phe | Ala | Phe | Ala | Val | Ser | Ile | Ser | |
| | | | 500 | | | | | 505 | | | | | 510 | | | |
| ATC | AAT | GTC | TAC | TTA | CTG | AAT | GCT | GCA | AAA | ATT | CAC | ACA | GGA | TAC | ATG | 1704 |
| Ile | Asn | Val | Tyr | Leu | Leu | Asn | Ala | Ala | Lys | Ile | His | Thr | Gly | Tyr | Met | |
| | | 515 | | | | | 520 | | | | | 525 | | | | |
| AAC | TTC | CAA | CCA | CAA | TCA | AAT | AAG | ATC | GAT | GAT | CTT | GTT | GTT | CAG | CAA | 1752 |
| Asn | Phe | Gln | Pro | Gln | Ser | Asn | Lys | Ile | Asp | Asp | Leu | Val | Val | Gln | Gln | |
| | | 530 | | | | | 535 | | | | | 540 | | | | |
| AAA | TCG | GCA | ACG | ATT | GAG | TTT | TCA | GAA | ACT | CGA | AGT | ATG | CCT | GCT | TCT | 1800 |
| Lys | Ser | Ala | Thr | Ile | Glu | Phe | Ser | Glu | Thr | Arg | Ser | Met | Pro | Ala | Ser | |
| 545 | | | | | 550 | | | | | 555 | | | | | 560 | |
| TCT | GGC | CTA | GAA | ACT | CCA | GTG | ACC | GCG | AAA | GAT | ATA | ATT | ATC | TCT | GAA | 1848 |
| Ser | Gly | Leu | Glu | Thr | Pro | Val | Thr | Ala | Lys | Asp | Ile | Ile | Ile | Ser | Glu | |
| | | | | 565 | | | | | 570 | | | | | 575 | | |
| GAA | ATC | CAG | AAT | AAC | GAA | TGC | GTC | TAT | GCT | TTG | AGT | TCC | CAG | GAC | GAG | 1896 |
| Glu | Ile | Gln | Asn | Asn | Glu | Cys | Val | Tyr | Ala | Leu | Ser | Ser | Gln | Asp | Glu | |
| | | | 580 | | | | | 585 | | | | | 590 | | | |
| CCT | ATC | CGT | CCT | TTA | TCG | AAT | TTA | GTG | GAA | CTT | ATG | GAG | AAA | GAA | CAA | 1944 |
| Pro | Ile | Arg | Pro | Leu | Ser | Asn | Leu | Val | Glu | Leu | Met | Glu | Lys | Glu | Gln | |
| | | 595 | | | | | 600 | | | | | 605 | | | | |
| TTA | AAG | AAC | ATG | AAT | AAT | ACT | GAG | GTT | TCG | AAT | CTT | GTC | GTC | AAC | GGT | 1992 |
| Leu | Lys | Asn | Met | Asn | Asn | Thr | Glu | Val | Ser | Asn | Leu | Val | Val | Asn | Gly | |
| | | 610 | | | | | 615 | | | | | 620 | | | | |
| AAA | CTG | CCA | TTA | TAT | TCC | TTA | GAG | AAA | AAA | TTA | GAG | GAC | ACA | ACT | CGT | 2040 |
| Lys | Leu | Pro | Leu | Tyr | Ser | Leu | Glu | Lys | Lys | Leu | Glu | Asp | Thr | Thr | Arg | |
| 625 | | | | | 630 | | | | | 635 | | | | | 640 | |
| GCG | GTT | TTA | GTT | AGG | AGA | AAG | GCA | CTT | TCA | ACT | TTG | GCT | GAA | TCG | CCA | 2088 |
| Ala | Val | Leu | Val | Arg | Arg | Lys | Ala | Leu | Ser | Thr | Leu | Ala | Glu | Ser | Pro | |
| | | | | 645 | | | | | 650 | | | | | 655 | | |
| ATT | TTA | GTT | TCC | GAA | AAA | TTG | CCC | TTC | AGA | AAT | TAT | GAT | TAT | GAT | CGC | 2136 |
| Ile | Leu | Val | Ser | Glu | Lys | Leu | Pro | Phe | Arg | Asn | Tyr | Asp | Tyr | Asp | Arg | |
| | | | 660 | | | | | 665 | | | | | 670 | | | |
| GTT | TTT | GGA | GCT | TGC | TGT | GAA | AAT | GTC | ATC | GGC | TAT | ATG | CCA | ATA | CCA | 2184 |
| Val | Phe | Gly | Ala | Cys | Cys | Glu | Asn | Val | Ile | Gly | Tyr | Met | Pro | Ile | Pro | |
| | | 675 | | | | | 680 | | | | | 685 | | | | |
| GTT | GGT | GTA | ATT | GGT | CCA | TTA | ATT | ATT | GAT | GGA | ACA | TCT | TAT | CAC | ATA | 2232 |
| Val | Gly | Val | Ile | Gly | Pro | Leu | Ile | Ile | Asp | Gly | Thr | Ser | Tyr | His | Ile | |
| | | 690 | | | | | 695 | | | | | 700 | | | | |
| CCA | ATG | GCA | ACC | ACG | GAA | GGT | TGT | TTA | GTG | GCT | TCA | GCT | ATG | CGT | GGT | 2280 |
| Pro | Met | Ala | Thr | Thr | Glu | Gly | Cys | Leu | Val | Ala | Ser | Ala | Met | Arg | Gly | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 705 |     |     |     |     | 710 |     |     |     |     | 715 |     |     |     |     | 720 |      |
| TGC | AAA | GCC | ATC | AAT | GCT | GGT | GGT | GGT | GCA | ACA | ACT | GTT | TTA | ACC | AAA | 2328 |
| Cys | Lys | Ala | Ile | Asn | Ala | Gly | Gly | Gly | Ala | Thr | Thr | Val | Leu | Thr | Lys |      |
|     |     |     |     | 725 |     |     |     |     | 730 |     |     |     |     | 735 |     |      |
| GAT | GGT | ATG | ACT | AGA | GGC | CCA | GTC | GTT | CGT | TTC | CCT | ACT | TTA | ATA | AGA | 2376 |
| Asp | Gly | Met | Thr | Arg | Gly | Pro | Val | Val | Arg | Phe | Pro | Thr | Leu | Ile | Arg |      |
|     |     |     | 740 |     |     |     |     | 745 |     |     |     |     | 750 |     |     |      |
| TCT | GGT | GCC | TGC | AAG | ATA | TGG | TTA | GAC | TCG | GAA | GAG | GGA | CAA | AAT | TCA | 2424 |
| Ser | Gly | Ala | Cys | Lys | Ile | Trp | Leu | Asp | Ser | Glu | Glu | Gly | Gln | Asn | Ser |      |
|     |     | 755 |     |     |     |     | 760 |     |     |     |     | 765 |     |     |     |      |
| ATT | AAA | AAA | GCT | TTT | AAT | TCT | ACA | TCA | AGG | TTT | GCA | CGT | TTG | CAA | CAT | 2472 |
| Ile | Lys | Lys | Ala | Phe | Asn | Ser | Thr | Ser | Arg | Phe | Ala | Arg | Leu | Gln | His |      |
|     | 770 |     |     |     |     | 775 |     |     |     |     | 780 |     |     |     |     |      |
| ATT | CAA | ACC | TGT | CTA | GCA | GGC | GAT | TTG | CTT | TTT | ATG | AGA | TTT | CGG | ACA | 2520 |
| Ile | Gln | Thr | Cys | Leu | Ala | Gly | Asp | Leu | Leu | Phe | Met | Arg | Phe | Arg | Thr |      |
| 785 |     |     |     |     | 790 |     |     |     |     | 795 |     |     |     |     | 800 |      |
| ACT | ACC | GGT | GAC | GCA | ATG | GGT | ATG | AAC | ATG | ATA | TCG | AAA | GGT | GTC | GAA | 2568 |
| Thr | Thr | Gly | Asp | Ala | Met | Gly | Met | Asn | Met | Ile | Ser | Lys | Gly | Val | Glu |      |
|     |     |     |     | 805 |     |     |     |     | 810 |     |     |     |     | 815 |     |      |
| TAC | TCT | TTG | AAA | CAA | ATG | GTA | GAA | GAA | TAT | GGT | TGG | GAA | GAT | ATG | GAA | 2616 |
| Tyr | Ser | Leu | Lys | Gln | Met | Val | Glu | Glu | Tyr | Gly | Trp | Glu | Asp | Met | Glu |      |
|     |     |     | 820 |     |     |     |     | 825 |     |     |     |     | 830 |     |     |      |
| GTT | GTC | TCC | GTA | TCT | GGT | AAC | TAT | TGT | ACT | GAT | AAG | AAA | CCT | GCC | GCA | 2664 |
| Val | Val | Ser | Val | Ser | Gly | Asn | Tyr | Cys | Thr | Asp | Lys | Lys | Pro | Ala | Ala |      |
|     |     | 835 |     |     |     |     | 840 |     |     |     |     | 845 |     |     |     |      |
| ATC | AAT | TGG | ATT | GAA | GGT | CGT | GGT | AAA | AGT | GTC | GTA | GCT | GAA | GCT | ACT | 2712 |
| Ile | Asn | Trp | Ile | Glu | Gly | Arg | Gly | Lys | Ser | Val | Val | Ala | Glu | Ala | Thr |      |
|     | 850 |     |     |     |     | 855 |     |     |     |     | 860 |     |     |     |     |      |
| ATT | CCT | GGT | GAT | GTC | GTA | AAA | AGT | GTT | TTA | AAG | AGC | GAT | GTT | TCC | GCT | 2760 |
| Ile | Pro | Gly | Asp | Val | Val | Lys | Ser | Val | Leu | Lys | Ser | Asp | Val | Ser | Ala |      |
| 865 |     |     |     |     | 870 |     |     |     |     | 875 |     |     |     |     | 880 |      |
| TTA | GTT | GAA | TTA | AAT | ATA | TCC | AAG | AAC | TTG | GTT | GGA | TCC | GCA | ATG | GCT | 2808 |
| Leu | Val | Glu | Leu | Asn | Ile | Ser | Lys | Asn | Leu | Val | Gly | Ser | Ala | Met | Ala |      |
|     |     |     |     | 885 |     |     |     |     | 890 |     |     |     |     | 895 |     |      |
| GGA | TCT | GTT | GGT | GGT | TTC | AAC | GCG | CAC | GCA | GCT | AAT | TTG | GTC | ACT | GCA | 2856 |
| Gly | Ser | Val | Gly | Gly | Phe | Asn | Ala | His | Ala | Ala | Asn | Leu | Val | Thr | Ala |      |
|     |     |     | 900 |     |     |     |     | 905 |     |     |     |     | 910 |     |     |      |
| CTT | TTC | TTG | GCA | TTA | GGC | CAA | GAT | CCT | GCG | CAG | AAC | GTC | GAA | AGT | TCC | 2904 |
| Leu | Phe | Leu | Ala | Leu | Gly | Gln | Asp | Pro | Ala | Gln | Asn | Val | Glu | Ser | Ser |      |
|     |     | 915 |     |     |     |     | 920 |     |     |     |     | 925 |     |     |     |      |
| AAC | TGT | ATA | ACT | TTG | ATG | AAG | GAA | GTT | GAT | GGT | GAT | TTA | AGG | ATC | TCT | 2952 |
| Asn | Cys | Ile | Thr | Leu | Met | Lys | Glu | Val | Asp | Gly | Asp | Leu | Arg | Ile | Ser |      |
|     | 930 |     |     |     |     | 935 |     |     |     |     | 940 |     |     |     |     |      |
| GTT | TCC | ATG | CCA | TCT | ATT | GAA | GTT | GGT | ACG | ATT | GGC | GGG | GGT | ACT | GTT | 3000 |
| Val | Ser | Met | Pro | Ser | Ile | Glu | Val | Gly | Thr | Ile | Gly | Gly | Gly | Thr | Val |      |
| 945 |     |     |     |     | 950 |     |     |     |     | 955 |     |     |     |     | 960 |      |
| CTG | GAG | CCT | CAG | GGC | GCC | ATG | CTT | GAT | CTT | CTC | GGC | GTT | CGT | GGT | CCT | 3048 |
| Leu | Glu | Pro | Gln | Gly | Ala | Met | Leu | Asp | Leu | Leu | Gly | Val | Arg | Gly | Pro |      |
|     |     |     |     | 965 |     |     |     |     | 970 |     |     |     |     | 975 |     |      |
| CAC | CCC | ACT | GAA | CCT | GGA | GCA | AAT | GCT | AGG | CAA | TTA | GCT | AGA | ATA | ATC | 3096 |
| His | Pro | Thr | Glu | Pro | Gly | Ala | Asn | Ala | Arg | Gln | Leu | Ala | Arg | Ile | Ile |      |
|     |     |     | 980 |     |     |     |     | 985 |     |     |     |     | 990 |     |     |      |
| GCG | TGT | GCT | GTC | TTG | GCT | GGT | GAA | CTG | TCT | CTG | TGC | TCC | GCA | CTT | GCT | 3144 |
| Ala | Cys | Ala | Val | Leu | Ala | Gly | Glu | Leu | Ser | Leu | Cys | Ser | Ala | Leu | Ala |      |
|     |     | 995 |     |     |     |     | 1000|     |     |     |     | 1005|     |     |     |      |
| GCC | GGT | CAC | CTG | GTA | CAA | AGC | CAT | ATG | ACT | CAC | AAC | CGT | AAA | ACA | AAC | 3192 |
| Ala | Gly | His | Leu | Val | Gln | Ser | His | Met | Thr | His | Asn | Arg | Lys | Thr | Asn |      |
|     |     |     | 1010|     |     |     |     | 1015|     |     |     |     | 1020|     |     |      |
| AAA | GCC | AAT | GAA | CTG | CCA | CAA | CCA | AGT | AAC | AAA | GGG | CCC | CCC | TGT | AAA | 3240 |
| Lys | Ala | Asn | Glu | Leu | Pro | Gln | Pro | Ser | Asn | Lys | Gly | Pro | Pro | Cys | Lys |      |
| 1025|     |     |     |     | 1030|     |     |     |     | 1035|     |     |     |     | 1040|      |

```
ACC TCA GCA TTA TTA TAACTCTTGT AGTTTACATG GTGATACTTT ATATCTTTGT        3295
Thr Ser Ala Leu Leu
                1045

ATTGTCTAGC TATTCTAAAT CATCTGCATG TAATAAGAAG TTGATCAAAA TGA              3348
```

( 2 ) INFORMATION FOR SEQ ID NO:6:

( i ) SEQUENCE CHARACTERISTICS:
        ( A ) LENGTH: 1045 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Leu Pro Leu Lys Thr Ile Val His Leu Val Lys Pro Phe Ala
 1           5                  10                  15

Cys Thr Ala Arg Phe Ser Ala Arg Tyr Pro Ile His Val Ile Val Val
            20                  25                  30

Ala Val Leu Leu Ser Ala Ala Ala Tyr Leu Ser Val Thr Gln Ser Tyr
             35                  40                  45

Leu Asn Glu Trp Lys Leu Asp Ser Asn Gln Tyr Ser Thr Tyr Leu Ser
     50                  55                  60

Ile Lys Pro Asp Glu Leu Phe Glu Lys Cys Thr His Tyr Tyr Arg Ser
 65                  70                  75                  80

Pro Val Ser Asp Thr Trp Lys Leu Leu Ser Ser Lys Glu Ala Ala Asp
                85                  90                  95

Ile Tyr Thr Pro Phe His Tyr Tyr Leu Ser Thr Ile Ser Phe Gln Ser
                100                 105                 110

Lys Asp Asn Ser Thr Thr Leu Pro Ser Leu Asp Asp Val Ile Tyr Ser
            115                 120                 125

Val Asp His Thr Arg Tyr Leu Leu Ser Glu Glu Pro Lys Ile Pro Thr
130                 135                 140

Glu Leu Val Ser Glu Asn Gly Thr Lys Trp Arg Leu Arg Asn Asn Ser
145                 150                 155                 160

Asn Phe Ile Leu Asp Leu His Asn Ile Tyr Arg Asn Met Val Lys Gln
                165                 170                 175

Phe Ser Asn Lys Thr Ser Glu Phe Asp Gln Phe Asp Leu Phe Ile Ile
            180                 185                 190

Leu Ala Ala Tyr Leu Thr Leu Phe Tyr Thr Leu Cys Cys Leu Phe Asn
            195                 200                 205

Asp Met Arg Lys Ile Gly Ser Lys Phe Trp Leu Ser Phe Ser Ala Leu
    210                 215                 220

Ser Asn Ser Ala Cys Ala Leu Tyr Leu Ser Leu Tyr Thr Thr His Ser
225                 230                 235                 240

Leu Leu Lys Lys Pro Ala Ser Leu Leu Ser Leu Val Ile Gly Leu Pro
                245                 250                 255

Phe Ile Val Val Ile Ile Gly Phe Lys His Lys Val Arg Leu Ala Ala
            260                 265                 270

Phe Ser Leu Gln Lys Phe His Arg Ile Ser Ile Asp Lys Lys Ile Thr
            275                 280                 285

Val Ser Asn Ile Ile Tyr Glu Ala Met Phe Gln Glu Gly Ala Tyr Leu
    290                 295                 300

Ile Arg Asp Tyr Leu Phe Tyr Ile Ser Ser Phe Ile Gly Cys Ala Ile
305                 310                 315                 320

Tyr Ala Arg His Leu Pro Gly Leu Val Asn Phe Cys Ile Leu Ser Thr
                325                 330                 335

Phe Met Leu Val Phe Asp Leu Leu Leu Ser Ala Thr Phe Tyr Ser Ala
```

|   |   |   |   |   | 340 |   |   |   |   | 345 |   |   |   |   | 350 |   |   |
|---|---|---|---|---|---|---|---|---|---|---|---|---|---|---|---|---|---|

Ile Leu Ser Met Lys Leu Glu Ile Asn Ile Ile His Arg Ser Thr Val
        355                   360                   365

Ile Arg Gln Thr Leu Glu Glu Asp Gly Val Val Pro Thr Thr Ala Asp
   370                   375                   380

Ile Ile Tyr Lys Asp Glu Thr Ala Ser Glu Pro His Phe Leu Arg Ser
385                   390                   395               400

Asn Val Ala Ile Ile Leu Gly Lys Ala Ser Val Ile Gly Leu Leu Leu
             405              410               415

Leu Ile Asn Leu Tyr Val Phe Thr Asp Lys Leu Asn Ala Thr Ile Leu
        420                  425             430

Asn Thr Val Tyr Phe Asp Ser Thr Ile Tyr Ser Leu Pro Asn Phe Ile
       435              440             445

Asn Tyr Lys Asp Ile Gly Asn Leu Ser Asn Gln Val Ile Ile Ser Val
   450               455             460

Leu Pro Lys Gln Tyr Tyr Thr Pro Leu Lys Lys Tyr His Gln Ile Glu
465                  470              475             480

Asp Ser Val Leu Leu Ile Ile Asp Ser Val Ser Asn Ala Ile Arg Asp
        485                  490             495

Gln Phe Ile Ser Lys Leu Leu Phe Phe Ala Phe Ala Val Ser Ile Ser
       500              505            510

Ile Asn Val Tyr Leu Leu Asn Ala Ala Lys Ile His Thr Gly Tyr Met
     515              520             525

Asn Phe Gln Pro Gln Ser Asn Lys Ile Asp Asp Leu Val Val Gln Gln
   530               535            540

Lys Ser Ala Thr Ile Glu Phe Ser Glu Thr Arg Ser Met Pro Ala Ser
545                 550              555             560

Ser Gly Leu Glu Thr Pro Val Thr Ala Lys Asp Ile Ile Ile Ser Glu
             565              570               575

Glu Ile Gln Asn Asn Glu Cys Val Tyr Ala Leu Ser Ser Gln Asp Glu
        580                 585             590

Pro Ile Arg Pro Leu Ser Asn Leu Val Glu Leu Met Glu Lys Glu Gln
     595              600              605

Leu Lys Asn Met Asn Asn Thr Glu Val Ser Asn Leu Val Val Asn Gly
   610               615            620

Lys Leu Pro Leu Tyr Ser Leu Glu Lys Lys Leu Glu Asp Thr Thr Arg
625                  630             635             640

Ala Val Leu Val Arg Arg Lys Ala Leu Ser Thr Leu Ala Glu Ser Pro
             645              650             655

Ile Leu Val Ser Glu Lys Leu Pro Phe Arg Asn Tyr Asp Tyr Asp Arg
        660               665             670

Val Phe Gly Ala Cys Cys Glu Asn Val Ile Gly Tyr Met Pro Ile Pro
     675              680             685

Val Gly Val Ile Gly Pro Leu Ile Ile Asp Gly Thr Ser Tyr His Ile
   690               695            700

Pro Met Ala Thr Thr Glu Gly Cys Leu Val Ala Ser Ala Met Arg Gly
705                  710             715            720

Cys Lys Ala Ile Asn Ala Gly Gly Gly Ala Thr Thr Val Leu Thr Lys
             725             730             735

Asp Gly Met Thr Arg Gly Pro Val Val Arg Phe Pro Thr Leu Ile Arg
        740             745               750

Ser Gly Ala Cys Lys Ile Trp Leu Asp Ser Glu Glu Gly Gln Asn Ser
       755              760            765

Ile Lys Lys Ala Phe Asn Ser Thr Ser Arg Phe Ala Arg Leu Gln His
   770               775            780

| | | | | | | | | | | | | | | |
|---|---|---|---|---|---|---|---|---|---|---|---|---|---|---|
| Ile 785 | Gln | Thr | Cys | Leu | Ala 790 | Gly | Asp | Leu | Leu | Phe 795 | Met | Arg | Phe | Arg Thr 800 |
| Thr | Thr | Gly | Asp | Ala 805 | Met | Gly | Met | Asn | Met 810 | Ile | Ser | Lys | Gly | Val Glu 815 |
| Tyr | Ser | Leu | Lys 820 | Gln | Met | Val | Glu | Glu 825 | Tyr | Gly | Trp | Glu | Asp 830 | Met Glu |
| Val | Val | Ser 835 | Val | Ser | Gly | Asn | Tyr 840 | Cys | Thr | Asp | Lys | Lys 845 | Pro | Ala Ala |
| Ile | Asn 850 | Trp | Ile | Glu | Gly | Arg 855 | Gly | Lys | Ser | Val | Val 860 | Ala | Glu | Ala Thr |
| Ile 865 | Pro | Gly | Asp | Val | Val 870 | Lys | Ser | Val | Leu | Lys 875 | Ser | Asp | Val | Ser Ala 880 |
| Leu | Val | Glu | Leu | Asn 885 | Ile | Ser | Lys | Asn | Leu 890 | Val | Gly | Ser | Ala | Met Ala 895 |
| Gly | Ser | Val | Gly 900 | Gly | Phe | Asn | Ala | His 905 | Ala | Ala | Asn | Leu | Val 910 | Thr Ala |
| Leu | Phe | Leu 915 | Ala | Leu | Gly | Gln | Asp 920 | Pro | Ala | Gln | Asn | Val 925 | Glu | Ser Ser |
| Asn | Cys 930 | Ile | Thr | Leu | Met | Lys 935 | Glu | Val | Asp | Gly | Asp 940 | Leu | Arg | Ile Ser |
| Val 945 | Ser | Met | Pro | Ser | Ile 950 | Glu | Val | Gly | Thr | Ile 955 | Gly | Gly | Gly | Thr Val 960 |
| Leu | Glu | Pro | Gln | Gly 965 | Ala | Met | Leu | Asp | Leu 970 | Leu | Gly | Val | Arg | Gly Pro 975 |
| His | Pro | Thr | Glu 980 | Pro | Gly | Ala | Asn | Ala 985 | Arg | Gln | Leu | Ala | Arg 990 | Ile Ile |
| Ala | Cys | Ala 995 | Val | Leu | Ala | Gly | Glu 1000 | Leu | Ser | Leu | Cys | Ser 1005 | Ala | Leu Ala |
| Ala | Gly 1010 | His | Leu | Val | Gln | Ser 1015 | His | Met | Thr | His | Asn 1020 | Arg | Lys | Thr Asn |
| Lys 1025 | Ala | Asn | Glu | Leu | Pro 1030 | Gln | Pro | Ser | Asn | Lys 1035 | Gly | Pro | Pro | Cys Lys 1040 |
| Thr | Ser | Ala | Leu | Leu 1045 | | | | | | | | | | |